(12) United States Patent
Reiter et al.

(10) Patent No.: US 7,119,201 B2
(45) Date of Patent: Oct. 10, 2006

(54) TRIARYL-OXY-ARYLOXY-PYRIMIDINE-2,4,6-TRIONE METALLOPROTEINASE INHIBITORS

(75) Inventors: Lawrence Alan Reiter, Mystic, CT (US); Kevin Daniel Freeman-Cook, Clinton, CT (US)

(73) Assignee: Pfizer Inc, New York, NY (US)

( * ) Notice: Subject to any disclaimer, the term of this patent is extended or adjusted under 35 U.S.C. 154(b) by 385 days.

(21) Appl. No.: 10/424,614

(22) Filed: Apr. 28, 2003

(65) Prior Publication Data

US 2004/0006057 A1 Jan. 8, 2004

Related U.S. Application Data

(60) Provisional application No. 60/375,990, filed on Apr. 26, 2002.

(51) Int. Cl.
| | |
|---|---|
| C07D 239/02 | (2006.01) |
| C07D 401/00 | (2006.01) |
| C07D 239/62 | (2006.01) |
| A01N 43/54 | (2006.01) |

(52) U.S. Cl. .................. 544/299; 544/300; 544/301; 544/302; 544/303; 544/304; 544/306; 544/307; 514/270

(58) Field of Classification Search ................ 544/299, 544/300, 301, 302, 303, 304, 305, 306, 307; 514/270

See application file for complete search history.

(56) References Cited

U.S. PATENT DOCUMENTS

| | | | |
|---|---|---|---|
| 6,579,982 | B1 | 6/2003 | Blagg |
| 2002/0132822 | A1 | 9/2002 | Noe et al. |
| 2003/0096803 | A1 | 5/2003 | Noe et al. |
| 2003/0225056 | A1 | 12/2003 | Freeman-Cook et al. |
| 2004/0006057 | A1 | 1/2004 | Reiter et al. |
| 2004/0010141 | A1 | 1/2004 | Noe et al. |

FOREIGN PATENT DOCUMENTS

| | | |
|---|---|---|
| EP | 606046 | 7/1994 |
| WO | 98/58925 | 12/1998 |
| WO | 00/47565 | 8/2000 |

OTHER PUBLICATIONS

Mitchell, G. et al., "Cloning, Expression, and Type II Collagenolytic Activity of Matrix Metalloproteinase–13 from Human Osteoarthritic Cartilage," *J. Clin. Invest.*, 97, pp. 761–768, (1996).

Goodman, et al., *The Pharmacological Basis of Therapeutics*, 8th Ed., 345–382, (1990).

Lednicer,et al., *The Organic Chemistry of Drug Synthesis*, 1, 167–277.

Niederl, J.B. et al., "Disproportionation in Aryloxymalonic Acid Syntheses," *J. Amer. Chem Soc.*, 62, 1154–1156, (1940).

Campbell, M. et al., "The Preparation and Crystal Structure of 2–Phenoxypropenoic Acid," *Aust. J. Chem.*, 45, 2061–2066, (1992).

Peace, B.W. et al., "The Soluble Copper (I)–Catalyzed Decomposition of Dimethyl Diazomalonate and Di–t–butyl Diazomalonate in the Presence of Some Cycloalkenes," *Synthesis*, 12, 658–662, (1971).

Mitsonubu, O., "The Use of Diethyl Azodicarboxylate and Triphenylphosphine in Synthesis and Transformation of Natural Products," *Synthesis*, 1, 1–28, (1981).

Vida, J.A. et al., "Analgesics. 1. Selected 5–Substituted 5–Propionoxybarbituric Acids," *J. Med. Chem.*, 17, pp. 732–736, (1974).

Tate, J.V., et al., "Preparation of 5–Substituted Benzylbarburituric Acids and Investigation of the Effect of the Benzyl and Substituted Benzyl Groups on the Acidity of Barbituric Acid," *J. Het. Chem.*, 23(1), 9–11 (1986).

Hartwig, J.F., "Transition Metal Catalyzed Synthesis of Arylamines and Aryl Ethers from Aryl Halides and Triflates: Scope and Mechanism," *Angew. Chem. Int. Ed. Engl.*, 37,(13/14), 2046–2067, (1998).

Cawston, et al., "A Rapid and Reproducible Assay for Collagenase Using [1–$^{14}$C] Acetylated Collagen," *Anal. Biochem.* 99(2), pp. 340–345, (1979).

Johnson–Wint, B., "A Quantitative Collagen Film Collagenase Assay for Large Numbers of Samples," *Anal. Biochem.*, 104(1), 175–181, (1980).

Whitney, S.E., et al., "Benzyne–Oxazole Cycloadducts: Isolation and Retro–Diels–Alder Reactions," *J. Org. Chem.*, 55 (3), 929–935, (1990).

(Continued)

*Primary Examiner*—James O. Wilson
*Assistant Examiner*—Paul V. Ward
(74) *Attorney, Agent, or Firm*—Austin W. Zhang; Richard L. Catania

(57) ABSTRACT

The present invention relates to triaryl-oxy-aryloxy-pyrimidine-2,4,6-trione; metalloproteinase inhibitors of the formula

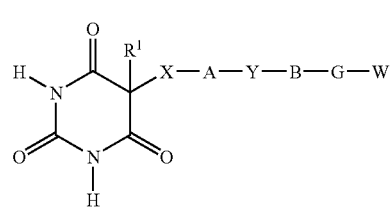

wherein X, A, Y, B, G, W, and R$^1$ are as defined in the specification, and to pharmaceutical compositions and methods of treating inflammation, cancer and other disorders.

53 Claims, No Drawings

OTHER PUBLICATIONS

Kashima, C. et al., "Synthesis of 2-Aryl-and 5-Alkyl-2-aryloxazoles from 2-Aryl-5-bromooxazoles," *Synthesis*, 11, 873–874, (1989).

Gangloff, A.R. et al, "Synthesis of 3,5-disubstituted-1,2,4-oxadiazoles using tetrabutylammonium fluoride as a mild and efficient catalyst," *Tetrahedron Letters*, 42(8), 1441–1443, (2001).

Blackhall, A. et al, "Substitution Reactions of Phenylated Aza-heterocycles. Part 1.," *J. Chem. Soc. Perkin Transactions II*, 773–777, (1980).

TRIARYL-OXY-ARYLOXY-PYRIMIDINE-2,4, 6-TRIONE METALLOPROTEINASE INHIBITORS

This application claims benefit to U.S. Provisional Application Ser. No. 60/375,990 filed on Apr. 26, 2002.

BACKGROUND OF THE INVENTION

The present invention relates to triaryloxy-aryloxy-pyrimidine-2,4,6-trione metalloproteinase inhibitors and to pharmaceutical compositions and methods of treatment of inflammation, cancer and other disorders.

The compounds of the present invention are inhibitors of zinc metalloendopeptidases, especially those belonging to the class of matrix metalloproteinases (also called MMPs or matrixins).

The MMP subfamily of enzymes currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMPs are most well known for their role in regulating the turn-over of extracellular matrix proteins and as such play important roles in normal physiological processes such as reproduction, development and differentiation. In addition, the MMPs are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMPs is expected to slow or block the accelerated loss of cartilage typical of joint diseases such as osteoarthritis or rheumatoid arthritis.

It is recognized that different combinations of MMPs are expressed in different pathological situations. As such, inhibitors with specific selectivities for individual MMPs may be preferred for individual diseases.

MMP inhibitors are well known in the literature. Hydroxamic acid MMP inhibitors are exemplified in European Patent Publication 606,046, published Jul. 13, 1994. Several pyrimidine-2,4,6-trione MMP inhibitors are referred to in PCT publication WO 98/58925, published Dec. 30, 1998. PCT publication WO 00/47565, published Aug. 17, 2000 refers to certain aryl substituted pyrimidine-2,4,6-trione MMP inhibitors. U.S. Non-provisional application Ser. No. 09/635,156, filed Aug. 9, 2000 (which claims priority to U.S. Provisional application 60/148,547 filed Aug. 12, 1999) refers to heteroaryl substituted pyrimidine-2,4,6-trione MMP inhibitors. United States Provisional Applications entitled "Triaryl-Oxy-Aryl-Spiro-Pyrimidine-2,4,6-Trione Metalloproteinase Inhibitors"; "N-Substituted-Heteroaryloxy-Aryl-Spiro-Pyrimidine-2,4,6-Trione Metalloproteinase Inhibitors"; and "N-Substituted-Heteroaryloxy-Aryloxy-Pyrimidine-2,4,6-Trione Metalloproteinase Inhibitors", all filed Apr. 26, 2002, refer to certain pyrimidine-2,4,6-triones. Barbituric acids and methods for their preparation are well known in the art, see for example Goodman and Gilman's, "*The Pharmacological Basis of Therapeutics,*" 345–382 (Eighth Edition, McGraw Hill, 1990). Each of the above referenced publications and applications is hereby incorporated by reference in its entirety.

U.S. Non-provisional application Ser. No. 10/047,592, filed 23 Oct., 2001 (which claims priority to U.S. Provisional application 60/243,389 filed 26 Oct., 2000) refers to heteroaryl substituted pyrimidine-2,4,6-trione MMP inhibitors. U.S. Non-provisional application Ser. No. 10/032,837, filed 25 Oct., 2001 (which claims priority to U.S. Provisional application 60/243,314, filed 26 Oct., 2000) refers to heteroaryl substituted pyrimidine-2,4,6-trione MMP inhibitors. Each of the above referenced applications refer to certain heteroaryl substituted pyrimidine-2,4,6-trione MMP inhibitors containing N-methylazetidinyl or N-methylpiperidinyl. Each of the above referenced applications is hereby incorporated by reference in its entirety.

SUMMARY OF THE INVENTION

The present invention relates to compounds of the formula

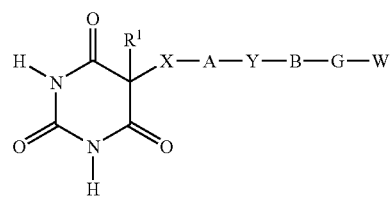

wherein $R^1$ is selected from the group consisting of hydrogen, $(R^2)_{2n+1}$—$(C)_n$— and $(C_3$–$C_7)$cycloalkyl; wherein said $(C_3$–$C_7)$cycloalkyl may be optionally substituted on any ring carbon atom able to support an additional substituent by one to two substituents independently selected from the group consisting of halo, $(C_1$–$C_4)$alkyl, $(C_1$–$C_4)$alkenyl, $(C_1$–$C_4)$alkynyl, $R^3$—, $R^3$—O—, perfluoro$(C_1$–$C_4)$alkoxy, $R^3$—$(C_1$–$C_4)$alkyl-O—, $R^3$—(C=O)—O—, $(R^3)_2$N—(C=O)—O—, —$NO_2$, $(R^3)_2$N—, $R^3$—(C=O)—(NR$^4$)—, $R^3$—$(SO_2)$—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—$(SO_2)$—, $(R^3)_2$N—$(SO_2)$—, —CN, $R^3$—(C=O)—, $R^3$—O—(C=O)— and $(R^3)_2$N—(C=O)—;

n is an integer from one to five;

each $R^2$ is independently selected from the group consisting of halo, $(C_1$–$C_4)$alkenyl, $(C_1$–$C_4)$alkynyl, $R^3$—, $R^3$—O—, perfluoro$(C_1$–$C_4)$alkoxy, $R^3$—(C=O)—O—, $(R^3)_2$N—(C=O)—O—, —$NO_2$, $(R^3)_2$N—, $R^3$—$(SO_2)$—(NR$^4$)—, $(R^3)_2$—N—(C=O)—, $R^3$—(C=O)—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—$(SO_2)$—, $(R^3)_2$N—$(SO_2)$—, —CN, $R^3$—O—(C=O)—, and $R^3$—(C=O)—;

wherein not more than three of said $R^2$ may be other than hydrogen and any one carbon atom of said —$(C)_n$— component of the $R^1$ can contain only one bond to a heteroatom;

wherein a carbon atom of any two $R^2$ may be taken together with the carbons to which they are attached to form a four to ten membered ring;

each $R^3$ is independently selected from the group consisting of hydrogen, $(C_1$–$C_4)$alkyl, $(C_6$–$C_{10})$aryl, $(C_3$–$C_7)$cycloalkyl, $(C_1$–$C_{10})$heteroaryl and $(C_1$–$C_{10})$heterocyclyl; wherein each $R^3$ may be optionally substituted on any carbon atom able to support an additional substituent by one to three substituents, wherein said substituents are independently selected from the group consisting of halo, hydroxy, amino, —CN, $(C_1$–$C_4)$alkyl, $(C_1$–$C_4)$alkoxy, $(C_1$–$C_4)$alkyl-NH—, $[(C_1$–$C_4)$alkyl$]_2$—N—, $(C_6$–$C_{10})$aryl, $(C_3$–$C_7)$cycloalkyl, $(C_1$–$C_{10})$heteroaryl and $(C_1$–$C_{10})$heterocyclyl;

wherein each of said $R^3$ $(C_3$–$C_7)$cycloalkyl and $(C_1$–$C_{10})$heterocyclyl may be optionally substituted on any ring carbon atoms capable of supporting two additional substituents with one to two oxo groups per ring;

wherein each of said $R^3$ $(C_1-C_{10})$heteroaryl and $(C_1-C_{10})$heterocyclyl may be optionally substituted on any ring nitrogen atom able to support an additional substituent independently selected from the group consisting of $(C_1-C_4)$alkyl, $(C_1-C_4)$alkyl-(C=O)—, $(C_6-C_{10})$aryl, $(C_3-C_7)$cycloalkyl, $(C_1-C_{10})$heteroaryl and $(C_1-C_{10})$heterocyclyl;

$R^4$ is selected from the group consisting of hydrogen and $(C_1-C_4)$alkyl;

wherein said $R^3$ may be optionally taken together with said $R^4$ to form a three to eight membered ring;

X is selected from the group consisting of —O—, >C=O, —S—, >SO$_2$, >SO$_2$, >NR$^5$, —CH$_2$—, —CH$_2$O—, —OCH$_2$—, —CH$_2$S—, —CH$_2$(S=O)—, —CH$_2$SO$_2$—, —SCH$_2$—, —(S=O)CH$_2$—, —SO$_2$CH$_2$—, —[N(R$^5$)]CH$_2$—, —CH$_2$[N(R$^5$)]—, —[N(R$^5$)]SO$_2$— and —SO$_2$[N(R$^5$)]—;

$R^5$ is selected from the group consisting of hydrogen and $(C_1-C_4)$alkyl;

A is $(C_6-C_{10})$aryl or $(C_1-C_{10})$heteroaryl;

Y is selected from the group consisting of a bond, —O—, —S—, >C=O, >SO$_2$, >S=O, —CH$_2$O—, —OCH$_2$—, —CH$_2$S—, —SCH$_2$—, —CH$_2$SO—, —CH$_2$SO$_2$—, —SOCH$_2$—, —SO$_2$CH$_2$—, >NR$^6$, —[N(R$^6$)]CH$_2$—, CH$_2$[N(R$^6$)]—, —CH$_2$—, —CH=CH—, —C≡C—, —[N(R$^6$)]—SO$_2$— and —SO$_2$[N(R$^6$)]—;

$R^6$ is selected from the group consisting of hydrogen and $(C_1-C_4)$alkyl;

B is selected from the group consisting of $(C_6-C_{10})$aryl, $(C_3-C_7)$cycloalkyl, $(C_1-C_{10})$heterocyclyl and $(C_1-C_{10})$heteroaryl; wherein one or two carbon-carbon single bonds of said B $(C_3-C_7)$cycloalkyl or $(C_1-C_{10})$heterocyclyl may optionally be replaced by carbon-carbon double bonds;

wherein G is bonded to one ring carbon atom of B;

wherein each of said A or B may be independently optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy;

G is —[R$^7$—(CR$^8$R$^9$)$_p$]—; wherein the orientation of -B-G-W is -B-[R$^7$—(CR$^8$R$^9$)$_p$]-W or -B-[(CR$^8$R$^9$)—R$^7$]-W;

p is an integer from zero to four;

$R^7$ is independently selected from the group consisting of $(C_3-C_7)$cycloalkyl, $(C_6-C_{10})$aryl, $(C_1-C_{10})$heteroaryl and $(C_1-C_{10})$heterocyclyl;

wherein each of said $(C_6-C_{10})$aryl, $(C_3-C_7)$cycloalkyl, $(C_1-C_{10})$heteroaryl and $(C_1-C_{10})$heterocyclyl may be optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$;

wherein each of said $R^7$ $(C_3-C_7)$cycloalkyl and $(C_1-C_{10})$heterocyclyl may optionally be substituted on any ring carbon atoms capable of supporting two additional substituents with one to two oxo groups per ring;

wherein each of said $R^7$ $(C_1-C_{10})$heteroaryl and $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

each of $R^8$ and $R^9$ is independently selected from the group consisting of hydrogen and $(C_1-C_4)$alkyl;

or $R^3$ and $R^9$ may optionally be taken together with the carbon to which they are attached to form a 3 to 8-membered carbocyclic ring;

W is selected from the group consisting of $(C_1-C_4)$alkoxy$(C_1-C_4)$alkyl, $(C_3-C_7)$cycloalkyl, $(C_6-C_{10})$aryl, $(C_1-C_{10})$heteroaryl and $(C_1-C_{10})$heterocyclyl;

wherein each of said W $(C_3-C_7)$cycloalkyl, $(C_6-C_{10})$aryl, $(C_1-C_{10})$heteroaryl and $(C_1-C_{10})$heterocyclyl may be optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy;

wherein each of said W $(C_3-C_7)$cycloalkyl and $(C_1-C_{10})$heterocyclyl may optionally be substituted on any ring carbon atoms capable of supporting two additional substituents with one to two oxo groups per ring;

wherein each of said W $(C_1-C_{10})$heteroaryl and $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

or the pharmaceutically acceptable salts thereof.

The present invention also relates to the pharmaceutically acceptable acid addition salts of compounds of the formula 1. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention may also exist in different tautomeric forms. This invention relates to all tautomers of formula 1.

The compounds of this invention may contain olefin-like double bonds. When such bonds are present, the compounds of the invention exist as cis and trans configurations and as mixtures thereof.

Some compounds of formula I contain chiral centers and therefore exist in different enantiomeric forms. This invention relates to all optical isomers, enantiomers, diastereomers and stereoisomers of the compounds of formula I and mixtures thereof. The compounds of the invention also exist in different tautomeric forms. This invention relates to all tautomers of formula I. Those skilled in the art are well aware that the pyrimidine-2,4,6-trione nucleus exists as a mixture of tautomers in solution. The various ratios of the tautomers in solid and liquid form is dependent on the various substituents on the molecule as well as the particular crystallization technique used to isolate a compound.

Unless otherwise indicated, the term "substituent" or "substituents" refers to a replacement of at least one atom of an individual member of a variable (e.g., $R^1$, $R^2$, and $R^3$) of the compound of the formula I by another atom or group of atoms. For example, an $(C_1-C_6)$alkyl substituent may replace a hydrogen atom of the $R^1$ $(C_6-C_{10})$aryl.

Unless otherwise indicated, the term "$(C_1-C_4)$alkyl" or "$(C_1-C_6)$alkyl", as well as the $(C_1-C_4)$alkyl or $(C_1-C_6)$alkyl component of other terms referred to herein (e.g., the "$(C_1-C_6)$alkyl component of $(C_1-C_6)$alkyl-O—), may be linear or branched (such as methyl, ethyl, n-propyl, isopropyl, n-butyl, iso-butyl, secondaty-butyl, tertiary-butyl) hydrocarbon chain of 1 to 4, or 1 to 6, carbon atoms.

Unless otherwise indicated, the term "halo" means fluoro, chloro, bromo or iodo.

Unless otherwise indicated, the term "$(C_2-C_6)$alkenyl" means straight or branched hydrocarbon chain of 2 to 6 carbon atoms having at least one double bond including, but not limited to ethenyl, 1-propenyl, 2-propenyl (allyl), iso-propenyl, 2-methyl-1-propenyl, 1—Butenyl, or 2—Butenyl.

Unless otherwise indicated, the term "$(C_2-C_6)$alkynyl" is used herein to mean straight or branched hydrocarbon chain of 2 to 6 carbon atoms having one triple bond including, but not limited to, ethynyl (—C≡C—H), propynyl (—CH$_2$—C≡C—H or —C≡C—CH$_3$), or butynyl (—CH$_2$—CH$_2$—C≡C—H, or —CH$_2$—C≡C—CH$_3$, or —C≡C—CH$_2$CH$_3$).

Unless otherwise indicated, the term "$(C_3-C_7)$cycloalkyl" refers to a mono or bicyclic carbocyclic ring of 3 to 7 carbon atoms including, but not limited to, cyclopropyl, cyclobutyl, cyclopentyl, cyclohexyl, cycloheptyl and bicyclo[2.2.1]heptanyl; wherein said $(C_3-C_7)$cycloalkyl may optionally contain 1 or 2 double bonds including, but not limited to, cyclopentenyl, cyclohexenyl and cycloheptenyl.

Unless otherwise indicated, the term "$(C_6-C_{10})$aryl" refers to an aromatic ring such as phenyl, naphthyl, tetrahydronaphthyl, or indanyl.

Unless otherwise indicated, the term "oxo" refers to a carbonyl group (i.e., =O).

Unless otherwise indicated, the term "$(C_1-C_{10})$heteroaryl" refers to aromatic or multicyclic rings wherein at least one ring is aromatic, wherein said aromatic or multi-cyclic rings contain one or more heteroatoms selected from the group consisting of O, S and N. Examples of $(C_1-C_{10})$heteroaryl include, but are not limited to, benzimidazolyl, benzofuranyl, benzofurazanyl, 2H-1—Benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl. Unless otherwise indicated, the foregoing $(C_1-C_{10})$heteroaryl can be C-attached or N-attached where such is possible.

Unless otherwise indicated, the term "$(C_1-C_{10})$heterocyclyl" refers to a ring containing 1 to 10 carbon atoms and 1 to 4 heteroatoms selected from the group consisting of N, O and S. Examples of $(C_1-C_{10})$heterocyclyl include, but not limited to, 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxetanyl oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. Unless otherwise indicated, the foregoing $(C_1-C_{10})$heterocyclyl can be C-attached or N-attached where such is possible. For example, piperidinyl can be piperidin-1-yl (N-attached) or piperidin-4-yl (C-attached).

In one embodiment of the invention, W is $(C_1-C_4)$alkoxy$(C_1-C_4)$alkyl, preferably W is methoxymethyl, methoxyethyl, methoxypropyl, methoxybutyl, ethoxymethyl, ethoxyethyl, ethoxypropyl, or ethoxybutyl; more preferably methoxymethyl.

In another embodiment of the invention, W is $(C_3-C_7)$cycloalkyl selected from the group consisting of optionally substituted cyclopropyl, cyclobutyl, cyclopentyl, cyclohexyl, and cycloheptyl; preferably cyclopentyl, cyclohexyl, and cycloheptyl; wherein said $(C_3-C_7)$cycloalkyl is optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; preferably selected from F, Cl, Br, CN, OH, $(C_1-C_4)$alkyl, $(C_1-C_4)$alkoxy$(C_1-C_4)$alkyl, and $(C_1-C_4)$alkoxy; more preferably selected from F, CN, methyl, ethyl, methoxymethyl, and methoxy; and wherein said W $(C_3-C_7)$cycloalkyl may optionally be substituted on any ring carbon atoms capable of supporting two additional substituents with one to two oxo groups per ring.

In another embodiment of the invention, W is $(C_6-C_{10})$aryl, preferably phenyl, optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; preferably selected from F, Cl, CN, $(C_1-C_4)$alkyl, $(C_1-C_4)$alkoxy$(C_1-C_4)$alkyl, and $(C_1-C_4)$alkoxy; more preferably selected from F, CN, methyl, ethyl, methoxymethyl, and methoxy.

In another embodiment of the invention, W is unsubstituted phenyl.

In another embodiment of the invention, W is $(C_1-C_{10})$heteroaryl selected from the group consisting of furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl; preferably selected from the group consisting of pyridinyl, pyridazinyl, pyrazolyl, isoxazolyl, oxadiazolyl, and oxazolyl; more preferably selected from the group consisting of pyridinyl and pyrimidinyl; wherein said W $(C_1-C_{10})$heteroaryl is optionally substituted on any of the ring carbon atoms capable of supporting an additional substituent by one to three substituents per ring independently selected from the group consisting of F, Cl, Br, CN, OH, $(C_1-C_4)$alkyl, $(C_1-C_4)$alkoxy$(C_1-C_4)$alkyl, $(C_1-C_4)$ perfluoroalkyl, $(C_1-C_4)$perfluoroalkoxy, $(C_1-C_4)$alkoxy, and $(C_3-C_7)$cycloalkyloxy; preferably selected from the group consisting of F, Cl, CN, $(C_1-C_4)$alkyl, $(C_1-C_4)$alkoxy$(C_1-C_4)$alkyl, and $(C_1-C_4)$alkoxy; more preferably selected from the group consisting of F, CN, methyl, ethyl, methoxymethyl, and methoxy; and wherein said W $(C_1-C_{10})$heteroaryl may be also optionally substituted on any ring nitrogen atom able to support an additional substituent independently selected from the group consisting of $(C_1-C_4)$alkyl and $(C_1-C_4)$alkyl-(C=O)—.

In another embodiment of the invention, W is $(C_1-C_{10})$heterocyclyl selected from the group consisting of azetidinyl, hexahydroazepinyl, morpholinyl, piperazinyl, piperidinyl, pyrrolidinyl, thiomorpholinyl, tetrahydrofuranyl, tetrahydropyranyl, and oxetanyl; preferably selected from the group consisting of azetidinyl, hexahydroazepinyl, morpholinyl, piperidinyl, pyrrolidinyl, thiomorpholinyl, tetrahydrofuranyl, tetrahydropyranyl, and oxetanyl; more preferably selected from the group consisting of azetidinyl, morpholinyl, piperidinyl, pyrrolidinyl, thiomorpholinyl, tetrahydrofuranyl, and tetrahydropyranyloptionally; wherein said W $(C_1-C_{10})$heterocyclyl is optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; preferably selected from F, Cl, CN, $(C_1-C_4)$alkyl, $(C_1-C_4)$alkoxy$(C_1-C_4)$alkyl, and $(C_1-C_4)$alkoxy; more preferably selected from F, CN, methyl, ethyl, methoxymethyl, and methoxy; wherein said $(C_1-C_{10})$heterocyclyl may optionally be substituted on any ring carbon atoms capable of supporting two additional substituents with one to two oxo groups per ring; and wherein said $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—.

In another embodiment of the invention, W is unsubstituted $(C_1-C_{10})$heterocyclyl.

In each of the above embodiments of the invention, A is $(C_1-C_{10})$heteroaryl selected from the group consisting of benzimidazolyl, benzofuranyl, benzofurazanyl, 2H-1—Benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said A $(C_1-C_{10})$heteroaryl is optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy; preferably A is selected from the group consisting of imidazolyl, isothiazolyl, isoxazolyl, oxadiazolyl, oxazolyl, pyrazinyl, pyridazinyl, pyridinyl, pyrimidinyl and pyrazolyl; more preferably A is selected from the group consisting of pyrazinyl, pyridazinyl, pyridyl and pyrimidinyl; most preferably A is pyridinyl. Within each of the aforesaid embodiments, Y is selected from the group consisting of a bond, —O—, —S—, —CH$_2$—, >SO$_2$, —OCH$_2$— and —CH$_2$O—; preferably Y is —O—, —OCH$_2$— or —CH$_2$O—; more preferably Y is —O—.

In another embodiment of each of the above embodiments of the invention, A is $(C_6-C_{10})$aryl, such as phenyl or naphthyl, wherein said is $(C_6-C_{10})$aryl is optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy; preferably A is phenyl. Within each of the aforesaid embodiments, Y is selected from the group consisting of a bond, —O—, —S—, —CH$_2$—, >SO$_2$, —OCH$_2$— and —CH$_2$O—; preferably Y is —O—, —OCH$_2$— or —CH$_2$O—; more preferably Y is —O—.

In another embodiment of the invention, A is substituted on any of the ring carbon atoms capable of supporting an additional substituent by one or two substituents per ring independently selected from F, Cl, CN, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

In another embodiment of the invention, B is $(C_6-C_{10})$aryl, preferably phenyl, optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

In another embodiment of the invention, B is $(C_3-C_7)$cycloalkyl; preferably cyclopentyl or cyclohexyl, optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

In another embodiment of the invention, B is $(C_1-C_{10})$heteroaryl selected from the group consisting of benzimidazolyl, benzofuranyl, benzofurazanyl, 2H-1—Benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, and pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; preferably selected from the group consisting of furyl, imidazolyl, isothiazolyl, isoxazolyl, pyrazinyl, pyridazinyl, pyridinyl, pyrimidinyl, pyrazolyl, pyrrolyl, thiazolyl, thiadiazolyl, thienyl, triazinyl and triazolyl; more preferably selected from the group consisting of pyrazinyl, pyridazinyl, pyridinyl, and pyrimidinyl; wherein said B $(C_1-C_{10})$heteroaryl is optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

In another embodiment of the invention, the group -B-G-W has the formula -B-[R$^7$—(CR$^8$R$^9$)$_p$]-W.

In another embodiment of the invention, the group -B-G-W has the formula -B-[(CR$^8$R$^9$)$_p$—R$^7$]-W.

In another embodiment of the invention, the group -B-G-W has the formula —$(C_6-C_{10})$aryl-[$(C_1-C_{10})$heteroaryl-(CR$^8$R$^9$)$_p$]—$(C_6-C_{10})$aryl; wherein p is zero; wherein each of said B $(C_6-C_{10})$aryl and W $(C_6-C_{10})$aryl are optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, $(C_1-C_4)$alkyl-NH—, [$(C_1-C_4)$alkyl]$_2$—N— and $(C_3-C_7)$cycloalkyloxy; and wherein said G $(C_1-C_{10})$ heteroaryl is optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, $(C_1-C_4)$alkyl-N H—, [$(C_1-C_4)$alkyl]$_2$—N— and $(C_3-C_7)$cycloalkyloxy.

In another embodiment of the invention, both A and B are substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy; preferably selected from the group consisting of F, Cl, CN, methyl, perfluoromethyl, perfluoromethoxy, methoxy, and ethoxy.

In another preferred embodiment of the invention, either A or B is unsubstituted.

In another preferred embodiment of the invention, both A and B are unsubstituted.

In another embodiment of the invention, G is $(C_3-C_7)$ cycloalkyl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$; and wherein said $(C_3-C_7)$cycloalkyl may optionally be substituted on any ring carbon atoms capable of supporting two additional substituents with one to two oxo groups per ring.

In another embodiment of the invention, G is $(C_6-C_{10})$ aryl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$; preferably G is phenyl optionally substituted on any of the ring carbon atoms capable of supporting an additional substituent by one to three substituents per ring independently selected from F, Cl, CN, $(C_1-C_4)$alkyl, $(C_1-C_4)$alkoxy, $(C_1-C_4)$alkoxy$(C_1-C_4)$alkyl, and $(C_3-C_7)$cycloalkyloxy; more preferably G is phenyl optionally substituted on any of the ring carbon atoms capable of supporting an additional substituent by one substituent per ring independently selected from F, Cl, CN, methyl, ethyl, isopropyl, methoxy, methoxymethyl, methoxyethyl, and cyclopentyloxy.

In another embodiment of the invention, G is unsubstituted $(C_6-C_{10})$aryl; preferably G is unsubstituted phenyl.

In another embodiment of the invention, G is $(C_1-C_{10})$ heteroaryl selected from the group consisting of benzimidazolyl, benzofuranyl, benzofurazanyl, 2H-1—Benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; wherein said $(C_1-C_{10})$heteroaryl is optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$; preferably G is $(C_1-C_{10})$heteroaryl selected from the group consisting of furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl; optionally substituted on any of the ring carbon atoms capable of supporting an additional substituent by one or two substituents per ring independently selected from the group consisting of F, Cl, CN, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy; more preferably G is $(C_1-C_{10})$ heteroaryl selected from the group consisting of furyl, imidazolyl, isothiazolyl, isoxazolyl, oxadiazolyl, oxazolyl, pyrazolyl, pyrrolyl, tetrazolyl, thiazolyl, thiadiazolyl, thienyl, and triazolyl optionally substituted on any of the ring carbon atoms capable of supporting an additional substituent by one or two substituents per ring independently selected from the group consisting of F, Cl, CN, methyl, ethyl, isopropyl, methoxy, methoxymethyl, methoxyethyl, and cyclopentyloxy; most preferably G is $(C_1-C_{10})$ heteroaryl selected from the group consisting of oxazolyl, isoxazolyl, pyrazolyl, and oxadiazolyl optionally substituted on any of the ring carbon atoms capable of supporting an additional substituent by one to two substituents per ring independently selected from the group consisting of F, Cl, CN, methyl, ethyl, isopropyl, methoxy, methoxymethyl, methoxyethyl, and cyclopentyloxy.

In another embodiment of the invention, G is oxazol-2-yl or oxazol-5-yl optionally substituted on any of the ring carbon atoms capable of supporting an additional substituent by one or two substituents per ring independently selected from the group consisting of F, Cl, Br, CN, OH, $(C_1-C_4)$ alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$.

In another embodiment of the invention, G is isooxazol-5-yl or isooxazol-3-yl optionally substituted on any of the ring carbon atoms capable of supporting an additional substituent by one or two substituents per ring independently selected from the group consisting of F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$.

In another embodiment of the invention, G is oxadiazol-2-yl, oxadiazol-3-yl, or oxadiazol-5-yl optionally substituted on any of the ring carbon atoms capable of supporting an additional substituent by one or two substituents per ring independently selected from the group consisting of F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$.

In another embodiment of the invention, G is pyrazolyl optionally substituted on any of the ring carbon atoms capable of supporting an additional substituent by one or two substituents per ring independently selected from the group consisting of F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$.

In another embodiment of the invention, G is unsubstituted $(C_1-C_{10})$heteroaryl selected from the group consisting of benzimidazolyl, benzofuranyl, benzofurazanyl, 2H-1—benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; preferably G is selected from the group consisting of unsubstituted furyl, imidazolyl, isothiazolyl, isoxazolyl, oxadiazolyl, pyrazinyl, pyridazinyl, pyridinyl, pyrimidinyl, pyrazolyl, pyrrolyl, oxazolyl, tetrazolyl, thiazolyl, thiadiazolyl, thienyl, triazinyl and triazolyl; more preferably G is selected from the group consisting of unsubstituted furyl, imidazolyl, isothiazolyl, isoxazolyl, oxadiazolyl, pyrazinyl, pyrazolyl, pyrrolyl, oxazolyl, tetrazolyl, thiazolyl, thiadiazolyl, thienyl, triazinyl and triazolyl; most preferably G is selected from the group consisting of unsubstituted oxazolyl, isoxazolyl, pyrazolyl and oxadiazolyl.

In another embodiment of the invention, G is $(C_1-C_{10})$heterocyclyl selected from the group consisting of azetidinyl, hexahydroazepinyl, morpholinyl, piperazinyl, piperidinyl, pyrrolidinyl, thiomorpholinyl, tetrahydrofuranyl, tetrahydropyranyl, and oxetanyl; preferably selected from the group consisting of azetidinyl, hexahydroazepinyl, morpholinyl, piperidinyl, pyrrolidinyl, thiomorpholinyl, tetrahydrofuranyl, tetrahydropyranyl, and oxetanyl; more preferably selected from the group consisting of azetidinyl, morpholinyl, piperidinyl, pyrrolidinyl, thiomorpholinyl, tetrahydrofuranyl, and tetrahydropyranyl; wherein said $(C_1-C_{10})$heterocyclyl is optionally substituted on any of the ring carbon atoms capable of supporting an additional substituent by one to three substituents per ring independently selected from the group consisting of F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$; and wherein said $(C_1-C_{10})$heterocyclyl may optionally be substituted on any ring carbon atoms capable of supporting two additional substituents with one to two oxo groups per ring.

In another embodiment of the invention, G is $R^7-(CR^8R^9)_p-$; wherein p is an integer from one to four, preferably from one to two; and wherein each of $R^8$ or $R^9$ is independently hydrogen, methyl, ethyl, propyl, or isopropyl.

In another embodiment of the invention, G is $R^7-(CR^8R^9)_p-$; wherein p is an integer from one to four, preferably from one to two; and wherein $R^8$ and $R^9$ are taken together with the carbon to which they are attached to form a 3 to 8-membered carbocyclic ring selected from the group consisting of cyclopropyl, cyclobutyl, cyclopentyl, cyclohexyl, cycloheptyl, cyclooctyl, cyclopentenyl, and cyclohexenyl.

In another embodiment of the invention, G is $(C_3-C_7)$cycloalkyl-$(CR^8R^9)_p-$; wherein p is an integer from one to four, preferably from one to two; wherein said $(C_3-C_7)$cycloalkyl is optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-N H_2$, $-(C=O)-N H-(C_1-C_4)$alkyl, and $-(C=O)-N[(C_1-C_4)$alkyl$]_2$; wherein said G $(C_3-C_7)$cycloalkyl may optionally be substituted on any ring carbon atoms capable of supporting two additional substituents with one to two oxo groups per ring; and wherein each of $R^8$ and $R^9$ is independently hydrogen.

In another embodiment of the invention, G is $(C_6-C_{10})$aryl-$(CR^8R^9)_p-$; wherein p is an integer from one to four, preferably from one to two; wherein said $(C_6-C_{10})$aryl is optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$; and wherein each of $R^8$ and $R^9$ is independently hydrogen.

In another embodiment of the invention, G is $(C_1-C_{10})$heteroaryl-$(CR^8R^9)_p-$; wherein p is an integer from one to four, preferably from one to two; wherein said $(C_1-C_{10})$heteroaryl is selected from the group consisting of benzimidazolyl, benzofuranyl, benzofurazanyl, 2H-1—benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; wherein said $(C_1-C_{10})$heteroaryl is optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$; preferably said G $(C_1-C_{10})$heteroaryl is selected from the group consisting of furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl; wherein said G $(C_1-C_{10})$heteroaryl component is optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl and $(C_3-C_7)$cycloalkyloxy; more preferably said G $(C_1-C_{10})$heteroaryl component is selected from the group consisting of furyl, imidazolyl, isothiazolyl, isoxazolyl, oxadiazolyl, oxazolyl, pyrazolyl, pyrrolyl, tetrazolyl, thiazolyl, thiadiazolyl, thienyl, and triazolyl optionally substituted on any of the ring carbon atoms capable of supporting an additional substituent by one or two substituents per ring independently selected from F, Cl, CN, methyl, ethyl, isopropyl, methoxy, methoxymethyl, methoxyethyl, and cyclopentyloxy; most preferably said G $(C_1-C_{10})$heteroaryl component is selected from the group consisting of isoxazolyl, oxadiazolyl, oxazolyl, and pyrazolyl optionally substituted on any of the ring carbon atoms capable of supporting an additional substituent by one to two substituents per ring independently selected from F, Cl, CN, methyl, ethyl, isopropyl, methoxy, methoxymethyl, methoxyethyl, and cyclopentyloxy; and wherein each of $R^8$ and $R^9$ is independently hydrogen.

In another embodiment of the invention, G is $(C_1-C_{10})$heterocyclyl-$(CR^8R^9)_p$—; wherein p is an integer from one to four, preferably from one to two; wherein said $(C_1-C_{10})$heterocyclyl is optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$; and wherein said $(C_1-C_{10})$heterocyclyl may optionally be substituted on any ring carbon atoms capable of supporting two additional substituents with one to two oxo groups per ring; and wherein each of $R^8$ and $R^9$ is independently hydrogen.

Another embodiment of the invention includes those compounds of formula I wherein X is —O—, —S—, >SO$_2$, >S=O, >NR$^5$, or —CH$_2$—; preferably wherein X is —O— or >NR$^5$; more preferably wherein X is —O—.

Another embodiment of the invention includes those compounds of formula I wherein Y is a bond, —O—, —S—, —CH$_2$—, >SO$_2$, —OCH$_2$— or —CH$_2$O—; preferably wherein Y is —O—, —OCH$_2$— or —CH$_2$O—; more preferably wherein Y is —O—.

Another embodiment of the invention includes those compounds of formula I wherein X is >C=O; and wherein Y is a bond, —O—, —S—, —CH$_2$—, >SO$_2$, —OCH$_2$— or —CH$_2$O—, preferably wherein Y is —O—, —OCH$_2$— or —CH$_2$O—, most preferably wherein Y is —O—.

Preferred compounds of the invention include those wherein X is —O—, —OCH$_2$—, or —CH$_2$O—, more preferably wherein X is —O—; and wherein Y is a bond, —O—, —S—, —CH$_2$—, >SO$_2$, —OCH$_2$— or —CH$_2$O—, more preferably wherein Y is —O—, —OCH$_2$— or —CH$_2$O—, most preferably wherein Y is —O—.

Other embodiments of the invention include those compounds of formula I wherein X is —S—, >SO$_2$, >S=O, —SCH$_2$—, —CH$_2$S—, —(S=O)CH$_2$—, —CH$_2$(S=O)—, —CH$_2$SO$_2$— or —SO$_2$CH$_2$—, more preferably wherein Y is a bond, —O—, —S—, —CH$_2$—, >SO$_2$, —OCH$_2$— or —CH$_2$O—, more preferably wherein Y is —O—, —OCH$_2$— or —CH$_2$O—, most preferably wherein Y is —O—.

Other embodiments of the invention include those compounds of formula I wherein X is >NR$^5$, —CH$_2$[N(R$^5$)]— or —[N(R$^5$)]CH$_2$—, more preferably wherein Y is a bond, —O—, —S—, —CH$_2$—, >SO$_2$, —OCH$_2$— or —CH$_2$O—, more preferably wherein Y is —O—, —OCH$_2$— or —CH$_2$O—, most preferably wherein Y is —O—.

Other embodiments of the invention include those compounds of formula I wherein X is —[N(R$^5$)]SO$_2$— or —SO$_2$[N(R$^5$)]—, more preferably wherein Y is a bond, —O—, —S—, —CH$_2$—, >SO$_2$, —OCH$_2$— or —CH$_2$O—, more preferably wherein Y is —O—, —OCH$_2$—, most preferably wherein Y is —O—.

Most preferred embodiment of the invention includes those compounds of formula I wherein X and Y are each —O—.

Other embodiments of the invention include those compounds of formula I wherein $R^1$ is $(C_3-C_7)$cycloalkyl wherein said $(C_3-C_7)$cycloalkyl may be optionally substituted on any ring carbon atom capable of supporting an additional substituent by one to two substituents independently selected from the group consisting of halo, $(C_1-C_4)$alkyl, $(C_1-C_4)$alkenyl, $(C_1-C_4)$alkynyl, $R^3$—, $R^3$—O—, perfluoro$(C_1-C_4)$alkoxy, $R^3$—$(C_1-C_4)$alkyl-O—, $R^3$—(C=O)—O—, —NO$_2$, $(R^3)_2$, $R^3$—(C=O)—(NR$^4$)—, $R^3$—S—$R^3$—(S=O)—, $R^3$—(SO$_2$)—, $R^3$—(SO$_2$)—(NR$^4$)—, $R^3$—NH—(SO$_2$)—, $(R^3)_2$N—(SO$_2$)—, —CN, $R^3$—(C=O)—, $R^3$—O—(C=O)— and $(R^3)_2$N—(C=O)—.

Other embodiments of the invention include those compounds of formula I wherein $R^1$ is $(R^2)_{2n+1}$—$(C)_n$— and n is an integer from one to five; each $R^2$ is independently selected from the group consisting of halo, $R^3$—, $(C_1-C_4)$alkenyl, $(C_1-C_4)$alkynyl, $R^3$—O—, perfluoro$(C_1-C_4)$alkoxy, $R^3$—(C=O)—O—, $(R^3)_2$N—(C=O)—O—, —NO$_2$, $(R^3)_2$N—, $R^3$—(SO$_2$)—(NR$^4$)—, $R^3$—(C=O)—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—(SO$_2$)—, $(R^3)_2$N—(SO$_2$)—, —CN, $R^3$—(C=O)—, $R^3$—O—(C=O)— and $(R^3)_2$N—(C=O)—; wherein not more than three of said $R^2$ substituents may be other than hydrogen and any one carbon atom of said —(C)$_n$— group can contain only one bond to a heteroatom; and each $R^3$ is independently selected from the group consisting of hydrogen, $(C_1-C_4)$alkyl, $(C_6-C_{10})$aryl, $(C_3-C_7)$cycloalkyl, $(C_1-C_{10})$heteroaryl and $(C_1-C_{10})$heterocyclyl; wherein each $R^3$ may be optionally substituted on any carbon atom able to support an additional substituent by one to three substituents independently selected from the group consisting of halo, hydroxy, amino, —CN, $(C_1-C_4)$alkyl, $(C_1-C_4)$alkoxy, $(C_1-C_4)$alkyl-NH—, [$(C_1-C_4)$alkyl]$_2$—N—$(C_6-C_{10})$aryl, $(C_3-C_7)$cycloalkyl, $(C_1-C_{10})$heteroaryl and $(C_1-C_{10})$heterocyclyl; wherein said $R^3$ group may optionally be taken together with $R^4$ to form a three to eight membered ring.

Other embodiments of the invention include those compounds of formula I wherein $R^1$ is $(R^2)_{2n+1}$—$(C)_n$—, n is an integer from one to five; at least one $R^2$ is independently selected from the group consisting of $R^3$—, $R^3$—O—, $R^3$—(C=O)—O—, $R^3$—S—, $R^3$—(S=O)—, $R^3$—(SO$_2$)—, $(R^3)_2$N—, $R^3$—(SO$_2$)—(NR$^4$)—, $R^3$—NH—(SO$_2$)—, $(R^3)_2$N—(SO$_2$)—, $R^3$—(C=O)—(NR$^4$)—, $R^3$—O—(C=O)— and $R^3$—(C=O)—; and each $R^3$ is independently selected from the group consisting of hydrogen and $(C_1$–$C_4)$alkyl; wherein each $R^3$ $(C_1$–$C_4)$alkyl may be optionally substituted on any carbon atom able to support an additional substituent by one to three substituents independently selected from the group consisting of halo, hydroxy, amino, —CN, $(C_1$–$C_4)$alkyl, $(C_1$–$C_4)$alkoxy, $(C_1$–$C_4)$alkyl-NH—, $[(C_1$–$C_4)$alkyl]$_2$—N—$(C_6$–$C_{10})$aryl, $(C_3$–$C_7)$cycloalkyl, $(C_1$–$C_{10})$heteroaryl and $(C_1$–$C_{10})$heterocyclyl; wherein said $R^3$ group may optionally be taken together with $R^4$ to form a three to eight membered ring.

Other embodiments of the invention include those compounds of formula I wherein $R^1$ is $(R^2)_{2n+1}$—$(C)_n$—, n is an integer from one to five; and each $R^2$ is independently selected from the group consisting of hydrogen, halo, $(C_1$–$C_4)$alkyl, $R^3$— and $R^3$—O—.

Other embodiments of the invention inclnds of formula I wherein n is one to three; and each $R^3$ is independently selected from the group consisting of hydrogen and $(C_1$–$C_4)$ alkyl; wherein eachyl; wherein each $R^3$ $(C_1$–$C_4)$alkyl may be optionally substituted by one to three substituents independently selected from the group consisting of halo, hydroxy, amino, —CN, $(C_1$–$C_4)$alkyl, $(C_1$–$C_4)$alkoxy, $(C_1$–$C_4)$alkyl-NH—, $[(C_1$–$C_4)$alkyl]$_2$—N—$(C_6$–$C_{10})$aryl, $(C_3$–$C_7)$cycloalkyl, $(C_1$–$C_{10})$heteroaryl and $(C_1$–$C_{10})$ heterocyclyl.

Other embodiments of the invention include those compounds of formula I wherein n is one to three; and each $R^3$ is independently selected from the group consisting of hydrogen and $(C_1$–$C_4)$alkyl; wherein at least one $R^3$ $(C_1$–$C_4)$ alkyl group is substituted by halo, hydroxy, amino, —CN, $(C_1$–$C_4)$alkyl, $(C_1$–$C_4)$alkoxy, $(C_1$–$C_4)$alkyl-NH—, $[(C_1$–$C_4)$alkyl]$_2$—N—$(C_6$–$C_{10})$aryl, $(C_3$–$C_7)$cycloalkyl, $(C_1$–$C_{10})$heteroaryl or $(C_1$–$C_{10})$heterocyclyl.

Other embodiments of the invention include those compounds of formula I wherein n is two; and each $R^3$ is independently selected from the group consisting of hydrogen and $(C_1$–$C_4)$alkyl; wherein at least one $R^3$ $(C_1$–$C_4)$alkyl group is substituted by $(C_1$–$C_4)$alkoxy, $(C_1$–$C_4)$alkyl-NH—, or $[(C_1$–$C_4)$alkyl]$_2$—N—.

Other embodiments of the invention include those compounds of formula I wherein at least one of said $R^3$ groups is $(C_6$–$C_{10})$aryl, $(C_3$–$C_7)$cycloalkyl, $(C_1$–$C_{10})$heteroaryl or $(C_1$–$C_{10})$heterocyclyl; wherein each of said $R^3$ groups may be optionally substitued by one to three substituents independently selected from the group consisting of halo, hydroxy, amino, —CN, $(C_1$–$C_4)$alkyl, $(C_1$–$C_4)$alkoxy, $(C_1$–$C_4)$alkyl—NH—, $[(C_1$–$C_4)$alkyl]$_2$—N—$(C_6$–$C_{10})$aryl $(C_3$–$C_7)$cycloalkyl, $(C_1$–$C_{10})$heteroaryl and $(C_1$–$C_{10})$ heterocyclyl.

More preferred $R^1$ is $(C_1$–$C_4)$alkoxy$(C_1$–$C_4)$alkyl, most preferably $R^1$ is ethoxyethyl or methoxyethyl.

More preferred compounds of the invention include compounds of formula I, wherein X is —O—, Y is a bond, —O—, —S—, —CH$_2$—, >SO$_2$, —OCH$_2$— or —CH$_2$O—; $R^1$ is $(R^2)_{2n+1}$—$(C)_n$—, n is two; and each $R_2$ is independently selected from the group consisting of hydrogen and $(C_1$–$C_4)$alkyl; wherein at least one $R^3$ $(C_1$–$C_4)$alkyl group is substituted by $(C_1$–$C_4)$alkoxy, $(C_1$–$C_4)$alkyl-NH— or $[(C_1$–$C_4)$alkyl]$_2$—N—.

More preferred compounds of the invention include those wherein X is —O—; A is optionally substituted phenyl; Y is —O—; B is optionally substituted phenyl; G is optionally substituted oxazolyl, isooxazolyl, oxadiazolyl, or pyrazolyl; $R^1$ is $(R^2)_{2n+1}$—$(C)_n$—, n is two; each $R^2$ is independently selected from the group consisting of hydrogen, $(C_1$–$C_4)$ alkyl, $R^3$— and $R^3$—O— and each $R^3$ is independently selected from the group consisting of hydrogen and $(C_1$–$C_4)$ alkyl; wherein one $R^3$ $(C_1$–$C_4)$alkyl group is substituted by $(C_1$–$C_4)$alkoxy; and W is methoxymethyl.

Other more preferred compounds of the invention include those wherein X is —O—; A is optionally substituted phenyl; Y is —O—; B is optionally substituted phenyl; G is optionally substituted oxazolyl, isooxazolyl, oxadiazolyl, or pyrazolyl; $R^1$ is $(R^2)_{2n+1}$—$(C)_n$—, n is two; each $R_2$ is independently selected from the group consisting of hydrogen, $(C_1$–$C_4)$alkyl, $R^3$— and $R^3$—O— and each $R^3$ is independently selected from the group consisting of hydrogen and $(C_1$–$C_4)$alkyl; wherein one $R^3$ $(C_1$–$C_4)$alkyl group is substituted by $(C_1$–$C_4)$alkoxy; and W is optionally substituted cyclopentyl, cyclohexyl, or cycloheptyl.

Other more preferred compounds of the invention include those wherein X is —O—; A is optionally substituted phenyl; Y is —O—; B is optionally substituted phenyl; G is optionally substituted oxazolyl, isooxazolyl, oxadiazolyl, or pyrazolyl; $R^1$ is $(R^2)_{2n+1}$—$(C)_n$—, n is two; each $R^2$ is independently selected from the group consisting of hydrogen, $(C_1$–$C_4)$alkyl, $R^3$— and $R^3$—O— and each $R^3$ is independently selected from the group consisting of hydrogen and $(C_1$–$C_4)$alkyl; wherein one $R^3$ $(C_1$–$C_4)$alkyl group is substituted by $(C_1$–$C_4)$alkoxy; and W is optionally substituted phenyl.

Other more preferred compounds of the invention include those wherein X is —O—; A is optionally substituted phenyl; Y is —O—; B is optionally substituted phenyl; G is optionally substituted oxazolyl, isooxazolyl, oxadiazolyl, or pyrazolyl; $R^1$ is $(R^2)_{2n+1}$—$(C)_n$—, n is two; each $R^2$ is independently selected from the group consisting of hydrogen, $(C_1$–$C_4)$alkyl, $R^3$— and $R^3$—O— and each $R^3$ is independently selected from the group consisting of hydrogen and $(C_1$–$C_4)$alkyl; wherein one $R^3$ $(C_1$–$C_4)$alkyl group is substituted by $(C_1$–$C_4)$alkoxy; and W is optionally substituted pyrazinyl, pyridazinyl, pyridinyl, or pyrimidinyl.

Other more preferred compounds of the invention include those wherein X is —O—; A is optionally substituted phenyl; Y is —O—; B is optionally substituted phenyl; G is optionally substituted oxazolyl, isooxazolyl, oxadiazolyl, or pyrazolyl; $R^1$ is $(R^2)_{2n+1}$—$(C)_n$—, n is two; each $R_2$ is independently selected from the group consisting of hydrogen, $(C_1$–$C_4)$alkyl, $R^3$— and $R^3$—O— and each $R^3$ is independently selected from the group consisting of hydrogen and $(C_1$–$C_4)$alkyl; wherein one $R^3$ $(C_1$–$C_4)$alkyl group is substituted by $(C_1$–$C_4)$alkoxy; and W is optionally substituted morpholinyl, piperazinyl, piperidinyl, pyrrolidinyl, thiomorpholinyl, tetrahydrofuranyl, tetrahydropyranyl, or oxetanyl.

Other compounds of the invention are selected from the group consisting of:

5-(2-Methoxy-ethyl)-5-{4-[4-(4-pyrimidin-4-yl-oxazol-2-yl)-phenoxy]-phenoxy}-pyrimidine-2,4,6-trione;

5-(2-Methoxy-ethyl)-5-{4-[4-(4-pyridazin-3-yl-oxazol-2-yl)-phenoxy]-phenoxy}-pyrimidine-2,4,6-trione;

5-(2-Methoxy-ethyl)-5-{4-[4-(4-pyridazin-4-yl-oxazol-2-yl)-phenoxy]-phenoxy}-pyrimidine-2,4,6-trione;

5-(4-{4-[2-(2-Fluoro-phenyl)-oxazol-5-yl]-phenoxy}-phenoxy)-5-(2-methoxy-ethyl)-pyrimidine-2,4,6-trione;

5-(4-{4-[2-(3-Fluoro-phenyl)-oxazol-5-yl]-phenoxy}-phenoxy)-5-(2-methoxy-ethyl)-pyrimidine-2,4,6-trione;

5-(4-{4-[2-(4-Fluoro-phenyl)-oxazol-5-yl]-phenoxy}-phenoxy)-5-(2-methoxy-ethyl)-pyrimidine-2,4,6-trione;

5-(4-{4-[3-(2-Fluoro-phenyl)-isoxazol-5-yl]-phenoxy}-phenoxy)-5-(2-methoxy-ethyl)-pyrimidine-2,4,6-trione;

5-(4-{4-[3-(3-Fluoro-phenyl)-isoxazol-5-yl]-phenoxy}-phenoxy)-5-(2-methoxy-ethyl)-pyrimidine-2,4,6-trione;

5-(4-{4-[3-(4-Fluoro-phenyl)-isoxazol-5-yl]-phenoxy}-phenoxy)-5-(2-methoxy-ethyl)-pyrimidine-2,4,6-trione;

5-(4-{4-[3-(2-Cyano-phenyl)-isoxazol-5-yl]-phenoxy}-phenoxy)-5-(2-methoxy-ethyl)-pyrimidine-2,4,6-trione;

5-(4-{4-[3-(3-Cyano-phenyl)-isoxazol-5-yl]-phenoxy}-phenoxy)-5-(2-methoxy-ethyl)-pyrimidine-2,4,6-trione;

5-(4-{4-[3-(4-Cyano-phenyl)-isoxazol-5-yl]-phenoxy}-phenoxy)-5-(2-methoxy-ethyl)-pyrimidine-2,4,6-trione;

5-(2-Methoxy-ethyl)-5-{4-[4-(3-pyrimidin-2-yl-isoxazol-5-yl)-phenoxy]-phenoxy}-pyrimidine-2,4,6-trione;

5-(2-Methoxy-ethyl)-5-{4-[4-(3-pyrimidin-4-yl-isoxazol-5-yl)-phenoxy]-phenoxy}-pyrimidine-2,4,6-trione;

5-(2-Methoxy-ethyl)-5-{4-[4-(3-pyrimidin-5-yl-isoxazol-5-yl)-phenoxy]-phenoxy}-pyrimidine-2,4,6-trione;

5-(4-{4-[2-(2-Cyano-phenyl)-oxazol-5-yl]-phenoxy}-phenoxy)-5-(2-methoxy-ethyl)-pyrimidine-2,4,6-trione;

5-(4-{4-[2-(3-Cyano-phenyl)-oxazol-5-yl]-phenoxy}-phenoxy)-5-(2-methoxy-ethyl)-pyrimidine-2,4,6-trione;

5-(4-{4-[2-(4-Cyano-phenyl)-oxazol-5-yl]-phenoxy}-phenoxy)-5-(2-methoxy-ethyl)-pyrimidine-2,4,6-trione;

5-(2-Methoxy-ethyl)-5-{4-[4-(2-pyrimidin-2-yl-oxazol-5-yl)-phenoxy]-phenoxy}-pyrimidine-2,4,6-trione;

5-(2-Methoxy-ethyl)-5-{4-[4-(2-pyrimidin-4-yl-oxazol-5-yl)-phenoxy]-phenoxy}-pyrimidine-2,4,6-trione;

5-(2-Methoxy-ethyl)-5-{4-[4-(2-pyrimidin-5-yl-oxazol-5-yl)-phenoxy]-phenoxy}-pyrimidine-2,4,6-trione;

5-(4-{4-[5-(2-Fluoro-phenyl)-oxazol-2-yl]-phenoxy}-phenoxy)-5-(2-methoxy-ethyl)-pyrimidine-2,4,6-trione;

5-(4-{4-[5-(3-Fluoro-phenyl)-oxazol-2-yl]-phenoxy}-phenoxy)-5-(2-methoxy-ethyl)-pyrimidine-2,4,6-trione;

5-(4-{4-[5-(4-Fluoro-phenyl)-oxazol-2-yl]-phenoxy}-phenoxy)-5-(2-methoxy-ethyl)-pyrimidine-2,4,6-trione;

5-(4-{4-[5-(2-Cyano-phenyl)-oxazol-2-yl]-phenoxy}-phenoxy)-5-(2-methoxy-ethyl)-pyrimidine-2,4,6-trione;

5-(4-{4-[5-(3-Cyano-phenyl)-oxazol-2-yl]-phenoxy}-phenoxy)-5-(2-methoxy-ethyl)-pyrimidine-2,4,6-trione;

5-(4-{4-[5-(4-Cyano-phenyl)-oxazol-2-yl]-phenoxy}-phenoxy)-5-(2-methoxy-ethyl)-pyrimidine-2,4,6-trione;

5-(2-Methoxy-ethyl)-5-{4-[4-(5-pyrimidin-2-yl-oxazol-2-yl)-phenoxy]-phenoxy}-pyrimidine-2,4,6-trione;

5-(2-Methoxy-ethyl)-5-{4-[4-(5-pyrimidin-4-yl-oxazol-2-yl)-phenoxy]-phenoxy}-pyrimidine-2,4,6-trione;

5-(2-Methoxy-ethyl)-5-{4-[4-(5-pyrimidin-5-yl-oxazol-2-yl)-phenoxy]-phenoxy}-pyrimidine-2,4,6-trione;

5-(2-Ethoxy-ethyl)-5-{4-[4-(4-pyrimidin-2-yl-oxazol-2-yl)-phenoxy]-phenoxy}-pyrimidine-2,4,6-trione;

5-{4-[4-(4-Pyrimidin-2-yl-oxazol-2-yl)-phenoxy]-phenoxy}-5-(tetrahydro-furan-2-ylmethyl)-pyrimidine-2,4,6-trione;

5-{4-[4-(4-Pyrimidin-2-yl-oxazol-2-yl)-phenoxy]-phenoxy}-5-(tetrahydro-pyran-2-ylmethyl)-pyrimidine-2,4,6-trione;

(2,4,6-Trioxo-5-{4-[4-(4-pyrimidin-2-yl-oxazol-2-yl)-phenoxy]-phenoxy}-hexahydro-pyrimidin-5-yl)-acetic acid;

(2,4,6-Trioxo-5-{4-[4-(4-pyrimidin-2-yl-oxazol-2-yl)-phenoxy]-phenoxy}-hexahydro-pyrimidin-5-yl)-propionic acid;

5-(2-Methoxy-ethyl)-5-{4-[4-(4-phenyl-oxazol-2-yl)-phenoxy]-phenoxy}pyrimidine-2,4,6-trione;

5-(2-Ethoxy-ethyl)-5-{4-[4-(4-phenyl-oxazol-2-yl)-phenoxy]-phenoxy}-pyrimidine-2,4,6-trione;

5-(4-{4-[4-(2-Fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(2-fluoro-phenyl)-oxazol-2-yl]-phenoxy}-phenoxy)-pyrimidine-2,4,6-trione;

5-(4-{4-[4-(3-Fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(3-fluoro-phenyl)-oxazol-2-yl]-phenoxy}-phenoxy)-pyrimidine-2,4,6-trione;

5-(2-Benzyloxy-ethyl)-5-(4-{4-[4-(3-fluoro-phenyl)-oxazol-2-yl]-phenoxy}-phenoxy)-pyrimidine-2,4,6-trione;

5-(4-{4-[4-(3-Fluoro-phenyl)-oxazol-2-yl]-phenoxy}-phenoxy)-5-(2-hydroxy-ethyl)-pyrimidine-2,4,6-trione;

5-(4-{4-[4-(4-Fluoro-phenyl)-oxazol-2-yl]-phenoxy}-phenoxy)-5-methoxymethyl-pyrimidine-2,4,6-trione;

5-(4-{4-[4-(4-Fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(4-fluoro-phenyl)-oxazol-2-yl]-phenoxy}-phenoxy)-pyrimidine-2,4,6-trione;

2-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

2-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

3-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

3-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

4-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

4-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

5-(2-Methoxy-ethyl)-5-{4-[4-(4-pyridin-2-yl-oxazol-2-yl)-phenoxy]-phenoxy}-pyrimidine-2,4,6-trione;

5-(2-Ethoxy-ethyl)-5-{4-[4-(4-pyridin-2-yl-oxazol-2-yl)-phenoxy]-phenoxy}-pyrimidine-2,4,6-trione;

5-(2-Methoxy-ethyl)-5-{4-[4-(4-pyridin-3-yl-oxazol-2-yl)-phenoxy]-phenoxy}-pyrimidine-2,4,6-trione;

5-(2-Ethoxy-ethyl)-5-{4-[4-(4-pyridin-3-yl-oxazol-2-yl)-phenoxy]-phenoxy}-pyrimidine-2,4,6-trione;

5-(2-Methoxy-ethyl)-5-{4-[4-(4-pyridin-4-yl-oxazol-2-yl)-phenoxy]-phenoxy}-pyrimidine-2,4,6-trione;

5-(2-Ethoxy-ethyl)-5-{4-[4-(4-pyridin-4-yl-oxazol-2-yl)-phenoxy]-phenoxy}-pyrimidine-2,4,6-trione;

5-(2-Methoxy-ethyl)-5-{4-[4-(4-pyrimidin-2-yl-oxazol-2-yl)-phenoxy]-phenoxy}-pyrimidine-2,4,6-trione;

5-(2-Methoxy-ethyl)-5-{4-[4-(4-pyrimidin-5-yl-oxazol-2-yl)-phenoxy]-phenoxy}-pyrimidine-2,4,6-trione;

5-(2-Methoxy-ethyl)-5-{4-[4-(4-pyrazin-2-yl-oxazol-2-yl)-phenoxy]-phenoxy}-pyrimidine-2,4,6-trione;

5-(2-Methoxy-ethyl)-5-{4-[4-(5-phenyl-oxazol-2-yl)-phenoxy]-phenoxy}pyrimidine-2,4,6-trione;

5-(2-Ethoxy-ethyl)-5-{4-[4-(5-phenyl-oxazol-2-yl)-phenoxy]-phenoxy}pyrimidine-2,4,6-trione;

5-(2-Methoxy-ethyl)-5-{4-[4-(2-phenyl-oxazol-5-yl)-phenoxy]-phenoxy}pyrimidine-2,4,6-trione; and 5-(2-Ethoxy-ethyl)-5-{4-[4-(2-phenyl-oxazol-5-yl)-phenoxy]-phenoxy}pyrimidine-2,4,6-trione; or the pharmaceutically acceptable salts thereof.

Other compounds of the invention are selected from the group consisting of:

5-(4-{4-[3-(2-Fluoro-phenyl)-isoxazol-5-yl]-phenoxy}-phenoxy)-5-(2-methoxy-ethyl)-pyrimidine-2,4,6-trione;

5-(4-{4-[3-(3-Fluoro-phenyl)-isoxazol-5-yl]-phenoxy}-phenoxy)-5-(2-methoxy-ethyl)-pyrimidine-2,4,6-trione;

5-(4-{4-[3-(4-Fluoro-phenyl)-isoxazol-5-yl]-phenoxy}-phenoxy)-5-(2-methoxy-ethyl)-pyrimidine-2,4,6-trione;
5-(4-{4-[3-(2-Cyano-phenyl)-isoxazol-5-yl]-phenoxy}-phenoxy)-5-(2-methoxy-ethyl)-pyrimidine-2,4,6-trione;
5-(4-{4-[3-(3-Cyano-phenyl)-isoxazol-5-yl]-phenoxy}-phenoxy)-5-(2-methoxy-ethyl)-pyrimidine-2,4,6-trione;
5-(4-{4-[3-(4-Cyano-phenyl)-isoxazol-5-yl]-phenoxy}-phenoxy)-5-(2-methoxy-ethyl)-pyrimidine-2,4,6-trione;
5-(2-Methoxy-ethyl)-5-{4-[4-(3-pyrimidin-2-yl-isoxazol-5-yl)-phenoxy]-phenoxy}-pyrimidine-2,4,6-trione;
5-(2-Methoxy-ethyl)-5-{4-[4-(3-pyrimidin-4-yl-isoxazol-5-yl)-phenoxy]-phenoxy}-pyrimidine-2,4,6-trione;
5-(2-Methoxy-ethyl)-5-{4-[4-(3-pyrimidin-5-yl-isoxazol-5-yl)-phenoxy]-phenoxy}-pyrimidine-2,4,6-trione;
5-(2-Ethoxy-ethyl)-5-{4-[4-(3-phenyl-isoxazol-5-yl)-phenoxy]-phenoxy}-pyrimidine-2,4,6-trione; and
5-(2-Methoxy-ethyl)-5-{4-[4-(3-phenyl-isoxazol-5-yl)-phenoxy]-phenoxy}-pyrimidine-2,4,6-trione; or
the pharmaceutically acceptable salts thereof.

Other compounds of the invention are selected from the group consisting of:
5-(4-{4-[5-(2-Fluoro-phenyl)-[1,3,4]oxadiazol-2-yl]-phenoxy}-phenoxy)-5-(2-methoxy-ethyl)-pyrimidine-2,4,6-trione;
5-(4-{4-[5-(3-Fluoro-phenyl)-[1,3,4]oxadiazol-2-yl]-phenoxy}-phenoxy)-5-(2-methoxy-ethyl)-pyrimidine-2,4,6-trione;
5-(4-{4-[5-(4-Fluoro-phenyl)-[1,3,4]oxadiazol-2-yl]-phenoxy}-phenoxy)-5-(2-methoxy-ethyl)-pyrimidine-2,4,6-trione;
5-(4-{4-[5-(2-Cyano-phenyl)-[1,3,4]oxadiazol-2-yl]-phenoxy}-phenoxy)-5-(2-methoxy-ethyl)-pyrimidine-2,4,6-trione;
5-(4-{4-[5-(3-Cyano-phenyl)-[1,3,4]oxadiazol-2-yl]-phenoxy}-phenoxy)-5-(2-methoxy-ethyl)-pyrimidine-2,4,6-trione;
5-(4-{4-[5-(4-Cyano-phenyl)-[1,3,4]oxadiazol-2-yl]-phenoxy}-phenoxy)-5-(2-methoxy-ethyl)-pyrimidine-2,4,6-trione;
5-(2-Methoxy-ethyl)-5-{4-[4-(5-pyrimidin-2-yl-[1,3,4]oxadiazol-2-yl)-phenoxy]-phenoxy}-pyrimidine-2,4,6-trione;
5-(2-Methoxy-ethyl)-5-{4-[4-(5-pyrimidin-4-yl-[1,3,4]oxadiazol-2-yl)-phenoxy]-phenoxy}-pyrimidine-2,4,6-trione;
5-(2-Methoxy-ethyl)-5-{4-[4-(5-pyrimidin-5-yl-[1,3,4]oxadiazol-2-yl)-phenoxy]-phenoxy}-pyrimidine-2,4,6-trione;
5-(4-{4-[5-(2-Fluoro-phenyl)-[1,2,4]oxadiazol-3-yl]-phenoxy}-phenoxy)-5-(2-methoxy-ethyl)-pyrimidine-2,4,6-trione;
5-(4-{4-[5-(3-Fluoro-phenyl)-[1,2,4]oxadiazol-3-yl]-phenoxy}-phenoxy)-5-(2-methoxy-ethyl)-pyrimidine-2,4,6-trione;
5-(4-{4-[5-(4-Fluoro-phenyl)-[1,2,4]oxadiazol-3-yl]-phenoxy}-phenoxy)-5-(2-methoxy-ethyl)-pyrimidine-2,4,6-trione;
5-(4-{4-[5-(2-Cyano-phenyl)-[1,2,4]oxadiazol-3-yl]-phenoxy}-phenoxy)-5-(2-methoxy-ethyl)-pyrimidine-2,4,6-trione;
5-(4-{4-[5-(3-Cyano-phenyl)-[1,2,4]oxadiazol-3-yl]-phenoxy}-phenoxy)-5-(2-methoxy-ethyl)-pyrimidine-2,4,6-trione;
5-(4-{4-[5-(4-Cyano-phenyl)-[1,2,4]oxadiazol-3-yl]-phenoxy}-phenoxy)-5-(2-methoxy-ethyl)-pyrimidine-2,4,6-trione;
5-(2-Methoxy-ethyl)-5-{4-[4-(5-pyrimidin-2-yl-[1,2,4]oxadiazol-3-yl)-phenoxy]-phenoxy}-pyrimidine-2,4,6-trione;
5-(2-Methoxy-ethyl)-5-{4-[4-(5-pyrimidin-4-yl-[1,2,4]oxadiazol-3-yl)-phenoxy]-phenoxy}-pyrimidine-2,4,6-trione;
5-(2-Methoxy-ethyl)-5-{4-[4-(5-pyrimidin-5-yl-[1,2,4]oxadiazol-3-yl)-phenoxy]-phenoxy}-pyrimidine-2,4,6-trione;
5-(2-Methoxy-ethyl)-5-{4-[4-(3-phenyl-[1,2,4]oxadiazol-5-yl)-phenoxy]-phenoxy}-pyrimidine-2,4,6-trione;
5-(2-Ethoxy-ethyl)-5-{4-[4-(3-phenyl-[1,2,4]oxadiazol-5-yl)-phenoxy]-phenoxy}-pyrimidine-2,4,6-trione;
5-(2-Ethoxy-ethyl)-5-(4-{4-[3-(3-fluoro-phenyl)-[1,2,4]oxadiazol-5-yl]-phenoxy}-phenoxy)-pyrimidine-2,4,6-trione;
5-(4-{4-[3-(3-Fluoro-phenyl)-[1,2,4]oxadiazol-5-yl]-phenoxy}-phenoxy)-5-(2-methoxy-ethyl)-pyrimidine-2,4,6-trione;
5-(2-Methoxy-ethyl)-5-{4-[4-(3-o-tolyl-[1,2,4]oxadiazol-5-yl)-phenoxy]-phenoxy}-pyrimidine-2,4,6-trione;
5-(2-Ethoxy-ethyl)-5-{4-[4-(3-o-tolyl-[1,2,4]oxadiazol-5-yl)-phenoxy]-phenoxy}-pyrimidine-2,4,6-trione;
5-(2-Ethoxy-ethyl)-5-{4-[4-(3-m-tolyl-[1,2,4]oxadiazol-5-yl)-phenoxy]-phenoxy}-pyrimidine-2,4,6-trione;
5-(2-Methoxy-ethyl)-5-{4-[4-(3-m-tolyl-[1,2,4]oxadiazol-5-yl)-phenoxy]-phenoxy}-pyrimidine-2,4,6-trione;
5-(4-{4-[3-(2–Chloro-phenyl)-[1,2,4]oxadiazol-5-yl]-phenoxy}-phenoxy)-5-(2-methoxy-ethyl)-pyrimidine-2,4,6-trione;
5-(4-{4-[3-(2-Chloro-phenyl)-[1,2,4]oxadiazol-5-yl]-phenoxy}-phenoxy)-5-(2-ethoxy-ethyl)-pyrimidine-2,4,6-trione;
5-(4-{4-[3-(2-Fluoro-phenyl)-[1,2,4]oxadiazol-5-yl]-phenoxy}-phenoxy)-5-(2-methoxy-ethyl)-pyrimidine-2,4,6-trione;
5-(2-Ethoxy-ethyl)-5-(4-{4-[3-(2-fluoro-phenyl)-[1,2,4]oxadiazol-5-yl]-phenoxy}-phenoxy)-pyrimidine-2,4,6-trione;
5-(4-{4-[3-(3–Chloro-phenyl)-[1,2,4]oxadiazol-5-yl]-phenoxy}-phenoxy)-5-(2-ethoxy-ethyl)-pyrimidine-2,4,6-trione;
5-(2-Ethoxy-ethyl)-5-{4-[4-(3-pyridin-2-yl-[1,2,4]oxadiazol-5-yl)-phenoxy]-phenoxy}-pyrimidine-2,4,6-trione;
5-(2-Ethoxy-ethyl)-5-{4-[4-(3-pyridin-3-yl-[1,2,4]oxadiazol-5-yl)-phenoxy]-phenoxy}-pyrimidine-2,4,6-trione;
5-(2-Ethoxy-ethyl)-5-{4-[4-(3-pyridin-4-yl-[1,2,4]oxadiazol-5-yl)-phenoxy]-phenoxy}-pyrimidine-2,4,6-trione;
5-(2-Ethoxy-ethyl)-5-{4-[4-(3-pyrazin-2-yl-[1,2,4]oxadiazol-5-yl)-phenoxy]-phenoxy}-pyrimidine-2,4,6-trione;
5-(2-Methoxy-ethyl)-5-{4-[4-(3-pyrazin-2-yl-[1,2,4]oxadiazol-5-yl)-phenoxy]-phenoxy}-pyrimidine-2,4,6-trione;
5-(2Benzyloxy-ethyl)-5-(4-{4-[3-(2-fluoro-phenyl)-[1,2,4]-oxadiazol-5-yl]-phenoxy}-phenoxy)-pyrimidine-2,4,6-trione;
5-(4-{4-[3-(4-Fluoro-phenyl)-[1,2,4]oxadiazol-5-yl]-phenoxy}-phenoxy)-5-(2-methoxy-ethyl)-pyrimidine-2,4,6-trione;
5-(2-Ethoxy-ethyl)-5-(4-{4-[3-(4-fluoro-phenyl)-[1,2,4]oxadiazol-5-yl]-phenoxy}-phenoxy)-pyrimidine-2,4,6-trione;
5-(4-{4-[3-(2-Fluoro-phenyl)-[1,2,4]oxadiazol-5-yl]-phenoxy}-phenoxy)-5-(2-hydroxy-ethyl)-pyrimidine-2,4,6-trione;

5-(4-{4-[3-(3-Fluoro-pyridin-2-yl)-[1,2,4]oxadiazol-5-yl]-phenoxy}-phenoxy)-5-(2-methoxy-ethyl)-pyrimidine-2,4,6-trione;

5-(2-Ethoxy-ethyl)-5-(4-{4-[3-(3-fluoro-pyridin-2-yl)-[1,2,4]oxadiazol-5-yl]-phenoxy}-phenoxy)-pyrimidine-2,4,6-trione;

[5-(4-{4-[3-(2-Fluoro-phenyl)-[1,2,4]oxadiazol-5-yl]-phenoxy}-phenoxy)-2,4,6-trioxo-hexahydro-pyrimidin-5-yl]-acetic acid;

5-(2-Ethoxy-ethyl)-5-{4-[4-(3-pyridazin-3-yl-[1,2,4]oxadiazol-5-yl)-phenoxy]-phenoxy}-pyrimidine-2,4,6-trione;

5-(2-Ethoxy-ethyl)-5-{4-[4-(5-phenyl-[1,3,4]oxadiazol-2-yl)-phenoxy]-phenoxy}-pyrimidine-2,4,6-trione;

5-(2-Methoxy-ethyl)-5-{4-[4-(5-phenyl-[1,2,4]oxadiazol-3-yl)-phenoxy]-phenoxy}-pyrimidine-2,4,6-trione; and 5-(2-Ethoxy-ethyl)-5-{4-[4-(5-phenyl-[1,2,4]oxadiazol-3-yl)-phenoxy]-phenoxy}-pyrimidine-2,4,6-trione; or the pharmaceutically acceptable salts thereof.

Other compounds of the invention are selected from the group consisting of:

5-(4-{4-[1-(4-Chloro-phenyl)-1H-pyrazol-3-yl]-phenoxy}-phenoxy)-5-(2-methoxy-ethyl)-pyrimidine-2,4,6-trione;

5-(2-Methoxy-ethyl)-5-{4-[4-(1-p-tolyl-1H-pyrazol-3-yl)-phenoxy]-phenoxy}-pyrimidine-2,4,6-trione;

5-(2-Methoxy-ethyl)-5-{4-[4-(1-(4-fluorophenyl)-1H-pyrazol-3-yl)-phenoxy]-phenoxy}-pyrimidine-2,4,6-trione;

5-(2-Ethoxy-ethyl)-5-{4-[4-(1-(4-fluorophenyl)-1H-pyrazol-3-yl)-phenoxy]-phenoxy}-pyrimidine-2,4,6-trione;

5-(2-Methoxy-ethyl)-5-{4-[4-(1-(3-fluorophenyl)-1H-pyrazol-3-yl)-phenoxy]-phenoxy}-pyrimidine-2,4,6-trione;

5-(2-Ethoxy-ethyl)-5-{4-[4-(1-(3-fluorophenyl)-1H-pyrazol-3-yl)-phenoxy]-phenoxy}-pyrimidine-2,4,6-trione;

5-(2-Methoxy-ethyl)-5-{4-[4-(3-(3-fluorophenyl)-1H-pyrazol-5-yl)-phenoxy]-phenoxy}-pyrimidine-2,4,6-trione; and 5-(2-Ethoxy-ethyl)-5-{4-[4-(3-(3-fluorophenyl)-1H-pyrazol-5-yl)-phenoxy]-phenoxy}-pyrimidine-2,4,6-trione; or the pharmaceutically acceptable salts thereof.

Preferred compounds of the invention are selected from the group consisting of:

5-(4-{4-[4-(2-Fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(2-fluoro-phenyl)-oxazol-2-yl]-phenoxy}-phenoxy)-pyrimidine-2,4,6-trione;

5-(4-{4-[4-(4-Fluoro-phenyl)-oxazol-2-yl]-phenoxy}-phenoxy)-5-methoxymethyl-pyrimidine-2,4,6-trione;

5-(4-{4-[4-(4-Fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(4-fluoro-phenyl)-oxazol-2-yl]-phenoxy}-phenoxy)-pyrimidine-2,4,6-trione;

2-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

2-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

4-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

4-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

5-(2-Methoxy-ethyl)-5-{4-[4-(4-pyridin-2-yl-oxazol-2-yl)-phenoxy]-phenoxy}-pyrimidine-2,4,6-trione;

5-(2-Ethoxy-ethyl)-5-{4-[4-(4-pyridipyridin-2-yl-oxazol-2-yl)-phenoxy]-phenoxy}-pyrimidine-2,4,6-trione;

5-(2-Methoxy-ethyl)-5-{4-[4-(4-pyridin-4-yl-oxazol-2-yl)-phenoxy]-phenoxy}-pyrimidine-2,4,6-trione;

5-(2-Methoxy-ethyl)-5-{4-[4-(5-phenyl-oxazol-2-yl)-phenoxy]-phenoxy}pyrimidine-2,4,6-trione;

5-(2-Methoxy-ethyl)-5-{4-[4-(2-phenyl-oxazol-5-yl)-phenoxy]-phenoxy}pyrimidine-2,4,6-trione;

5-(2-Ethoxy-ethyl)-5-{4-[4-(2-phenyl-oxazol-5-yl)-phenoxy]-phenoxy}pyrimidine-2,4,6-trione;

5-(4-{4-[3-(2-Chloro-phenyl)-[1,2,4]oxadiazol-5-yl]-phenoxy}-phenoxy)-5-(2-methoxy-ethyl)-pyrimidine-2,4,6-trione;

5-(4-{4-[3-(2-Fluoro-phenyl)-[1,2,4]oxadiazol-5-yl]-phenoxy}-phenoxy)-5-(2-methoxy-ethyl)-pyrimidine-2,4,6-trione;

5-(2-Ethoxy-ethyl)-5-(4-{4-[3-(2-fluoro-phenyl)-[1,2,4]oxadiazol-5-yl]-phenoxy}-phenoxy)-pyrimidine-2,4,6-trione;

5-(4-{4-[3-(3-Chloro-phenyl)-[1,2,4]oxadiazol-5-yl]-phenoxy}-phenoxy)-5-(2-ethoxy-ethyl)-pyrimidine-2,4,6-trione;

5-(2-Ethoxy-ethyl)-5-{4-[4-(3-pyridin-3-yl-[1,2,4]oxadiazol-5-yl)-phenoxy]-phenoxy}-pyrimidine-2,4,6-trione;

5-(2-Ethoxy-ethyl)-5-{4-[4-(3-pyridin-4-yl-[1,2,4]oxadiazol-5-yl)-phenoxy]-phenoxy}-pyrimidine-2,4,6-trione;

5-(2-Methoxy-ethyl)-5-{4-[4-(1-(4-fluorophenyl)-1H-pyrazol-3-yl)-phenoxy]-phenoxy}-pyrimidine-2,4,6-trione;

5-(2-Ethoxy-ethyl)-5-{4-[4-(1-(4-fluorophenyl)-1H-pyrazol-3-yl)-phenoxy]-phenoxy}-pyrimidine-2,4,6-trione;

5-(2-Methoxy-ethyl)-5-{4-[4-(1-(3-fluorophenyl)-1H-pyrazol-3-yl)-phenoxy]-phenoxy}-pyrimidine-2,4,6-trione; and 5-(2-Ethoxy-ethyl)-5-{4-[4-(1-(3-fluorophenyl)-1H-pyrazol-3-yl)-phenoxy]-phenoxy}-pyrimidine-2,4,6-trione; or the pharmaceutically acceptable salts thereof.

The present invention also relates to a pharmaceutical composition for the treatment of a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by metalloproteinase activity in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of a condition which can be treated by the inhibition of matrix metalloproteinases in a mammal, including a human, comprising an amount of a compound of formula I effective in such treatment and a pharmaceutically acceptable carrier.

The present invention also relates to a method for the inhibition of matrix metalloproteinases in a mammal, including a human, comprising administering to said mammal an effective amount of a compound of formula I.

The present invention also relates to a method for treating a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by matrix metalloproteinase activity in a mammal, including a human, comprising administering to said mammal an amount of a compound of formula I or a pharmaceutically acceptable salt thereof effective in treating such a condition.

The present invention also relates to a method for the inhibition of matrix metalloproteinases or other metalloproteinases involved in matrix degradation, in a mammal, including a human, comprising administering to said mammal an effective amount of a compound of formula I or a pharmaceutically acceptable salt thereof.

The present inventors have also discovered that it is possible to identify inhibitors of formula I with differential metalloprotease activity (preferably MMP-13 inhibitory activity). One group of preferred inhibitors of formula I the inventors have been able to identify include those which selectively inhibit MMP-13 preferentially over MMP-1. The compounds of the invention also possess selectivity over a related group of enzymes known as reprolysins, such as TACE and aggrecanase. Another group of preferred inhibitors of formula I the inventors have been able to identify include those which selectively inhibit MMP-13 preferentially over MMP-1 and MMP-14. Another group of preferred inhibitors of formula I the inventors have been able to identify include those which selectively inhibit MMP-13 preferentially over MMP-1 and 12. Another group of preferred inhibitors of formula I the inventors have been able to identify include those which selectively inhibit MMP-13 preferentially over MMP-1, 12 and 14. Another group of preferred inhibitors of formula I the inventors have been able to identify include those which selectively inhibit MMP-13 preferentially over MMP-1, 2, 3, 7, 9 and 14. Most preferred compounds of the invention selectively inhibit MMP-13 preferentially over any two or more of MMP-1, 2, 3, 7, 9, 12 and 14 and mammalian reprolysins.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione exhibits: i) a ratio of MMP-1 $IC_{50}$/MMP-13 $IC_{50}$ of about 50, and ii) a ratio of MMP-14 $IC_{50}$/MMP-13 $IC_{50}$ of about 50; wherein said MMP-1 $IC_{50}$ is measured by a recombinant MMP-1 assay; wherein each of said MMP-13 $IC_{50}$ is measured by a recombinant MMP-13 assay; and wherein said MMP-14 $IC_{50}$ is measured by a recombinant MMP-14 assay.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione additionally exhibits iii) a ratio of MMP-12 $IC_{50}$/MMP-13 $IC_{50}$ of about 50; wherein said MMP-12 $IC_{50}$ is measured by a recombinant MMP-12 assay; and wherein said MMP-13 $IC_{50}$ is measured by a recombinant MMP-13 assay.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione additionally exhibits iv) a ratio of MMP-2 $IC_{50}$/MMP-13 $IC_{50}$ of about 50, and v) a ratio of MMP-3 $IC_{50}$/MMP-13 $IC_{50}$ of about 50; vi) a ratio of MMP-7 $IC_{50}$/MMP-13 $IC_{50}$ of about 50, and vii) a ratio of MMP-9 $IC_{50}$/MMP-13 $IC_{50}$ of about 50; wherein said MMP-2 $IC_{50}$ is measured by a recombinant MMP-2 assay; wherein said MMP-3 $IC_{50}$ is measured by a recombinant MMP-3 assay; wherein said MMP-7 $IC_{50}$ is measured by a recombinant MMP-7 assay; wherein said MMP-9 $IC_{50}$ is measured by a recombinant MMP-9 assay; and each of said MMP-13 $IC_{50}$ is measured by a recombinant MMP-13 assay.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione exhibits an MMP-13 $IC_{50}$ of less than about 100 nM, preferably of less than about 50 nM; more preferably of less than about 20 nM.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Connective tissue disorders" as used herein refers to disorders such as degenerative cartilage loss following traumatic joint injury, osteoarthritis, osteoporosis, Paget's disease, loosening of artificial joint implants, periodontal disease and gingivitis.

"Destruction of articular cartilage" as used herein refers to connective tissue disorders resulting in articular cartilage destruction, preferably joint injury, reactive arthritis, acute pyrophosphate arthritis (pseudogout), psoriatic arthritis, or juvenile rheumatoid arthritis, more preferably osteoarthritis.

"Inflammatory disorders" as used herein refers to disorders such as rheumatoid arthritis, ankylosing spondylitis, psoriatic arthritis, psoriasis, chondrocalcinosis, gout, inflammatory bowel disease, ulcerative colitis, Crohn's disease. fibromyalgia and cachexia.

"Immunology/allergy disorders" as used herein refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein refers to disorders such as septic arthritis, AIDS, fever; Prion diseases, myasthenia gravis, Malaria, sepsis, hemodynamic shock and septic shock.

"Respiratory diseases" as used herein refers to disorders such as chronic obstructive pulmonary disease (including emphysema), acute respiratory distress syndrome, asthma, hyperoxic alveolar injury and idiopathic pulmonary fibrosis and other fibrotic lung diseases.

"Cardiovascular diseases" as used herein refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases" as used herein refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including "Age Related Macular Degeneration (ARMD) including both wet and dry forms), proliferative vitreoretinopathy and retinopathy of prematurity.

"Metabolic diseases" as used herein refers to disorders such as diabetes (including non-insulin dependent diabetes mellitus, diabetic retinopathy, insulin resistance, diabetic ulceration).

"Central Nervous System" (CNS) disorders as used herein refers to disorders such as head trauma, spinal cord injury, Inflammatory diseases of the central nervous system, neurodegenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases" as used herein refers to disorders such as nephrotic syndromes such as glomerulonephritis and glomerular disease of the kidney, proteinuria, cirrhosis of the liver and interstitial nephritis.

"Reproductive Health disorders" as used herein refers to disorders such as endometriosis, contraception (male/female), dysmenorrhea, dysfunctional uterine bleeding, premature rupture of fetal membranes and abortifactant.

"Gastric disorders" as used herein refers to disorders such as colonic anastomosis and gastric ulcers.

"Skin disorders" as used herein refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers" as used herein refers to disorders such as solid tumor cancer including colon cancer, breast cancer, lung cancer and prostate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney and other urinary tissues, eye brain and central nervous system, thyroid and other endocrine gland, Hodgkin's disease, non-Hodgkin's lymphomas, multiple myeloma and hematopoietic malignancies including leukemias and lymphomas including lymphocytic, granulocytic and monocytic.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently, bonded to the above substituents of formula I through the carbonyl carbon prodrug sidechain. Prodrugs also include dimers of compounds of formula I.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as infliximab, D2E7 and CDP-870) and TNF receptor immunoglobulin molecules (such as etanercept), ICE inhibitors, MEKK1 inhibitors, COX-2 inhibitors such as celecoxib, rofecoxib, valdecoxib and etoricoxib; low dose methotrexate, lefunimide, steroids, glucosamines, chondrosamines/sulfates, gabapentin, A-agonists, IL-1 process and release inhibitors, IL-1 receptor antagonists such as Kineret®, CCR-1 antagonists, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib, etoricoxib and rofecoxib, analgesics, steroids, glucosamines, chondrosamines/sulfates, gabapentin, A-agonists, IL-1 process and release inhibitors, CCR-1 antagonists, LTD-4, LTB-4 and 5-LO inhibitors, p38 kinase inhibitors and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, paclitaxel, docetaxel and alkaloids, such as vincristine and antimetabolites such as methotrexate.

The compounds of the present invention may also be used in combination with cardiovascular agents such as calcium channel blockers (such as amlodipine and nifedipine), lipid lowering agents such as statins (such as lovastatin, atorvastatin, pravastatin and simvastatin), adrenergics such as doxazosin and terazosin; fibrates, beta-blockers, Ace inhibitors (such as captopril, lisinopril, fosinopril, enalapril and quinaprill), Angiotensin-2 receptor antagonists such as losartan and irbesartan; nitrates, CCB's, diuretics such as digitalis and platelet aggregation inhibitors. The compounds of the present invention may also be used in combination with plaque rupture preventitive agents such as statins, zithromax, NSAIDs including aspirin, heparin, urarfarin, abciximab, TPA and platelet Inhibitors. The compounds of the present invention may also be used in combination with stroke treatment agents such as NIF, NHEI's and CCRIR antagonists.

The compounds of the present invention may also be used in combination with CNS agents such as antidepressants (such as sertraline), anti-Parkinsonian drugs (such as deprenyl, carbadopa, L-dopa, dopamine receptor agonists such as ropinirole, pergolide and pramipexole; MAOB inhibitors such as selegiline and rasagiline, catechol-O-methyltrasferase inhibitors such as tolcapone, A-2 inhibitors, dopamine reuptake inhibitors, NMDA antagonists, Nicotine agonists, NK-1 inhibitors, dopamine agonists and inhibitors of neuronal nitric oxide synthase) and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

The compounds of the present invention may also be used in combination with agents for the treatment of respiratory diseases such as PDE-IV inhibitors, steroidals such as fluticasone, triamcinolone, budesonide, budesonide and beclomethasone, anticholinergics such as ipratropium, sympathomimetics such as salmeterol, albuterol and Xopenex, decongestants such as fexofenadine, loratadine and cetirizine; leukotriene antagonists such as zafirlukast and motelukast; and mast cell stabilizers such as zileuton.

The compounds of the present invention may also be used in combination with agents for the treatment of skin disorders such as tretinoin, isotretinoin, steroids such as cortisone and mometasone, antibiotics such as tetracycline, antifungals such as clotrimazole, miconazole and fluconazole and PDE-IV inhibitors.

The compounds of the present invention may also be used in combination with agents for the treatment of diabetes such as insulin, including human or humanized insulin and inhaled insulin, aldose reductase inhibitors, sorbitol dehydrogenase inhibitors, antidiabetic agents such as biguanides such as metformin; glitazones, glycosidase inhibitors such as acarbose, sulfonylureas such as glimepiride and glipizide; and thiazolidinediones such as pioglitazone, rosiglitazone and trogliazone. Preferred combinations are useful for treating the side effects of diabetes such as retinopathy, nephropathy and neuropathy, preferably retinopathy.

DETAILED DESCRIPTION OF THE INVENTION

The following reaction Schemes illustrate the preparation of the compounds of the present invention. Unless otherwise indicated each of X, A, Y, B, G, W, $R^1$, $R^2$, $R^3$, $R^4$, $R^5$, $R^6$, $R^7$, $R^8$, and $R^9$ in the reaction Schemes and the discussion that follows is defined as above.

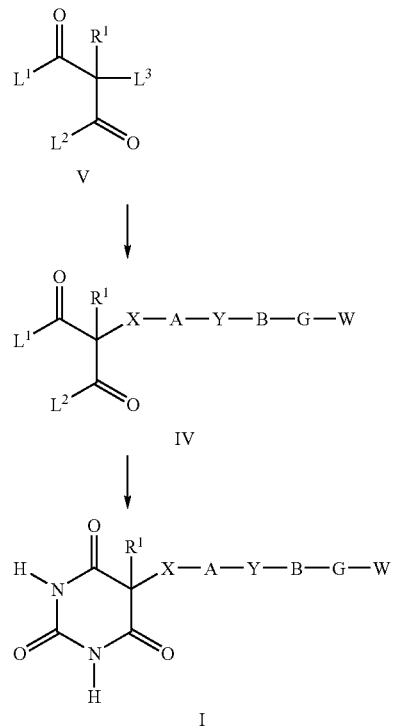

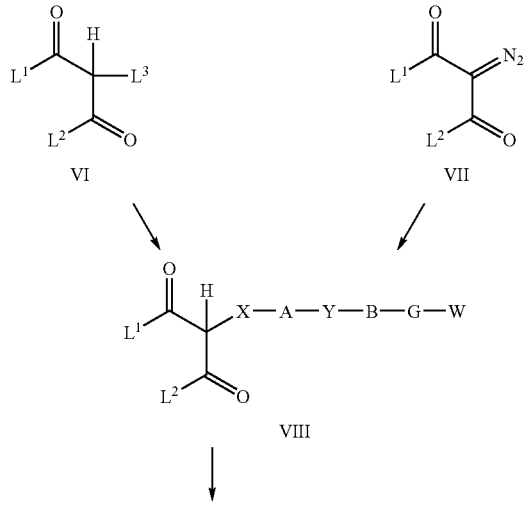

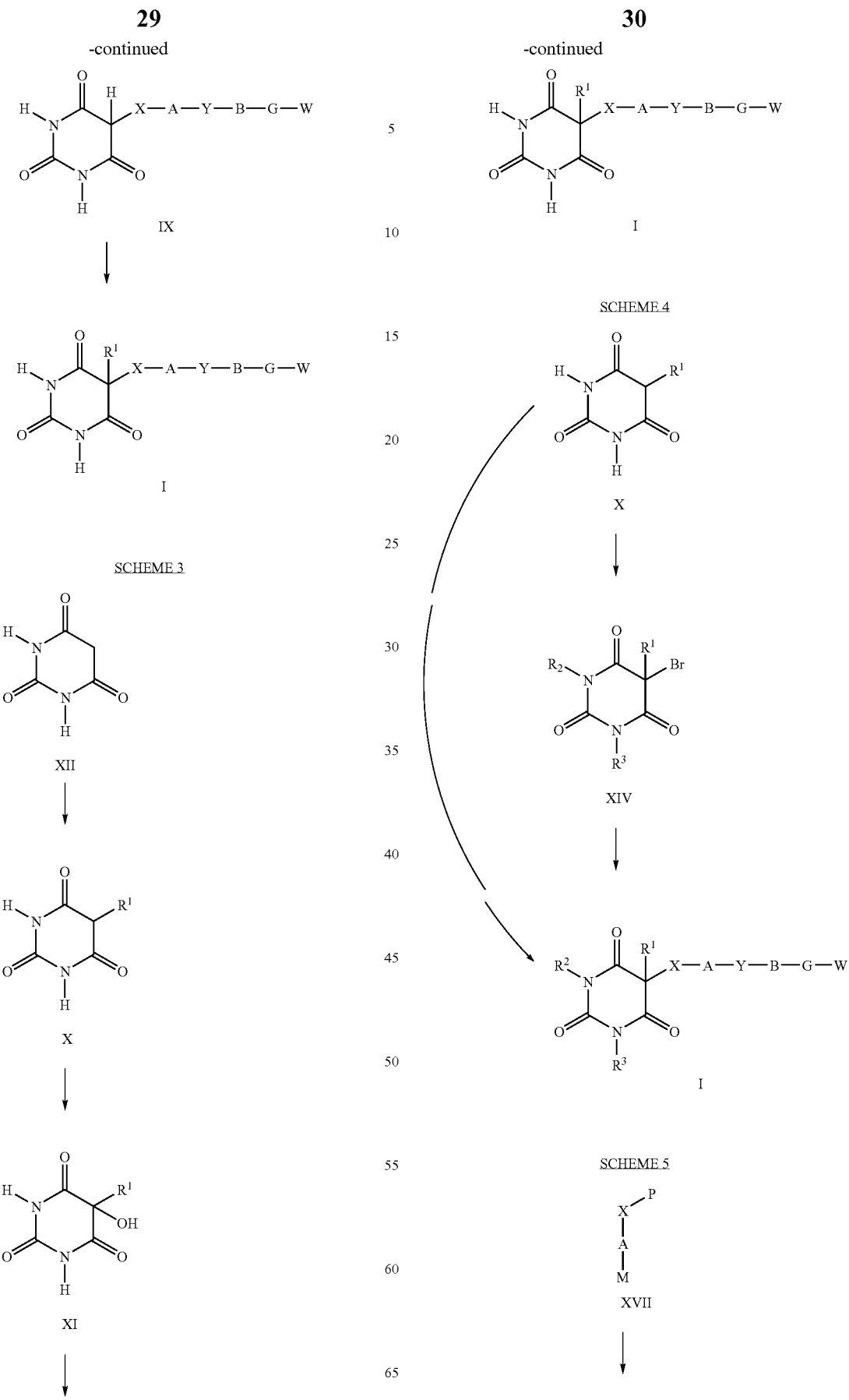

XVI

XV

SCHEME 6

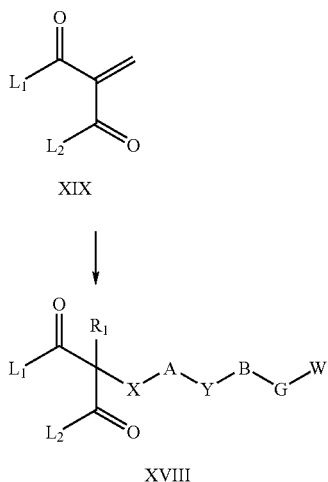

XVIII

Scheme 1 refers to the preparation of compounds of the formula I in a two step synthesis from compounds of the formula V. Referring to Scheme 1, a compound of the formula I is prepared by reacting a compound of the formula IV, wherein $L^1$ and $L^2$ are leaving groups such as methoxy, ethoxy, benzyloxy or chloro, preferably ethoxy, with a urea of the formula III ($H_2NCONH_2$) in the presence of a strong base in a polar solvent. Suitable bases include sodium methoxide, sodium ethoxide and magnesium methoxide, preferably sodium ethoxide. Suitable solvents include alcohols (such as ethanol) or tetrahydrofuran, preferably absolute ethanol. The aforesaid reaction can be conducted at a temperature of about 20° C. to about 90° C., preferably about 50° C. to about 65° C. The aforesaid reaction can be conducted for a time period between about 15 minutes to about 16 hours.

The compound of formula IV is prepared by reacting a compound of formula V, wherein $L^3$ is a leaving group such as halo, p-tolylsulfonyloxy (OTs) or methylsulfonyloxy (OMs), preferably halo, most preferably chloro or bromo, with a compound of the formula II (i.e., compounds of the formula H—X-A-Y-B-G-W) in the presence of a base in a polar solvent. Suitable solvents include dimethylformamide (DMF), alcohols (such as ethanol) or tetrahydrofuran, preferably ethanol. The aforesaid reaction can be conducted at a temperature of about 20° C. to about 90° C., preferably about 50° C. to about 65° C. The aforesaid reaction can be conducted for a time period between about 15 minutes to about 16 hours.

The compounds of the formula V can be made by methods well known in the art such as those described in PCT Patent Publication WO 98/58925 or reviewed in *The Organic Chemistry of Drug Synthesis*, D. Lednicer and L. A. Mitscher, Volume 1, pages 167 to 277 and references therein. Each of the above referenced publications and applications is hereby incorporated by reference in its entirety.

Compounds of the formula III are commercially available or can be made by methods well known to those skilled in the art.

The compounds of formula II (H—X-A-Y-B-G-W), are commercially available or can be made by methods well known to those skilled in the art or can be made by the methods of Scheme 5.

Scheme 2 refers to an alternate preparation of compounds of the formula I in a three-step synthesis from compounds of the formula VI or VII. Referring to Scheme 2, a compound of the formula I is prepared by reacting a compound of the formula IX with a suitable base and a suitable $R^1$ introducing agent in the presence of a solvent. Suitable bases include sodium hydride, potassium carbonate, sodium carbonate, triethylamine, pyridine or triethanolamine; preferably sodium hydride. Suitable $R^1$ introducing agents include compounds of the formula $R^1L^4$ wherein $L^4$ is halo, p-tolylsulfonyloxy (OTs) or methylsulfonyloxy (OMs), preferably halo, more preferably chloro or bromo; or alkylating agents such as Eshenmoser's Salts, epoxides or suitably substituted electrophilic aziridines. Suitable solvents depend upon the base used but may be chosen from N,N-dimethylformamide, tetrahydrofuran, acetonitrile or water. The aforesaid reaction can be conducted at a temperature of about 0° C. to about 30° C., preferably about 20° C. to about 25° C. The aforesaid reaction can be conducted for a time period between about 15 minutes to about 16 hours.

A compound of the formula IX may be prepared by reacting a compound of the formula VIII with a urea of the formula III ($H_2NCONH_2$) in the presence of a strong base in a polar solvent. Suitable bases include sodium methoxide, sodium ethoxide and magnesium methoxide; preferably sodium ethoxide. Suitable solvents include alcohols (such as ethanol) or tetrahydrofuran, preferably absolute ethanol. The aforesaid reaction can be conducted at a temperature of about 20° C. to about 90° C., preferably about 50° C. to about 65° C. The aforesaid reaction can be conducted for a time period between about 15 minutes to about 16 hours.

A compound of the formula VIII may be prepared by reacting a compound of the formula VI, wherein $L^1$ and $L^2$ are leaving groups such as methoxy, ethoxy, benzyloxy or chloro, preferably ethoxy, and wherein $L^3$ is a leaving group such as halo, p-tolylsulfonyloxy (OTs) or methylsulfonyloxy (OMs), preferably halo, most preferably chloro, with a compound of the formula II (i.e., compounds of the formula H—X-A-Y-B-G-W) in the presence of a base in a polar solvent. Suitable bases include sodium methoxide, sodium ethoxide, potassium carbonate and sodium hydride; preferably sodium ethoxide. Suitable solvents include dimethylformamide, alcohols (such as ethanol) or tetrahydrofuran, preferably ethanol. The aforesaid reaction can be conducted at a temperature of about 20° C. to about 90° C., preferably about 50° C. to about 70° C. The aforesaid reaction can be conducted for a time period between about 15 minutes to about 16 hours, preferably about 3 hours. Reactions of this type are further illustrated by the method of J. B. Niederl and R. T. Roth, *J. Amer. Chem. Soc.*, 62, 1154 (1940).

Alternatively, a compound of the formula VIII may also be prepared from a compound of the formula VII, wherein $L^1$ and $L^2$ are leaving groups such as methoxy, ethoxy, benzyloxy or chloro, preferably ethoxy, in the presence of a suitable catalyst, preferably rhodium(II)acetate according to the procedure described by M. Campbell et al., *Aust. J. Chem.*, 45, 2061 (1992).

Compounds of the formula VI and VII are commercially available or easily obtained from readily available starting materials according to methods well known to those skilled in the art. For example compounds of the Formula VII may be prepared according to the method of D. W. Peace et al., *Synthesis*, 658 (1971).

Compounds of the formula III ($H_2NCONH_2$) are commercially available or can be prepared by methods well known to those skilled in the art.

Scheme 3 refers to an alternate preparation of compounds of the formula I; in particular those wherein X is —O— or —OCH$_2$—. Referring to Scheme 3, a compound of the formula 1, wherein X is —O—, may be obtained by reacting a compound of the formula XI with a suitable compound of the formula HO-A-Y-B-G-W according to the method of O. Mitsonubu (Synthesis, 1 (1981)). A compound of the formula I, wherein X is —OCH$_2$—, may be obtained by reacting a compound of the formula XI with a suitable alkylating agent of the formula $L^3CH_2$-A-Y-B-G-W, wherein $L^3$ is a leaving group such as halo, p-tolylsulfonyloxy (OTs) or methylsulfonyloxy (OMs), preferably halo, most preferably chloro or bromo, in a suitable solvent in the presence of a suitable base. Suitable solvents include acetonitrile, N,N-dimethylformamide or tetrahydrofuran. Suitable bases include sodium hydride, potassium carbonate, triethylamine, pyridine or triethanolamine. The aforesaid reaction can be conducted at a temperature of about 0° C. to about 50° C., preferably about 20° C. The aforesaid reaction can be conducted for a time period between about 15 minutes to about 16 hours.

Compounds of the formula XI may be prepared from a compound of the formula X according to the method of J. A. Vida et al., *J. Med. Chem.*, 17, 732 (1974).

Compounds of the formula X may be prepared by reacting a compound of the formula XII with a suitable base, in the presence of a suitable alkylating agent and a solvent, such as described in Biehl et al., *J.Het.Chem.*, 23, 9 (1986). Suitable bases include sodium hydride, potassium carbonate, triethylamine, pyridine, or triethanolamine; preferably triethanolamine. Suitable alkylating agents include those of the formula $R^1L^4$ wherein $L^4$ is halo, p-tolylsulfonyloxy (OTs) or methylsulfonyloxy (OMs), preferably halo, most preferably chloro or bromo; or alkylating agents such as Eshenmoser's Salt, epoxides or suitably substituted electrophilic aziridines. Suitable solvents depend upon the base used but may be chosen from N,N-dimethylformamide, tetrahydrofuran, acetonitrile or water. The aforesaid reaction can be conducted at a temperature of about 0° C. to about 30° C., preferably about 20° C. to about 25° C. The aforesaid reaction can be conducted for a time period between about 15 minutes to about 16 hours.

Compounds of the formula XII are commercially available or can be easily prepared by those skilled in the art according to the methods reviewed in *The Organic Chemistry of Drug Synthesis*, D. Lednicer and L. A. Mitscher, Volume 1, pages 167 to 277 and references cited therein.

Scheme 4 refers to yet an alternate preparation of compounds of the formula 1. Referring to Scheme 4, a compound of the formula I may be obtained by reacting a compound of formula XIV with a compound of the formula H—X-A-Y-B-G-W in the presence of a base. Suitable bases include polymer bound bases such as 1,5,7-triazabicyclo[4.4.0]dec-5-ene bound to polystyrene (PTBD) crosslinked with 2% divinyl benzene (DVB) or alkali metal carbonates, preferably PTBD. Suitable solvents include alcohols (such as ethanol, methanol and butanol), dimethylformamide, tetrahydrofuran or acetonitrile, preferably absolute acetonitrile. The aforesaid reaction can be conducted at a temperature of about 20° C. to about 90° C., preferably about 50° C. to about 65° C. The aforesaid reaction can be conducted for a time period between about 15 minutes to about 16 hours.

The compound of formula XIV is prepared by reacting a compound of formula X with a suitable bromination reagent such as $Br_2$ or $Br_2$-$Ph_3P$ in an inert solvent. Suitable solvents include water (in the presence of a suitable base, such as aqueous sodium hydroxide), acetic acid, acetonitrile or dimethylformamide, preferably water. The aforesaid reaction can be conducted at a temperature of about 0° C. to about 40° C., preferably about 20° C. to about 35° C. The aforesaid reaction can be conducted for a time period between about 15 minutes to about 16 hours.

Alternatively, compounds of the formula I, wherein X is —S— or —SCH$_2$—, or wherein X is >SO$_2$, >SO, —SO$_2$CH$_2$—, or —SOCH$_2$—, can be prepared by reacting a compound of the formula X with a suitable disulfide of the formula (S-A-Y-B-G-W)$_2$ or (S—CH$_2$-A-Y-B-G-W)$_2$ in a suitable solvent in the presence of a suitable base. Suitable solvents include N,N-dimethylformamide, tetrahydrofuran, or acetonitrile. Suitable bases include sodium hydride, potassium carbonate, triethylamine, pyridine or triethanolamine. The aforesaid reaction can be conducted at a temperature of about 20° C. to about 70° C., preferably about 20° C. The aforesaid reaction can be conducted for a time period between about 15 minutes to about 16 hours.

Disulfides of the formula (S-A-Y-B-G-W)$_2$ or (S—CH$_2$-A-Y-B-G-W)$_2$ may be prepared from the corresponding thiols of the formula H—S-A-Y-B-G-W or H—S-CH$_2$-A-Y-B-G-W by oxidative methods well known to those skilled the art.

Compounds of the formula X are commercially available, or can be made by methods of scheme 3, or can be made by methods well known to those skilled in the art.

One skilled in the art will also appreciate that the side chains denoted $R^1$ and —X-A-Y-B-G-W may be added as a unit, as is discussed above in schemes 1–4, or can be added as separate modules such as X-A followed by the addition of a second unit L'-Y-B-G-W, wherein L' is a suitable leaving group. Such methods are well known to those skilled in the art.

Scheme 5 describes the preparation of the side chain unit of the formula and —X-A-Y-B-G-W, which is used to prepare compounds of formula I in Schemes 1–4. Referring to Scheme 5, a compound of the formula XV, wherein X' is >(C=O)—Cl can be prepared by reacting a compound of the formula XVI, wherein —X-P is >(C=O)—OH, with a chlorinating agent. Suitable chlorinating agents include thionyl chloride or phosphorous oxychloride. A compound of the formula XV, wherein X' is —OH, —SH, >NHR$^5$, —CH$_2$OH, —CH$_2$SH, —CH$_2$NHR$^5$ or —SO$_2$NHR$^5$, may be prepared by reacting an appropriate compound of formula XVI, wherein X-P is a protected form of —OH, —SH, >NHR$^5$, —CH$_2$OH, —CH$_2$SH, —CH$_2$NHR$^5$ or —SO$_2$NHR$^5$, with a protecting group removal agent under conditions commonly known to those of ordinary skill in the art and referenced in Greene and Wuts, "*Protecting Groups in Organic Synthesis*," (John Wiley & Son Press, 2nd Ed).

Compounds of the formula XVI, wherein Y is —O—, —S—, —CH$_2$O—, —CH$_2$S—, >NR$^6$, —CH$_2$NR$^6$ or SO$_2$NR$^6$, can be prepared by reacting a compound of formula XVII, wherein M is Br or I, with a compound of the formula W-G-B-Y-H in the presence of a suitable base in the presence of a suitable catalyst in a polar aprotic solvent. Suitable bases include alkali metal carbonate or hydroxide base, preferably potassium carbonate. Suitable catalysts include a copper (0) catalyst, preferably finely powdered copper bronze. Suitable solvents include dimethylformamide or 1-methyl-2-pyrrolidinone. The aforesaid reaction can be conducted at a temperature between about 80° C. and 140° C. The aforesaid reaction can be conducted for about 6 to 24 hours.

Alternatively, compounds of the formula XVI, wherein Y is —O—, —S—, —CH$_2$O—, —CH$_2$S—, >NR$^6$, —CH$_2$NR$^6$ or SO$_2$NR$^6$, can be prepared by reacting a compound of formula XVII, wherein M is Cl, Br, I or triflate (TfO), with a compound of the formula W-G-B-Y—H under Buchwald and Hartwig's conditions in the presence of a suitable base, a palladium (0) catalyst and a suitable ligand in a suitable solvent. Suitable bases include an alkoxide base, preferably sodium tert-butoxide. Suitable catalysts include Pd$_2$(dba)$_3$. Suitable ligands include a triaryl phosphine ligand, preferably tri(ortho-tolyl)phosphine. Suitable solvents include an ethereal solvent, preferably dioxane. The aforesaid reaction can be conducted at a temperature of about 40° C. to about 100° C. The aforesaid reaction can be conducted for about 1 hour to 48 hours. Such conditions are reviewed in *Angew. Chem. Int. Ed. Engl.* 1998, 37, 2046–2067 and are well known to those of ordinary skill in the art.

Alternatively, compounds of the formula XVI, wherein Y is —O—, —S—, —CH$_2$O—, —CH$_2$S—, >NR$^6$, —CH$_2$NR$^6$ or SO$_2$NR$^6$, can be prepared by reacting a compound of formula XVII, wherein M is B(OH)$_2$, with a compound of the formula W-G-B-Y—H under an atmosphere of oxygen gas in the presence of a copper catalyst, 4 angstrom molecular sieves and a suitable tertiary amine base in a suitable solvent. Suitable catalysts include copper (II) acetate. Suitable bases include triethylamine or pyridine. Suitable solvents include methylene chloride, dimethyl sulfoxide, or tetrahydrofuran. The aforesaid reaction can be conducted at a temperature of about 10° C. to about 50° C., preferably about 23° C. The aforesaid reaction can be conducted for about 6 hour to 72 hours.

Compounds of the formula XVI, wherein Y is —CH$_2$O—, —CH$_2$S—, —CH$_2$[N(R$^6$)]— or —SO$_2$[N(R$^6$)]—, and wherein —X-P is —OH, can be prepared by a three step reaction from a compound of the formula XVI, wherein X-P is —COR, wherein R is alkyl or aryl. First, compounds of the formula XVI, wherein —X-P is —OH, can be prepared by reacting a compound of formula XVI, wherein X-P is —OCOR, wherein R is alkyl or aryl, with a suitable base, such as a hydroxide base, preferably lithium hydroxide, in a mixture of methanol and water by ester hydrolysis conditions known by those skilled in the art. Second, the compound of formula XVI, wherein X-P is —OCOR, wherein R is alkyl or aryl, can be prepared by reacting a compound of formula XVI, wherein X-P is —COR, wherein R is alkyl or aryl, by so-called Baeyer Villager oxidation conditions, which is a classical organic transformation and well known to those of ordinary skill in the art. Third, the compound of formula XVI, wherein X-P is —COR, wherein R is alkyl or aryl, can be prepared by reacting a compound of formula XVII, wherein X-P is —COR and M is F, with a compound of the formula W-G-B-Y—H in the presence of a suitable base in a polar aprotic solvent. Suitable bases include an alkali metal hydride base, preferably sodium hydride. Suitable solvents include dimethylformamide or tetrahydrofuran. The aforesaid reaction can be conducted at a temperature of about 0° C. to about 140° C. The aforesaid reaction can be conducted for about 1 hour to about 24 hours.

Compounds of the formula XVI, wherein Y is —CH$_2$O—, —CH$_2$S—, —CH$_2$[N(R$^6$)]— or —SO$_2$[N(R$^6$)]—, and wherein X-P is >NR$^5$, can be prepared by a two step reaction from a compound of formula XVII, wherein X-P is —COR, wherein R is alkyl or aryl. First, a compound of the formula XVI, wherein Y is —CH$_2$O—, —CH$_2$S—, —CH$_2$[N(R$^6$)]— or —SO$_2$[N(R$^6$)]—, and wherein X-P is >NR$^5$, can be prepared by reacting a compound of formula XVI, wherein X-P is —COR, wherein R is alkyl or aryl, by the so-called Curtius rearrangement. The Curtius rearrangement is a classical organic transformation and well known to those of ordinary skill in the art. Second, the compound of formula XVI, wherein X-P is —COR, wherein R is alkyl or aryl, can be prepared by reacting a compound of formula XVII, wherein X-P is —COR, and M is F, with a compound of the formula W-G-B-Y—H in the presence of a suitable base in a polar aprotic solvent. Suitable bases include an alkali metal hydride base, preferably sodium hydride. Suitable solvents include dimethylformamide or tetrahydrofuran. The aforesaid reaction can be conducted at a temperature of about 0° C. to about 140° C. The aforesaid reaction can be conducted for about 1 hour to about 24 hours.

Compounds of the formula XVI, wherein Y is >SO$_2$, >S=O, —CH$_2$SO—, —CH$_2$SO$_2$—, —SOCH$_2$—, or —SO$_2$CH$_2$—, may be prepared by reacting the corresponding lower oxidation state compounds of the formula XVI (e.g. wherein Y is —S—, —CH$_2$S—, or —SCH$_2$—) with a suitable oxidant in a suitable solvent. Suitable oxidants include a peroxy acid, preferably peracetic acid, or an organic peroxide, preferably m-chloroperoxybenzoic acid or tert-butyl hydroperoxide. Suitable solvents include methylene chloride or tert-butanol. The aforesaid reaction can be conducted at a temperature between about −10° C. and about 30° C. The aforesaid reaction can be conducted for about 1 hour to about 8 hours.

Compounds of the formula XVI, wherein Y is —OCH$_2$—, —SCH$_2$—, or [N(R$^6$)]CH$_2$— can be prepared by reacting a compound of the formula XVII, wherein M is L-CH$_2$—, wherein L is halo, mesyloxy (MsO) or tosyloxy (TsO), with an appropriate compound of the formula W-G-B-Y—H, wherein Y is —O—, —S— or >NR$^6$, in the presence of a suitable base, in the presence of a polar aprotic solvent. Suitable bases include an alkali metal carbonate base, preferably potassium carbonate, or cesium carbonate. Suitable solvents include dimethylformamide or tetrahydrofuran. The aforesaid reaction can be conducted at a temperature between about 23° C. and about 80° C., preferably about 20° C. to about 50° C. The aforesaid reaction can be conducted for about 1 hour to about 24 hours.

Compounds of the formula XVI, wherein Y is >C=O or —CH=CH—, can be prepared by reacting a compound of formula XVII, wherein M is -B(OH)$_2$, —ZnBr, —ZnCl, or trialkyltin, with a compound of the formula W-G-B-Y-Z, wherein Z is halo, preferably Cl, Br or I, in the presence of a catalyst in a suitable solvent. Suitable catalysts include a palladium or nickel catalyst, preferably Pd(PPh$_3$)$_4$. Suitable solvents include toluene, tetrahydrofuran, dimethylformamide or dimethyl sulfoxide. The aforesaid reaction can be conducted at a temperature between about 23° C. and about 110° C. The aforesaid reaction can be conducted for a period of about 1 hour to about 24 hours. The aforesaid reaction may be facilitated by the presence of a copper salt, such as cuprous iodide or cuprous bromide.

Compounds of the formula XVI, wherein Y is —C≡C— can be prepared by reacting a compound of formula XVII, wherein M is halo or triflate, preferably Br or I, with a compound of the formula W-G-B-Y—H, in the presence of a suitable base and a catalyst in a suitable solvent. Suitable bases include a trialkylamine base, preferably triethylamine. Suitable catalysts include a palladium catalyst, preferably Pd(PPh$_3$)$_4$. Suitable solvents include tetrahydrofuran or dimethylformamide. The aforesaid reaction can be conducted at a temperature between about 23° C. and about 60° C. The aforesaid reaction can be conducted for a period of about 1 hour to about 24 hours.

One of ordinary skill in the art will recognize that compounds of the formula XVI, wherein Y is —CH$_2$CH$_2$—, can be prepared by reacting the aforementioned compounds of the formula XVI, wherein Y is —CH=CH— or —C≡C—, with a reducing agent in the presence of a palladium catalyst in a suitable solvent. Suitable reducing agents include hydrogen gas at ambient pressure to 50 psi. Preferred catalyst is palladium on charcoal. Suitable solvents include methanol or ethyl acetate. The aforesaid reaction can be conducted at a temperature between about 20° C. and about 50° C. The aforesaid reaction can be conducted for about 1 hour to about 24 hours.

Compounds of the formula XVII, wherein P is a suitable protecting group as defined in Greene and Wuts, supra, are either commercially available, known, or may be prepared from commercially available starting materials by methods known to those of ordinary skill in the art.

Scheme 6 describes the preparation of compounds of the formula XVIII, wherein X is —OCH$_2$—, SCH$_2$— or —[N(R$^5$)]CH$_2$—. Compounds of the formula XVIII are compounds of formula IV in Scheme 1, wherein R$^1$ is hydrogen. Referring to Scheme 6, compounds of formula XVIII, wherein L$^1$ and L$^2$ are leaving groups such as methoxy, ethoxy, benzyloxy or chloro, preferably ethoxy, can be prepared by reacting a compound of formula XIX, wherein L$^1$ and L$_2$ are leaving groups as defined above, with a compound of formula W-G-B-Y-A-X—H, wherein X is —O—, —S— or >NR$^5$, in the presence of a suitable base and a suitable solvent. Suitable bases include an alkali metal hydride base, preferably sodium hydride. Suitable solvents include an alcoholic solvent, tetrahydrofuran, or dimethylformamide. The aforesaid reaction can be conducted at a temperature of about −20° C. to about 50° C., preferably about 0° C. to about 23° C. The aforesaid reaction can be conducted for about 1 hour to about 24 hours.

The compounds of the formula I, which are basic in nature, are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Biological Assays

The ability of the compounds of formula I or their pharmaceutically acceptable salts (hereinafter also referred to as the compounds of the present invention) to inhibit metalloproteinases or mammalian reprolysins and, consequently, demonstrate their effectiveness for treating diseases characterized by metalloproteinase activity may be shown by the following in vitro and in vivo assay tests.

MMP Assays

MMP-13 selective inhibitors may be identified by screening the inhibitors of the present invention through the MMP fluorescence assays described below and selecting those agents with MMP-X/MMP-13 inhibition IC$_{50}$ ratios of 100 or greater and potency of less than 100 nM, where MMP-X refers to one or more other MMPs.

Non-selective collagenase inhibitors as used herein, unless otherwise mentioned, refer to agents which exhibit less than a 100 fold selectivity for the inhibition of MMP-13 enzyme activity over MMP-X enzyme activity or a potency of more than 100 nM as defined by the IC$_{50}$ results from the MMP-13 and MMP-X fluorescence assays described below.

The ability of collagenase inhibitors to inhibit collagenase activity is well known in the art. The degree of inhibition of a particular MMP for several compounds has been well documented in the art and those skilled in the art will know how to normalize different assay results to those assays reported herein. The following assays may be used to identify matrix metalloproteinase inhibitors.

Inhibition of Human Collagenase (MMP-1)

Human recombinant collagenase is activated with trypsin. The amount of trypsin may be optimized for each lot of collagenase-1 but a typical reaction uses the following ratio: 5 μg trypsin per 100 μg of collagenase. The trypsin and collagenase may be incubated at room temperature for 10 minutes then a five fold excess (50 mg/10 mg trypsin) of soybean trypsin inhibitor is added.

Stock solutions (10 mM) of inhibitors may be made up in dimethylsulfoxide and then diluted using the following scheme:

10 mM ----► 120 μM ----► 12 μM ----► 1.2 μM ----► 0.12 μM

Twenty-five microliters of each concentration may then be added in triplicate to appropriate wells of a 96 well microfluor plate. The final concentration of inhibitor may be a 1:4 dilution after addition of enzyme and substrate. Positive controls (enzyme, no inhibitor) may be set up in wells D7–D12 and negative controls (no enzyme, no inhibitors) may be set in wells D1–D6.

Collagenase-1 may be diluted to 240 ng/ml and 25 μl is then added to appropriate wells of the microfluor plate. Final concentration of collagenase in the assay may be 60 ng/ml.

Substrate (DNP-Pro-Cha-Gly-Cys(Me)-His-Ala-Lys (NMA)—NH$_2$) may be made as a 5 mM stock in dimethylsulfoxide and then diluted to 20 μM in assay buffer. The assay may be initiated by the addition of 50 μl substrate per well of the microfluor plate to give a final concentration of 10 μM.

Fluorescence readings (360 nM excitation, 460 nm emission) may be taken at time 0 and then at 20 minute intervals. The assay may be conducted at room temperature with a typical assay time of 3 hours.

Fluorescence versus time may be then plotted for both the blank and collagenase containing samples (data from triplicate determinations is averaged). A time point that provides a good signal (at least five fold over the blank) and that is on a linear part of the curve (usually around 120 minutes) may be chosen to determine IC$_{50}$ values. The zero time may be used as a blank for each compound at each concentration and these values may be subtracted from the 120-minute data. Data may be plotted as inhibitor concentration versus % control (inhibitor fluorescence divided by fluorescence of collagenase alone×100). IC$_{50}$'s may be determined from the concentration of inhibitor that gives a signal that is 50% of the control.

If IC$_{50}$'s are reported to be less than 0.03 μM then the inhibitors may be assayed at concentrations of 0.3 μM, 0.03 μM and 0.003 μM.

Inhibition of Gelatinase (MMP-2)

Human recombinant 72 kD gelatinase (MMP-2, gelatinase A) may be activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors may be diluted serially in assay buffer (50 mM TRIS, pH 7.5, 200 mM NaCl, 5 mM CaCl$_2$, 20 μM ZnCl$_2$ and 0.02% BRIJ-35 (vol./vol.)) using the following scheme:

10 mM ----► 120 μM ----► 12 μM ----► 1.2 μM ----► 0.12 μM

Further dilutions may be made as necessary following this same scheme. A minimum of four inhibitor concentrations for each compound may be performed in each assay. 25 μL of each concentration may be then added to triplicate wells of a black 96 well U-bottomed microfluor plate. As the final assay volume may be 100 μL, final concentrations of inhibitor may be the result of a further 1:4 dilution (i.e. 30 μM - - - →3 μM - - - →0.3 μM - - - →0.03 μM, etc.). A blank (no enzyme, no inhibitor) and a positive enzyme control (with enzyme, no inhibitor) may be also prepared in triplicate.

Activated enzyme may be diluted to 100 ng/mL in assay buffer, 25 μL per well may be added to appropriate wells of the microplate. Final enzyme concentration in the assay may be 25 ng/mL (0.34 nM).

A five mM dimethylsulfoxide stock solution of substrate (Mca-Pro-Leu-Gly-Leu-Dpa-Ala-Arg-NH$_2$) may be diluted in assay buffer to 20 μM. The assay may be initiated by addition of 50 μL of diluted substrate yielding a final assay concentration of 10 μM substrate. At time zero, fluorescence reading (320 excitation; 390 emission) may be immediately taken and subsequent readings may be taken every fifteen minutes at room temperature with a PerSeptive Biosystems CytoFluor Multi-Well Plate Reader with the gain at 90 units.

The average value of fluorescence of the enzyme and blank may be plotted versus time. An early time point on the linear part of this curve may be chosen for IC$_{50}$ determinations. The zero time point for each compound at each dilution may be subtracted from the latter time point and the data then expressed as percent of enzyme control (inhibitor fluorescence divided by fluorescence of positive enzyme control×100). Data may be plotted as inhibitor concentration versus percent of enzyme control. IC$_{50}$'s may be defined as the concentration of inhibitor that gives a signal that is 50% of the positive enzyme control.

Inhibition of Stromelysin Activity (MMP-3)

Human recombinant stromelysin (MMP-3, stromelysin-1) may be activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors may be diluted serially in assay buffer (50 mM TRIS, pH 7.5, 150 mM NaCl, 10 mM CaCl$_2$ and 0.05% BRIJ-35 (vol./vol.)) using the following scheme:

10 mM ----► 120 μM ----► 12 μM ----► 1.2 μM ----► 0.12 μM

Further dilutions may be made as necessary following this same scheme. A minimum of four inhibitor concentrations for each compound may be performed in each assay. 25 μL of each concentration may be then added to triplicate wells of a black 96 well U-bottomed microfluor plate. As the final assay volume may be 100 μL, final concentrations of inhibitor may be the result of a further 1:4 dilution (i.e. 30 μM - - - →3 μM - - - →0.3 μM - - - →0.03 μM, etc.). A blank (no enzyme, no inhibitor) and a positive enzyme control (with enzyme, no inhibitor) may be also prepared in triplicate.

Activated enzyme is diluted to 200 ng/mL in assay buffer, 25 µL per well may be added to appropriate wells of the microplate. Final enzyme concentration in the assay may be 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-NH$_2$) may be diluted in assay buffer to 6 µM. The assay may be initiated by addition of 50 µL of diluted substrate yielding a final assay concentration of 3 µM substrate. At time zero, fluorescence reading (320 excitation; 390 emission) may be immediately taken and subsequent readings may be taken every fifteen minutes at room temperature with a PerSeptive Biosystems CytoFluor Multi-Well Plate Reader with the gain at 90 units.

The average value of fluorescence of the enzyme and blank may be plotted versus time. An early time point on the linear part of this curve may be chosen for IC$_{50}$ determinations. The zero time point for each compound at each dilution may be subtracted from the latter time point and the data then expressed as percent of enzyme control (inhibitor fluorescence divided by fluorescence of positive enzyme control×100). Data may be plotted as inhibitor concentration versus percent of enzyme control. IC$_{50}$'s may be defined as the concentration of inhibitor that gives a signal that is 50% of the positive enzyme control.

Inhibition of Human 92 kD Gelatinase (MMP-9)

Inhibition of 92 kD gelatinase (MMP-9) activity may be assayed using the Mca-Pro-Leu-Gly-Leu-Dpa-Ala-Arg-NH$_2$ substrate (10 µM) under similar conditions as described above for the inhibition of human collagenase (MMP-1).

Human recombinant 92 kD gelatinase (MMP-9, gelatinase B) may be activated for 2 hours with 1 mM p-aminophenyl-mercuric acetate (from a freshly prepared 100 mM stock in 0.2 N NaOH) at 37 C.

10 mM dimethylsulfoxide stock solutions of inhibitors may be diluted serially in assay buffer (50 mM TRIS, pH 7.5, 200 mM NaCl, 5 mM CaCl$_2$, 20 µM ZnCl$_2$, 0.02% BRIJ-35 (vol./vol.)) using the following scheme:

10 mM ----➤ 120 µM ----➤ 12 µM ----➤ 1.2 µM ----➤ 0.12 µM

Further dilutions may be made as necessary following this same scheme. A minimum of four inhibitor concentrations for each compound may be performed in each assay. 25 µL of each concentration is then added to triplicate wells of a black 96 well U-bottomed microfluor plate. As the final assay volume may be 100 µL, final concentrations of inhibitor may be the result of a further 1:4 dilution (i.e. 30 µM - - - →3 µM - - - →0.3 µM - - - →0.03 µM, etc.). A blank (no enzyme, no inhibitor) and a positive enzyme control (with enzyme, no inhibitor) may be also prepared in triplicate.

Activated enzyme may be diluted to 100 ng/mL in assay buffer, 25 µL per well may be added to appropriate wells of the microplate. Final enzyme concentration in the assay may be 25 ng/mL (0.27 nM).

A five mM dimethylsulfoxide stock solution of substrate (Mca-Pro-Leu-Gly-Leu-Dpa-Ala-Arg-NH$_2$) may be diluted in assay buffer to 20 µM. The assay may be initiated by addition of 50 µL of diluted substrate yielding a final assay concentration of 10 µM substrate. A zero time fluorescence reading (320 excitation; 390 emission) may be immediately taken and subsequent readings may be taken every fifteen minutes at room temperature with a PerSeptive Biosystems CytoFluor Multi-Well Plate Reader with the gain at 90 units.

The average value of fluorescence of the enzyme and blank may be plotted versus time. An early time point on the linear part of this curve may be chosen for IC$_{50}$ determinations. The zero time point for each compound at each dilution may be subtracted from the latter time point and the data then expressed as percent of enzyme control (inhibitor fluorescence divided by fluorescence of positive enzyme control×100). Data may be plotted as inhibitor concentration versus percent of enzyme control. IC$_{50}$'s may be defined as the concentration of inhibitor that gives a signal that is 50% of the positive enzyme control.

Inhibition of MMP-13

Human recombinant MMP-13 may be activated with 2 mM APMA (p-aminophenyl mercuric acetate) for 1.5 hours, at 37° C. and may be diluted to 400 mg/ml in assay buffer (50 mM Tris, pH 7.5, 200 mM sodium chloride, 5 mM calcium chloride, 20 PM zinc chloride, 0.02% brij). Twenty-five microliters of diluted enzyme may be added per well of a 96 well microfluor plate. The enzyme may be then diluted in a 1:4 ratio in the assay by the addition of inhibitor and substrate to give a final concentration in the assay of 100 mg/ml.

10 mM stock solutions of inhibitors may be made up in dimethyl sulfoxide and then diluted in assay buffer as per the inhibitor dilution scheme for inhibition of human collagenase (MMP-1): Twenty-five microliters of each concentration may be added in triplicate to the microfluor plate. The final concentrations in the assay may be 30 µM, 3 µM, 0.3 µM and 0.03 µM.

Substrate (Dnp-Pro-Cha-Gly-Cys(Me)-His-Ala-Lys (NMA)—NH$_2$) may be prepared as for inhibition of human collagenase (MMP-1) and 50 µl may be added to each well to give a final assay concentration of 10 µM. Fluorescence readings (360 nM excitation; 450 emission) may be taken at time 0 and every 5 minutes for 1 hour.

Positive controls may consist of enzyme and substrate with no inhibitor and blanks consist of substrate only.

IC$_{50}$'s may be determined as per inhibition of human collagenase (MMP-1). If IC$_{50}$'s are reported to be less than 0.03 µM, inhibitors may be then assayed at final concentrations of 0.3 µM, 0.03 µM, 0.003 µM and 0.0003 µM.

Collagen Film MMP-13 Assay

Rat type I collagen may be radiolabeled with $^{14}$C acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase were added to the well, the enzyme cleaves the insoluble collagen which unwinds and would thus solubilized. Collagenase activity may be directly proportional to the amount of collagen solubilized, determined by the proportion of radioactivity released into the supernatant as measured in a standard scintillation counter. Collagenase inhibitors may be, therefore, compounds which reduce the radioactive counts released with respect to the controls with no inhibitor present. One specific embodiment of this assay may be described in detail below.

For determining the selectivity of compounds for MMP-13 versus MMP-1 using collagen as a substrate, the following procedure may be used. Recombinant human proMMP-13 or proMMP-1 may be activated according to the procedures outlined above. The activated MMP-13 or MMP-1 may be diluted to 0.6 µg/ml with buffer (50 mM Tris pH 7.5, 150 mM NaCl, 10 mM $CaCl_2$, 1 µM $ZnCl_2$, 0.05% Brij-35, 0.02% sodium azide).

Stock solutions of test compound (10 mM) in dimethylsulfoxide may be prepared. Dilutions of the test compounds in the Tris buffer, above, may be made to 0.2, 2.0, 20, 200, 2000 and 20000 nM.

100 µl of appropriate drug dilution and 100 µl of diluted enzyme may be pipetted into wells of a 96 well plate containing collagen films labeled with $^{14}C$-collagen. The final enzyme concentration may be 0.3 µg/ml while the final drug concentration is 0.1, 1.0, 10, 100, 1000 nM. Each drug concentration and control may be analyzed in triplicate. Triplicate controls may be also run for the conditions in which no enzyme may be present and for enzyme in the absence of any compound.

The plates may be incubated at 37° C. for a time period such that around 30–50% of the available collagen may be solubilized. The time period may be determined by counting additional control wells at various time points. In most cases around 9 hours of incubation may be required. When the assay has progressed sufficiently, the supernatant from each well may be removed and counted in a scintillation counter. The background counts (determined by the counts in the wells with no enzyme) may be subtracted from each sample and the % release calculated in relation to the wells with enzyme only and no inhibitor. The triplicate values for each point may be averaged and the data graphed as percent release versus drug concentration. $IC_{50}$'s may be determined from the point at which 50% inhibition of release of radiolabeled collagen may be obtained.

To determine the identity of the active collagenases in cartilage conditioned medium, assays may be conducted using collagen as a substrate, cartilage conditioned medium containing collagenase activity and inhibitors of varying selectivity. The cartilage conditioned medium may be collected during the time at which collagen degradation may be occurring and thus may be representative of the collagenases responsible for the collagen breakdown. Assays may be conducted as outlined above except that instead of using recombinant MMP-13 or recombinant MMP-1, cartilage conditioned medium may be the enzyme source.

IL-1 Induced Cartilage Collagen Degradation from Bovine Nasal Cartilage

This assay may use bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue may be used because it: (1) is very similar to articular cartilage, (2) is readily available, (3) is relatively homogeneous and (4) degrades with predictable kinetics after IL-1 stimulation.

Two variations of this assay may be used to assay compounds. Both variations may give similar data. The two variations may be described below:

Variation 1

Three plugs of bovine nasal cartilage (approximately 2 mm diameter×1.5 mm long) may be placed into each well of a 24 well tissue culture plate. One ml of serumless medium may be then added to each well. Compounds may be prepared as 10 mM stock solutions in dimethyl sulfoxide and then diluted appropriately in serumless medium to final concentrations, e.g., 50, 500 and 5000 nM. Each concentration may be assayed in triplicate.

Human recombinant IL-1α (5 ng/mL) (IL-1) may be added to triplicate control wells and to each well containing drug. Triplicate control wells may be also set up in which neither drug nor IL-1 may be added. The medium may be removed and fresh medium containing IL-1 and the appropriate drug concentrations may be added on days 6, 12, 18 and 24 or every 3–4 days if necessary. The media removed at each time point may be stored at −20° C. for later analysis. When the cartilage in the IL-1 alone wells may have been almost completely resorbed (about day 21), the experiment may be terminated. The medium may be removed and stored. Aliquots (100 µl) from each well at each time point may be pooled, digested with papain and then analyzed for hydroxyproline content. Background hydroxyproline (average of wells with no IL-1 and no drug) may be subtracted from each data point and the average calculated for each triplicate. The data may be then expressed as a percent of the IL-1 alone average value and plotted. The $IC_{50}$ may be determined from this plot.

Variation 2

The experimental set-up may be the same as outlined above in Variation 1, until day 12. On day 12, the conditioned medium from each well may be removed and frozen. Then one ml of phosphate buffered saline (PBS) containing 0.5 µg/ml trypsin may be added to each well and incubation continued for a further 48 hours at 37° C. After 48 hours incubation in trypsin, the PBS solution may be removed. Aliquots (50 µl) of the PBS/trypsin solution and the previous two time points (days 6 and 12) may be pooled, hydrolyzed and hydroxyproline content determined. Background hydroxyproline (average of wells with no IL-1 and no drug) may be subtracted from each data point and the average calculated for each triplicate. The data may be then expressed as a percent of the IL-1 alone average value and plotted. The $IC_{50}$ may be determined from this plot. In this variation, the time course of the experiment v shortened considerably. The addition of trypsin for 48 hours after 12 days of IL-1 stimulation likely releases any type II collagen that may have been damaged by collagenase activity but not yet released from the cartilage matrix. In the absence of IL-1 stimulation, trypsin treatment may produce only low background levels of collagen degradation in the cartilage explants.

Inhibition of TNF Production

The ability or inability of the compounds or the pharmaceutically acceptable salts thereof to inhibit the production of TNF may be shown by the following in vitro assay:

Human Monocyte Assay

Human mononuclear cells may be isolated from anti-coagulated human blood using a one-step Ficoll-hypaque separation technique. The mononuclear cells may be washed three times in Hanks balanced salt solution (HBSS) with divalent cations and resuspended to a density of $2 \times 10^6$/ml in HBSS containing 1% BSA. Differential counts may be determined using the Abbott Cell Dyn 3500 analyzer indicated that monocytes ranged from 17 to 24% of the total cells in these preparations.

180 μl of the cell suspension may be aliquoted into flat bottom 96 well plates (Costar). Additions of compounds and LPS (100 ng/ml final concentration) may give a final volume of 200 μl. All conditions may be performed in triplicate. After a four hour incubation at 37° C. in an humidified $CO_2$ incubator, plates may be removed and centrifuged (10 minutes at approximately 250×g) and the supernatants removed and assayed for TNF a using the R&D ELISA Kit.

Aggrecanase Assay

Primary porcine chondrocytes from articular joint cartilage may be isolated by sequential trypsin and collagenase digestion followed by collagenase digestion overnight and may be plated at $2 \times 10^5$ cells per well into 48 well plates with 5 μCi/ml $^{35}S$ (1000 Ci/mmol) sulfur in type I collagen coated plates. Cells may be allowed to incorporate label into their proteoglycan matrix (approximately 1 week) at 37° C., under an atmosphere of 5% $CO_2$.

The night before initiating the assay, chondrocyte monolayers may be washed two times in DMEM/1% PSF/G and then allowed to incubate in fresh DMEM/1% FBS overnight.

The following morning chondrocytes may be washed once in DMEM/1% PSF/G. The final wash may be allowed to sit on the plates in the incubator while making dilutions.

| Media and dilutions may be made as described in the Table below. | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 μM stock of each compound in DMEM in 96 well plate. Store in freezer overnight. The next day perform serial dilutions in DMEM with IL-1 to 5 μM, 500 nM and 50 nM. Aspirate final wash from wells and add 50 μl of compound from above dilutions to 450 μl of IL-1 media in appropriate well of the 48 well plates. Final compound concentrations equal 500 nM, 50 nM and 5 nM. All samples completed in triplicate with Control and IL-1 alone samples on each plate. |

Plates may be labeled and only the interior 24 wells of the plate may be used. On one of the plates, several columns may be designated as IL-1 (no drug) and Control (no IL-1, no drug). These control columns may be periodically counted to monitor $^{35}S$-proteoglycan release. Control and IL-1 media may be added to wells (450 μl) followed by compound (50 μl) so as to initiate the assay. Plates may be incubated at 37° C., with a 5% $CO_2$ atmosphere.

At 40–50% release (when CPM from IL-1 media were 4–5 times control media) as assessed by liquid scintillation counting (LSC) of media samples, the assay may be terminated (9–12 hours). Media may be removed from all wells and placed in scintillation tubes. Scintillate may be added and radioactive counts are acquired (LSC). To solubilize cell layers, 500 μl of papain digestion buffer (0.2 M Tris, pH 7.0, 5 mM EDTA, 5 mM DTT and 1 mg/ml papain) may be added to each well. Plates with digestion solution may be incubated at 60° C. overnight. The cell layer may be removed from the plates the next day and placed in scintillation tubes. Scintillate may be then added and samples counted (LSC).

The percent of released counts from the total present in each well may be determined. Averages of the triplicates may be made with control background subtracted from each well. The percent of compound inhibition may be based on IL-1 samples as 0% inhibition (100% of total counts).

The compounds of the present invention that were tested all have $IC_{50}$'s in at least one of the above assays of less than 100 μM preferably less than 100 nM. Certain preferred groups of compounds possess differential selectivity toward the various MMPs or ADAMs.

One group of preferred compounds possesses selective activity towards MMP-13 over MMP-1. Another preferred group of compounds possesses selective activity towards MMP-13 over MMP-1, MMP-3 and MMP-7. Another preferred group of compounds possesses selective activity towards MMP-13 over MMP-1, MMP-3, MMP-7 and MMP-17. Another preferred group of compounds possesses selective activity towards MMP-13 over MMP-1, MMP-2, MMP-3, MMP-7, MMP-9 and MMP-14 Another preferred group of compounds possesses selective activity towards MMP-13 over MMP-12 and MMP-14.

For administration to mammals, including humans, for the inhibition of matrix metalloproteinases, a variety of conventional routes may be used including oral, parenteral (e.g., intravenous, intramuscular or subcutaneous), buccal, anal and topical. In general, the compounds of the invention (hereinafter also known as the active compounds) will be administered at dosages of about 0.1 and 25 mg/kg body weight of the subject to be treated per day, preferably from about 0.3 to 5 mg/kg. Preferably the active compound will be administered orally or parenterally. However, some variation in dosage may necessarily occur depending on the condition of the subject being treated. The person responsible for administration may, in any event, determine the appropriate dose for the individual subject.

The compounds of the present invention may be administered in a wide variety of different dosage forms, in general, the therapeutically effective compounds of this invention may present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc may often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes and, if so desired, emulsifying and/or suspending agents as well, together with such diluents as water, ethanol, propylene glycol, glycerin and various like combinations thereof. In the case of animals, they may be advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient may usually be prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions may be suitable intravenous injection purposes. The oily solutions may be suitable for intraarticular, intramuscular and subcutaneous injection purposes. The preparation of all these solutions under sterile conditions may be readily accomplished by standard pharmaceutical techniques well known to those skilled in the art. In the case of animals, compounds may be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention may be conveniently delivered in the form of a solution or suspension from a pump spray container that may be squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials may also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers may be added to increase viscosity or for sustained release (such as cellulosic polymers, Dextran, polyethylene glycol, or alginic acid). These solutions may be suitable for intraorbital injection purposes. The preparation of all these solutions under sterile conditions is readily accomplished by standard pharmaceutical techniques well known to those skilled in the art. In the case of animals, compounds may be administered intraorbitally at dosage levels of about 0.1 to 50 mg/kg/day, advantageously 0.2 to 10 mg/kg/day given in a single dose or up to 3 divided doses.

As with the other routes of administration and corresponding dosage forms described herein, dosage forms intended for oral administration may be also suitably formulated to provide controlled-, sustained- and/or delayed release of the active ingredient. Typically, these would include delayed-release oral tablets, capsules and multiparticulates, as well as enteric-coated tablets and capsules which prevent release and adsorption of the active ingredient in the stomach of the patient and facilitate enteric delivery distal to the stomach, i.e., in the intestine. Other typical oral dosage forms may include sustained-release oral tablets, capsules and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

The following Examples illustrate the preparation of the compounds of the present invention. Melting points were uncorrected. NMR data were reported in parts per million ($\delta$) and are referenced to the deuterium lock signal from the sample solvent (deuteriochloroform unless otherwise specified). Commercial reagents were utilized without further purification. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure or in vacuo means that a rotary evaporator was used.

Preparation 1

2-(4-(4-Methoxyphenoxy)phenyl)-4-trifluoromethanesulfonyloxyoxazole 4-(4-Cyanophenoxy)-methoxybenzene 4-Methoxyphenol (24.6 g, 198 mmol), 4-fluorobenzonitrile (24.0 g, 198 mmol) and potassium carbonate (32.8 g, 238 mmol) in dimethylacetamide were heated together at 150° C. for 5 h. The cooled mixture was diluted with ethyl acetate and water. The separated organic layer was washed with water and brine and dried with magnesium sulfate. Filtration and concentration gave a yellow solid which was recrystallized from ethanol to give 42.6 g of 4-cyanophenyl-4'-methoxyphenyl ether as a white solid. GC-MS (m/z, EI): 225 [M]$^+$.

4-(4-Methoxyphenoxy)benzamide 4-(4-Cyanophenoxy)-methoxybenzene (7.66 g, 34 mmol) and water (6.13 g, 340 mmol) in methanesulfonic acid (32.7 g) were heated to 80° C. for 16 hours. The cooled mixture was poured onto ice/water and after stirring for 1 hour the solid was collected and air dried yielding 8.4 g of 4-(4-methoxyphenoxy)benzamideas a white solid. GC-MS (m/z, EI): 243 [M]$^+$.

N-(2-Chloroacetyl)-4-(4-methoxyphenoxy)benzamide 4-(4-Methoxyphenoxy)benzamide (8.34 g, 34.3 mmol) and chloroacetyl chloride (19.4 g, 171 mmol) were heated together at 100° C. for 2 hours. The cooled mixture was diluted with ethyl ether and hexane. After stirring for 1 hour at room temperature the solid was collected yielding 8.98 g of N-(2-chloroacetyl)-4-(4-methoxyphenoxy)benzmide as a light orange solid. MS (m/z, APCI): 320 [M+H]$^+$.

2-(4-(4-Methoxyphenoxy)phenyl)-4-hydroxyoxazole

N-(2-chloroacetyl)-4-(4-methoxyphenoxy)benzmide (5.63 g, 17.6 mmol) was stirred in methylene chloride with 4A molecular sieves (8.8 g, powdered). After 30 minutes 1,5,7-triazabicyclo[4.4.0]dec-5-ene bound to polystyrene crosslinked with 2% DVB (Fluka) (8.13 g @ 2.6 meq/g, 21.2 meq) was added. After 1 h more the mixture was filtered through diatomaceous earth and the filtrate concentrated yielding 3.77 g of 2-(4-(4-methoxyphenoxy)phenyl)-4-hydroxyoxazole as a yellow solid. GC-MS (m/z, EI): 283 [M]+.

2-(4-(4-Methoxyphenoxy)phenyl)-4-trifluoromethanesulfonyloxyoxazole 2-(4-(4-Methoxyphenoxy)phenyl)-4-hydroxyoxazole (3.76 g, 13.3 mmol) in methylene chloride at 0° C. was treated with 2,6-lutidine (4.28 g, 39.9 mmol) followed by triflic anhydride (7.5 g, 26.6 mmol). After 2 hour silica gel was added to the reaction mixture and the solvents were removed in vacuo. The product absorbed on the silica gel was chromatographed yielding 4.28 g of 2-(4-(4-methoxyphenoxy)phenyl)-4-trifluoromethanesulfonyloxyoxazole. GC-MS (m/z, EI): 415 [M]+.

Preparation 2A 5-(2-Ethoxy-ethyl)-pyrimidine-2,4,6-trione

Sodium metal (8.6 g, 0.38 mol) was added to ethanol (375 mL), and the mixture was stirred at ambient temperature until homogeneous. Diethyl malonate (60 g, 0.38 mol) was added, followed by bromoethyl ethyl ether (57.4 g, 0.38 mol). After stirring at reflux for 3 hours, the mixture was cooled to ambient temperature and concentrated in vacuo. The resulting material was added to a mixture of sodium ethoxide and ethanol (prepared by the reaction of 17.2 g of sodium metal with 600 mL of methanol). Urea (249) was added, and the resulting mixture was refluxed for 2.5 hours. After cooling to ambient temperature, the mixture was stirred for 12 hours, acidified with 1M hydrochloric acid solution, extracted three times with ethyl acetate, and the combined organic layers were dried over sodium sulfate ($Na_2SO_4$), filtered and concentrated in vacuo, affording 5-(2-ethoxy-ethyl)-pyrimidine-2,4,6-trione as a colorless solid.

Preparation 2B 5-(2-Methoxy-ethyl)-pyrimidine-2,4,6-trione

By the same procedure as Preparation 2A, the title compound was prepared from diethyl malonate and bromoethyl methyl ether.

Preparation 2C 5-(2—Benzyloxy-ethyl)-pyrimidine-2,4,6-trione

By the same procedure as Preparation 2A, the title compound was prepared from diethyl malonate and bromoethyl benzyl ether.

Preparation 3A

5—Bromo-5-(2-ethoxy-ethyl)-pyrimidine-2,4,6-trione

To a mixture of 5-(2-ethoxy-ethyl)-pyrimidine-2,4,6-trione (27.8 g, 139 mmol) (from Preparation 2A) and 1.5 L of water was added 1M sodium hydroxide solution (140 mL) and bromine (7.2 mL, 22.2 g, 139 mmol) at 0° C. After warming to room temperature, the mixture was stirred for 48 hours, filtered, and the solids were washed with water, then ether, then hexanes and dried in vacuo, afforidng 23 g of 5-bromo-5-(2-ethoxy-ethyl)-pyrimidine-2,4,6-trione. $^1$H NMR (CDCl$_3$): 8.37 (bs, 2H), 3.53 (t, 2H, J=7.0 Hz), 3.35 (q, 2H, J=6.5 Hz), 2.99 (t, 2H, J=7.0 Hz), 1.05 (t, 3H, J=6.5 Hz) ppm. MS (m/z, APCI): 468 [M+H]+.

Preparation 3B

5—Bromo-5-(2-methoxy-ethyl)-pyrimidine-2,4,6-trione

By the same procedure as Preparation 3A, 5-(2-methoxy-ethyl)-pyrimidine-2,4,6-trione (from Preparation 2B) was converted to the title compound. MS (m/z, APCI): 263/265 [M−H]−.

Preparation 3C

5—Bromo-5-(2—benzyloxy-ethyl)-pyrimidine-2,4,6-trione

By the same procedure as Preparation 3A, 5-(2—benzyloxy-ethyl)-pyrimidine-2,4,6-trione (5.25 g, 20.0 mmole) (from Preparation 2C) was converted to 5.90 g of the title compound. LC-MS (m/z, APCI): 339/341 [M−H]−.

Preparation 4

4-(4-Iodophenoxy)methoxybenzene 4-(Phenoxy)methoxybenzene 4-(Phenoxy)phenol (9.31 g, 50 mmol) in THF (100 mL) was treated with potassium t-butoxide (6.17 g, 55 mmol) at room temperature for 10 min. Methyl iodide (7.87 g, 55 mmol) was added by syringe. After stirring for 18 h at room temperature the reaction was quenched with saturated ammonium chloride solution and diluted with ethyl ether. The separated organic layer was washed with saturated ammonium chloride solution, dried with magnesium sulfate, filtered and concentrated to give 9.98 g of the title compound as a pale yellow oil. GS-MS (m/z, EI): 200 [M]+.

4-(4-Iodophenoxy)methoxybenzene 4-(Phenoxy)methoxybenzene (7.40 g, 36.9 mmol) was dissolved in acetic acid and treated with iodine monochloride (7.50 g, 46.2 mmol) at 50° C. for 4 hours. The mixture was then concentrated and the residue taken up in methylene chloride. The solution was washed with 10% sodium sulfite solution, dried with magnesium sulfate, filtered and concentrated to a yellow solid. This was triturated with hexane, collected and dried to give 8.06 g of the title compound as a pale pink solid. GS-MS (m/z, EI): 326 [M]+.

Preparation 5

4-(4-Methoxyphenoxy)phenylboronic acid

To a solution of 4-(4—Bromophenoxy)methoxybenzene (5.0 g, 17.9 mmol) (Yeager et al., *Synthesis* 1991, 63) in tetrahydrofuran at −78° C. was added n-butyllithium (13.5 mL @ 1.5 M, 26.9 mmol) by syringe. After a few min tri-isopropylborate (6.73 g, 35.8 mmol) was added and the reaction allowed to warm to room temperature. After 3 hours the reaction was quenched with 1N hydrochloric acid and the mixture stirred for 18 hours. The organic phase was separated and the aqueous phase extracted with diethyl ether. The combined organic fractions were dried with magnesium sulfate, filterd and concentrated. The residue was chromatographed yielding 2.86 g of the title compound. LC-MS (m/z, APCI): 289 [M+HCO2H−H]+.

Preparation 6

3-Phenyl-5-trifluoromethanesulfonyloxyisoxazole

3-Phenyl-4,5-dihydroisoxazol-2-one (1.61 g, 10.0 mmol) and 2,6-lutidine (1.61 g, 15 mmol) were combined in methylene chloride at 0° C. Triflic anhydride (3.39 g, 12 mmol) was then added by syringe. After 4 hours the reaction was quenched with saturated ammonium chloride. The separated organic layer was dried over magnesium sulfate, filtered and the filtrate concentrated. The crude product was chromatographed to give 2.56 g of the title compound as a white solid. GC-MS (m/z, EI): 293 [M]+.

Preparation 7

4-(4-Hydroxyphenoxy)benzoic acid

Part A: Benzyl 4-fluorobenzoate

4-Fluorobenzoyl chloride (16.0 g, 101 mmol) in methylene chloride was added dropwise to a solution of benzyl alcohol (10.8 g, 100 mmol) and triethylamine (10.1 g, 100 mmol) in methylene chloride. After stirring 18 hours at room temperature the mixture was quenched with saturated ammonium chloride solution, diluted with methylene chloride and washed with 1N hydrochloric acid. The separated organic layer was washed with saturated sodium bicarbonate solution and brine and dried with sodium sulfate. Filtration and concentration give 24.2 g of the title compound as an oil that was taken directly into the next step.

Part B: Benzyl 4-(4—benzyloxy)phenoxybenzoate

To a solution of 4-benzyloxyphenol (17.82 g, 89 mmol) and potassium tert-butoxide (9.99 g, 89 mmol) in dimethylformamide was added a solution of benzyl 4-fluorobenzoate in tetrahydrofuran. The mixture was stirred at 80° C. for 18 hours. The reaction was quenched with saturated ammonium chloride solution, diluted with diethyl ether and washed with saturated ammonium chloride solution, saturated sodium bicarbonate solution and brine. The extract was dried with magnesium sulfate, filtered and concentrated to give 15.9 g of the title compound. LC-MS (m/z, APCI): 411 [M+H]+.

Part C: 4-(4-hydroxyphenoxy)benzoic acid

Benzyl 4-(4—benzyloxy)phenoxybenzoate (19.8 g, 48.2 mmol) in ethyl acetate was hydrogenated over 10% palladium on carbon at 40 psi for 18 hours. The reaction was filtered and the filtrate concentrated to a solid. This was recrystallized from ethyl acetate/hexane to give 10.5 g of the title compound. LC-MS (m/z, APCI): 229 [M−H]−.

Preparation 8

4-(4–Cyanophenoxy)phenol

Hydroquinone (18 g, 163.5 mmol), 4-fluorobenzonitrile (10 g, 81.75 mmol) and potassium carbonate (23 g, 163.5 mmol) were heated to 150° C. in dimethylformamide (40 mL) for 6 hours. The cooled mixture was diluted with water and 1 N hydrochloric acid and extracted with ethyl acetate. The separated organic layer was dried over sodium sulfate, filtered and concentrated. The crude product was chromatographed yielding 8 g of the title compound. MS (m/z, APCI): 210 [M−H]−.

EXAMPLE 1

5-(2-Methoxy-ethyl)-5-{4-[4-(4-(2-fluorophenyl)-oxazol-2-yl)-phenoxy]-phenoxy}-pyrimidine-2,4,6-trione Part A: 4-[4-(4-(2-fluorophenyl)-oxazol-2-yl)-phenoxy]-methoxybenzene 2-(4-(4-Methoxyphenoxy)phenyl)-4-trifluoromethanesulfonyloxyoxazole (415 mg, 1.0 mmol) (from Preparation 1), 2-fluorobenzeneboronic acid (168 mg, 1.2 mmol), cesium carbonate (782 mg, 2.4 mmol), tetrakis (triphenylphosphine) palladium (58 mg, 0.05 mmol), and powdered 4A molecular sieves (1.0 g) were combined in a dry flask which was then purged with nitrogen. Dry, degassed dioxane was added by syringe and the mixture warmed to 80° C. for 2 hours. The cooled mixture was filtered through diatomaceous earth rinsing with tetrahydrofuran. Silica gel (5 g) was added to the filtrate and the mixture concentrated to dryness. The crude product absorbed on silica gel was chromatographed yielding 333 mg of the title compound as a white solid. GC-MS (m/z, EI): 361 [M]+.

Part B: 4-[4-(4-(2-fluorophenyl)-oxazol-2-yl)-phenoxy]-phenol

4-[4-(4-(2-Fluorophenyl)-oxazol-2-yl)-phenoxy]-methoxybenzene (320 mg, 0,88 mmol) and methionine (661 mg, 4.4 mmol) were combined in neat methanesulfonic acid (10 mL, 154 mmol) and heated to 50° C. for 3 hours. The cooled mixture was carefully added to sodium hydroxide (6.16 g, 154 mmol) in ice/water. The pH was adjusted to 8 and the product extracted with ethyl acetate. The extract was washed with saturated sodium bicarbonate solution, dried over magnesium sulfate, filtered, and concentrated yielding 287 mg of the title compound as a white solid. GC-MS (m/z, EI): 347 [M]+.

Part C: 5-(2-Methoxy-ethyl)-5-{4-[4-(4-(2-fluorophenyl)-oxazol-2-yl)-phenoxy]-phenoxy}-pyrimidine-2,4,6-trione 4-[4-(4-(2-fluorophenyl)-oxazol-2-yl)-phenoxy]-phenol (142 mg, 0.41 mmol), and 1,5,7-triazabicyclo[4.4.0]dec-5-ene bound to polystyrene crosslinked with 2% DVB (Fluka) (473 mg @ 2.6 meq/g, 1.23 meq) in acetonitrile were shaken for 30 minutes. 5-Bromo-5-(2-methoxy-ethyl)-pyrimidine-2,4,6-trione (163 mg, 0.62 mmol) (from Preparation 3b) was then added and shaking continued for 3 days. The reaction was quenched with 20% acetic acid in methanol and after 15 minutes filtered. The filtrate was concentrated and the crude product chromatographed yielding 145 mg of 5-(2-methoxy-ethyl)-5-{4-[4-(4-(2-fluorophenyl)-oxazol-2-yl)-phenoxy]-phenoxy}-pyrimidine-2,4,6-trione as a white solid. LC-MS (m/z, APCI): 533 [M+H]+.

EXAMPLE 2

5-(2-Ethoxy-ethyl)-5-{4-[4-(4-(2-fluorophenyl)-oxazol-2-yl)-phenoxy]-phenoxy}-pyrimidine-2,4,6-trione By the same procedures described in Example 1 but using 5-bromo-5-(2-ethoxy-ethyl)-pyrimidine-2,4,6-trione (from Preparation 3A) in Part C, the title compound was prepared. LC-MS (m/z, APCI): 547 [M+H]+.

EXAMPLE 3

5-(2-Methoxy-ethyl)-5-{4-[4-(4-(3-fluorophenyl)-oxazol-2-yl)-phenoxy]-phenoxy}-pyrimidine-2,4,6-trione By the same procedures described in Example 1 but using 3-fluorobenzeneboronic acid in Part A, the title compound was prepared. LC-MS (m/z, APCI): 532 [M+H]+.

EXAMPLE 4

5-(2-Ethoxy-ethyl)-5-{4-[4-(4-(3-fluorolhenyl)-oxazol-2-yl)-phenoxy]-phenoxy}-pyrimidine-2,4,6-trione By the same procedures described in Example 3 but using 5-bromo-5-(2-ethoxy-ethyl)-pyrimidine-2,4,6-trione (from Preparation 3A) in Part C, the title compound was prepared. LC-MS (m/z, APCI): 546 [M+H]+. $^1$H-NMR (DMSO-$d_6$): δ 1.07 (m, 3H), 2.43 (br t, 2H), 3.3 (2H signal obscured by water peak), 3.50 (br t, 2H), 6.80 (d, 2H), 7.08 (m, 4H), 7.20 (t, 1H), 7.52 (dd, 1H), 7.67 (d,1H), 7.73 (d, 1H), 8.03 (d, 2H), 8.78 (s, 1H), 11.86 (s, 1H).

EXAMPLE 5

5-(2-Methoxy-ethyl)-5-{4-[4-(4-(4-fluorophenyl)-oxazol-2-yl]-phenoxy}-phenoxy-pyrimidine-2,4,6-trione By the same procedures described in Example 1 but using 4-fluorobenzeneboronic acid in Part A, the title compound was prepared. LC-MS (m/z, APCI): 533 [M+H]$^+$. $^1$H-NMR (DMSO-d$_6$):.δ2.39 (br m, 2H), 3.14 (s, 3H), 3.46 (br m, 2H), 6.75 (d, 2H), 7.04 (br "t", 4H), 7.27 ("t", 2H), 7.86 (dd, 2H), 8.00 (d, 2H), 8.65 (s, 1H), 11.85 (s, 1H).

EXAMPLE 6

5-(2-Ethoxy-ethyl)-5-{4-[4-(4-(4-fluorophenyl)-oxazol-2-yl)-phenoxy]-phenoxy}-pyrimidine-2,4,6-trione By the same procedures described in Example 5 but using 5-bromo-5-(2-ethoxy-ethyl)-pyrimidine-2,4,6-trione (from Preparation 3A) in Part C, the title compound was prepared. LC-MS (m/z, APCI): 547 [M+H]$^+$.

EXAMPLE 7

5-(2-Methoxy-ethyl)-5-{4-[4-(4-(3-pyridyl)-oxazol-2-yl)-phenoxy]-phenoxy}-pyrimidine-2,4,6-trione By the same procedures described in Example 1 but using 3-pyridylboronic acid propan-1,3-diol ester in Part A, the title compound was prepared. LC-MS (m/z, APCI): 516 [M+H]$^+$.

EXAMPLE 8

5-(2-Ethoxy-ethyl)-5-{4-[4-(4-(3-pyridyl)-oxazol-2-yl)-phenoxy]-phenoxy}-pyrimidine-2,4,6-trione By the same procedures described in Example 7 but using 5-bromo-5-(2-ethoxy-ethyl)-pyrimidine-2,4,6-trione (from Preparation 3A) in Part C, the title compound was prepared. LC-MS (m/z, APCI): 530 [M+H]$^+$.

EXAMPLE 9

5-(2-Methoxy-ethyl)-5-{4-[4-(4-(4-pyridyl)-oxazol-2-yl)-phenoxy]-phenoxy}-pyrimidine-2,4,6-trione By the same procedures described in Example 1 but using 4-pyridylboronic acid pinacol ester in Part A, the title compound was prepared. LC-MS (m/z, APCI): 516 [M+H]$^+$.

EXAMPLE 10

5-(2-Ethoxy-ethyl)-5-{4-[4-(4-(4-pyridyl)-oxazol-2-yl)-phenoxy]-phenoxy}-pyrimidine-2,4,6-trione By the same procedures described in Example 9 but using 5-bromo-5-(2-ethoxy-ethyl)-pyrimidine-2,4,6-trione (from Preparation 3A) in Part C, the title compound was prepared. LC-MS (m/z, APCI): 530 [M+H]$^+$.

EXAMPLE 11

5-(2—Benzaloxy-ethyl)-5-{4-[4-(4-(2-fluorolhenyl)-oxazol-2-yl)-phenoxy]-phenoxy}-pyrimidine-2,4,6-trione By the same procedures described in Example 1 but using 5-bromo-5-(2—Benzyloxy-ethyl)-pyrimidine-2,4,6-trione (from Preparation 3C) in Part C, the title compound was prepared. LC-MS (m/z, APCI): 608 [M+H]$^+$.

EXAMPLE 12

5-(2-Methoxy-ethyl)-5-{4-[4-(4-phenyl-oxazol-2-yl)-phenoxy]-phenoxy}-pyrimidine-2,4,6-trione Part A: 4-[4-(4-phenyl-oxazol-2-yl)-phenoxy]-methoxybenzene To a solution of 4-phenyloxazole (653 mg, 4.5 mmol) (Whitney et al. *J. Org. Chem* 1989, 55, 929) in dry tetrahydrofuran was added at −70° C., n-butyllithium (1.98 mL @ 2.5 M, 4.95 mmol). After 30 minutes anhydrous zinc chloride solution in ethyl ether (13.5 mL @ 1.0 M, 13.5 mmol) was added at −70° C. The mixture was allowed to warm to 0° C. over 1 hour. This mixture was added to a solution of 4-iodophenyl 4'-methoxyphenyl ether (978 mg, 3.0 mmol) (from Preparation 4) and tetrakis(triphenylphosphine) palladium (347 mg, 0.3 mmol) in dry tetrahydrofuran and the reaction warmed to 60° C. for 1 hour. The cooled reaction mixture was filtered through diatomaceous earth, rinsing with ethyl acetate. The filtrate was washed with saturated ammonium chloride solution, dried over magnesium sulfate, filtered and concentrated. The crude product was triturated with hexanes and collected yielding 1.05 g of the title compound as a white solid. LC-MS (m/z, APCI): 344 [M+H]$^+$.

Part B: 4-[4-(4-phenyl-oxazol-2-yl)-phenoxy]-phenol

By the same procedure described in Example 1, Part B but using the product from Example 12, Part A, the title compound was prepared. LC-MS (m/z, APCI): 330 [M+H]$^+$.

Part C: 5-(2-Methoxy-ethyl)-5-{4-[4-(4-phenyl-oxazol-2-yl)-phenoxy]-phenoxy}-pyrimidine-2,4,6-trione By the same procedures described in Example 1, Part C but using the product from Example 12, Part B, the title compound was prepared. LC-MS (m/z, APCI): 515 [M+H]$^+$.

EXAMPLE 13

5-(2-Ethoxy-ethyl)-5-{4-[4-(4-phenyl-oxazol-2-yl)-phenoxy]-phenoxy}-pyrimidine-2,4,6-trione By the same procedures described in Example 12 but using 5-bromo-5-(2-ethoxy-ethyl)-pyrimidine-2,4,6-trione (from Preparation 3C) in Part C, the title compound was prepared. LC-MS (m/z, APCI): 529 [M+H]$^+$.

EXAMPLE 14

5-(2-Methoxy-ethyl)-5-{4-[4-(4-(2-pyridyl)-oxazol-2-yl)-phenoxy]-phenoxy}-pyrimidine-2,4,6-trione Part A: 4-[4-(4-(2-Pyridyl)-oxazol-2-yl)-phenoxy]-methoxybenzene 2-(4-(4-Methoxyphenoxy)phenyl)-4-trifluoromethanesulfonyloxyoxazole (831 mg, 2.0 mmol) (from Preparation 1) and tetrakis(triphenylphosphine) palladium (116 mg, 0.1 mmol) were combined in a dry flask which was then purged with nitrogen. Dry, degassed tetrahydorfuran was added by syringe followed by pyridylzinc bromide solution in tetrahydrofuran (8.0 mL @ 0.5 M, 4.0 mmole). The mixture warmed to 80° C. for 5 hours. Silica gel (5 g) was added to the cooled mixture and the mixture concentrated to dryness. The crude product absorbed on silica gel was chromatographed yielding 1.40 g of crude product which was triturated with ethyl acetate/ethyl ether yielding 689 mg of the title compound as a light yellow solid. LC-MS (m/z, APCI): 345 [M+H]$^+$.

Part B: 4-[4-(4-(2-Pyridyl)-oxazol-2-yl)-phenoxy]-phenol

By the same procedure described in Example 1, Part B but using the product from Example 14, Part A, the title compound was prepared. LC-MS (m/z, APCI): 331 [M+H]$^+$.

Part C: 5-(2-Methoxy-ethyl)-5-{4-[4-(4-(2-pyridyl)-oxazol-2-yl)-phenoxy]-phenoxy}-pyrimidine-2,4,6-trione By the same procedures described in Example 1, Part C but using the. product from Example 14, Part B, the title compound was prepared. LC-MS (m/z, APCI): 515 [M+H]$^+$.
$^1$H-NMR (DMSO-d$_6$):.δ 2.42 (t, 2H), 3.17 (s, 3H), 3.49 (t, 2H), 6.79 (d, 2H), 7.07 (m, 4H), 7.37 (t, 1H), 7.93 (m, 2H), 8.04 (d, 2H), 8.61 (d, 1H), 8.71 (s, 1H), 11.88 (s, 1H).

EXAMPLE 15

5-(2-Methoxy-ethyl)-5-{4-[4-(4-(2-pyridyl)-oxazol-2-yl)-Phenoxy]-phenoxy}-pyrimidine 2,4,6-trione By the same procedures described in Example 14 but using 5-bromo-5-(2-ethoxy-ethyl)-pyrimidine-2,4,6-trione (from Preparation 3A) in Part C, the title compound was prepared. LC-MS (m/z, APCI): 530 [M+H]$^+$.

EXAMPLE 16

5-(2-Methoxy-ethyl)-5-{4-[4-(4-(2-cyanophenyl)-oxazol-2-yl)-phenoxy]-phenoxy}-pyrimidine-2,4,6-trione Part A: 4-[4-(4-(2-cyanophenyl)-oxazol-2-yl)-phenoxy]-methoxybenzene By the same procedure as described in Example 14, Part A but using 2-cyanophenylzinc bromide, the title compound was prepared. LC-MS (m/z, APCI): 369 [M+H]$^+$.

Part B: 4-[4-(4-(2-Cyanophenyl)-oxazol-2-yl)-phenoxy]-phenol

4-[4-(4-(2-Cyanophenyl)-oxazol-2-yl)-phenoxy]-methoxybenzene (589 mg, 1.60 mmol) was suspended in dry methylene chloride and cooled to 0° C. Boron tribromide solution in methylene chloride (2.4 mL @ 1.0 M, 2.4 mmol) was added by syringe and the mixture stirred for 18 h at room temperature. The mixture was concentrated to a solid which was then triturated with 1N hydrochloric acid for 1 hour. The resulting solid was collected and washed well with water. The damp solid was dried by dissolving in tetrahydrofuran and reconcentrating to dryness yielding 609 mg of the title compound as a light brown foam. LC-MS (m/z, APCI): 355 [M+H]$^+$.

Part C: 5-(2-Methoxy-ethyl)-5-{4-[4-(4-(2-cyanophenyl)-oxazol-2-yl)-phenoxy]-phenoxy}-pyrimidine-2,4,6-trione By the same procedure as described in Example 1, Part C but using the product of Example 16, Part B, the title compound was prepared. LC-MS (m/z, APCI): 539 [M+H]$^+$.

EXAMPLE 17

5-(2-Ethoxy-ethyl)-5-{4-[4-(4-(2-cyanophenyl)-oxazol-2-yl)-phenoxy]-phenoxy}-pyrimidine-2,4,6-trione By the same procedures described in Example 16 but using 5-bromo-5-(2-ethoxy-ethyl)-pyrimidine-2,4,6-trione (from Preparation 3A) in Part C, the title compound was prepared. LC-MS (m/z, APCI): 553 [M+H]$^+$.

EXAMPLE 18

5-(2-Methoxy-ethyl)-5-{4-[4-(4-(3-cyanophenyl)-oxazol-2-yl)-phenoxy]-phenoxy}-pyrimidine-2,4,6-trione Part A: 4-[4-(4-(3-cyanophenyl)-oxazol-2-yl)-phenoxy]-methoxybenzene By the same procedure as described in Example 1, Part A but using 3-cyanophenylboronic acid, the title compound was prepared. LC-MS (m/z, APCI): 370 [M+H]$^+$.

Part B: 4-[4-(4-(3-cyanophenyl)-oxazol-2-yl)-phenoxy]-phenol

By the same procedure as described in Example 16, Part B but using the product from Example 18, Part A, the title compound was prepared. LC-MS (m/z, APCI): 355 [M+H]$^+$.

Part C: 5-(2-Methoxy-ethyl)-5-{4-[4-(4-(3-cyanophenyl)-oxazol-2-yl)-phenoxy]-phenoxy}-pyrimidine-2,4,6-trione By the same procedure as described in Example 1, Part C but using the product of Example 18, Part B, the title compound was prepared. LC-MS (m/z, APCI): 540 [M+H]$^+$.

EXAMPLE 19

5-(2-Ethoxy-ethyl)-5-{4-[4-(4-(3-cyanophenyl)-oxazol-2-yl)-phenoxy]-phenoxy}-pyrimidine-2,4,6-trione By the same procedures described in Example 18 but using 5-bromo-5-(2-ethoxy-ethyl)-pyrimidine-2,4,6-trione (from Preparation 3A) in Part C, the title compound was prepared. LC-MS (m/z, APCI): 552 [M+H]$^+$.

EXAMPLE 20

5-(2-Methoxy-ethyl)-5-{4-[4-(4-(4-cyanophenyl)-oxazol-2-yl)-phenoxy]-phenoxy}-pyrimidine-2,4,6-trione By the same procedures as described in Example 18 but using 4-cyanophenylboronic acid in Part A, the title compound was prepared. LC-MS (m/z, APCI): 540 [M+H]$^+$.

EXAMPLE 21

5-(2-Ethoxy-ethyl)-5-{4-[4-(4-(4-cyanophenyl)-oxazol-2-yl)-phenoxy]-phenoxy}-pyrimidine-2,4,6-trione By the same procedures described in Example 20 but using 5-bromo-5-(2-ethoxy-ethyl)-pyrimidine-2,4,6-trione (from Preparation 3A) in Part C, the title compound was prepared. LC-MS (m/z, APCI): 554 [M+H]$^+$.

EXAMPLE 22

5-(2-Methoxy-ethyl)-5-{4-[4-(4-(2-pyrazinyl)-oxazol-2-yl)-phenoxy]-phenoxy}-pyrimidine-2,4,6-trione Part A: 4-[4-(4-(2-pyrazinyl)-oxazol-2-yl)-phenoxy]-methoxybenzene Tetrakis(triphenylphosphine) palladium (279 mg, 0.25 mmol) was placed in a dry flask which was then purged with nitrogen. Dry nitrogen purged dioxane (25 mL), 2-iodopyrazine (1.03 g, 5.0 mmol) and hexamethylditin (1.64 g, 5.0 mmol) were all added by syringe. The mixture was warmed to 60° C. for 16 hours and 100° C. for 3 hours. A 20 mL portion of the cooled mixture was withdrawn with a syringe and added through a nylon syringe filter to a dry flask containing a mixture of 2-(4-(4-methoxyphenoxy)phenyl)-4-trifluoromethanesulfonyloxyoxazole (831 mg, 2.0 mmol) (from Preparation 1), tetrakis(triphenylphosphine) palladium (116 mg, 0.1 mmol), and lithium chloride (424 mg, 10 mmol). The mixture was heated at 100° C. for 24 hours. To the cooled reaction was added silica gel (5 g) and the mixture concentrated to dryness. The crude product absorbed on silica gel was chromatographed yielding 355 mg of the title compound as a light brown solid. LC-MS (m/z, APCI): 347 [M+H]$^+$.

Part B: 4-[4-(4-(2-pyrazinyl)-oxazol-2-yl)-phenoxy]-phenol

By the same procedure as described in Example 16, Part B but using the product from Example 22, Part A, the title compound was prepared. LC-MS (m/z, APCI): 332 [M+H]$^+$.

Part C: 5-(2-Methoxy-ethyl)-5-{4-[4-(4-(2-pyrazinyl)-oxazol-2-yl)-phenoxy]-phenoxy}-pyrimidine-2,4,6-trione By the same procedure as described in Example 1, Part C but using the product of Example 22, Part B, the title compound was prepared. LC-MS (m/z, APCI): 516 [M+H]$^+$.

EXAMPLE 23

5-(2-Methoxy-ethyl)-5-{4-[4-(4-(2-pyrimidinyl)-oxazol-2-yl)-phenoxy]-phenoxy}-pyrimidine-2,4,6-trione By the same procedures as described in Example 22 but using 2-bromopyrimidine in Part A, the title compound was prepared. LC-MS (m/z, APCI): 516 [M+H]$^+$.

EXAMPLE 24

5-(2-Methoxy-ethyl)-5-{4-[4-(4-(5-pyrimidinyl)-oxazol-2-yl)-phenoxy]-phenoxy}-pyrimidine-2,4,6-trione By the same procedures as described in Example 22 but using 5-bromopyrimidine in Part A, the title compound was prepared. LC-MS (m/z, APCI): 516 [M+H]+.

EXAMPLE 25

5-(2-Hydroxy-ethyl)-5-{4-L4-(4-(3-fluorophenyl)-oxazol-2-yl)-phenoxy]-phenoxy}-pyrimidine-2,4,6-trione 5-(2-Benzyloxy-ethyl)-5-{4-[4-(4-(3-fluorophenyl)-oxazol-2-yl)-phenoxy]-phenoxy}-pyrimidine-2,4,6-trione (450 mg, 0.74 mmol) in tetrahydrofuran was hydrogenated over 10% palladium on carbon (145 mg) at 40 psi in the presence of concentrated hydrochloric acid (2 drops) for 5 hours. The reaction was filtered and the filtrate concentrated. The crude product was crystallized by trituration with methylene chloride. Filtration and drying yielded 276 mg of the title compound as a tan solid. LC-MS (m/z, APCI): 518 [M+H]+.

EXAMPLE 26

5-(Methoxy-methyl)-5-{4-[4-(4-(4-fluorophenyl)-oxazol-2-yl)-phenoxy]-phenoxy}-pyrimidine-2,4,6-trione Part A: 4-[4-(iodo)-phenoxy]-phenol By the same procedure as described in Example 16, Part B but using the product of Preparation 4, the title compound was prepared.

Part B: Diethyl 2-{4-[4-(iodo)-phenoxy]-phenoxy}-malonate

Under an inert atmosphere 4-[4-(iodo)-phenoxy]-phenol (670 g, 2.03 mol) was dissolved in dimethylformamide. Potassium carbonate (301 g, 2.13 mol) was added. After 30 minutes diethyl chloromalonate (431 g, 2.09 mol) was added to the suspension. After stirring for 6 hour the mixture was partitioned between tert-butyl methyl ether and water. The separated aqueous layer was extracted with tert-butyl methyl ether. The combined organic layers were washed with water and concentrated. Tetrahydrofuran was added and the solution re-concentrated and dried under high vacuum yielding 1010 g of the title compound as a clear yellow oil. $^1$H-NMR (CDCl3) δ 1.31 (t, 6H), 4.3–4.4 (m, 4H), 5.15 (s, 1H), 6.7 (m, sH), 7.0 (m, 4H), 7.6 (m, 2H).

Part C: Diethyl 2-(Methoxy-methyl)-2-{4-[4-(iodo)-phenoxy]-phenoxy}-malonate

Under an inert atmosphere diethyl 2-{4-[4-(iodo)-phenoxy]-phenoxy}-malonate (1000 g, 1.62 mol) was dissolved in dry tetrahydrofuran. This solution was added to a suspension of sodium hydride (113.8 g, 2.84 mol @ 60% in oil) in tetrahydrofuran. After 3.5 hours the mixture was cooled to 2° C. and methoxymethylchloride (241.1 g, 2.84 mol) was added. Stirring at ambient temperature continued for 17 hours. The reaction was quenched with saturated ammonium chloride solution, diluted with water and extracted with ethyl acetate. The separated aqueous layer was extracted with ethyl acetate. The combined organic extracts were washed with water and concentrated. The residual oil was diluted with tetrahydrofuran and re-concentrated to give the crude product which was chromatographed yielding 650 g as a turbid yellow oil. $^1$H-NMR (CDCl3) δ 1.27 (t, 6H), 3.38 (s, 3H), 3.98 (s, 2H), 4.2–4.4 (m, 4H), 6.7 (m, sH), 7.0 (m, 4H), 7.6 (m, 2H).

Part D: Diethyl 2-(Methoxy-methyl)-2-{4-[4-(4-(4-fluorophenyl)-oxazol-2-yl)-phenoxy]-phenoxy}-malonate By the same procedure described in Example 12, Part A but using the product of Example 26, Part C and 4-(4-fluorophenyl)oxazole (Whitney et al. J. Org. Chem 1989, 55, 929), the title compound was prepared. LC-MS (m/z, APCI): 550 [M+H]+.

Part E: 5-(Methoxy-methyl)-5-{4-[4-(4-(4-fluorophenyl)-oxazol-2-yl)-phenoxy]-phenoxy}-pyrimidine-2,4,6-trione Sodium (210 mg, 9.1 mmol) was dissolved in dry ethanol (18 mL). Urea (328 mg, 5.46 mmol) and diethyl 2-(Methoxy-methyl)-2-{4-[4-(4-(4-fluorophenyl)-oxazol-2-yl)-phenoxy]-phenoxy}-malonate (1.0 g, 1.82 mmol) were added and the solution refluxed for 6 hours. The cooled mixture was diluted with ethyl ether and was with water and 2N sodium hydroxide solution. The combined aqueous layers were acidified with hydrochloric acid and extracted with ethyl acetate. The organic layer was washed with brine and dried over sodium sulfate. Filtration and concentration gave 179 mg of crude product which was chromatographed yielding 86 mg of the title compound as a white solid. LC-MS (m/z, APCI): 518 [M+H]+.

EXAMPLE 27

5-(2-Methoxy-ethyl)-5-{4-[4-(4-(4-fluorophenyl)-oxazol-2-yl)-phenoxy]-phenoxy}-pyrimidine-2,4,6-trione sodium salt 5-(2-Methoxy-ethyl)-5-{4-[4-(4-(4-fluorophenyl)-oxazol-2-yl)-phenoxy]-phenoxy)-pyrimidine-2,4,6-trione (53 mg, 0.1 mmol) was slurried in tetrahydrofuran and sodium hydroxide solution (0.105 mL @ 1.00M, 0.105 mmol) was added. The solids all dissolved and the solvent then removed with a stream of nitrogen. The residue was triturated with ethyl ether yielding a fine white solid. The ethyl ether was removed with a stream of nitrogen yielding 53 mg of the title compound as a white solid. $^1$H-NMR (DMSO-$d_6$):.δ 2.06 (br m, 2H), 3.16 (s, 3H), 3.41 (br m, 2H), 6.58 (d, 2H), 6.98 ("t", 4H), 7.27 ("t", 2H), 7.86 (dd, 2H), 7.96 (d, 2H), 8.64 (s, 1H), 9.95 (s, 1H).

EXAMPLE 28

5-(2-Ethoxy-ethyl)-5-{4-[4-(4-(3-fluorophenyl)-oxazol-2-yl)-phenoxy]-phenoxy}-pyrimidine-2,4,6-trione sodium salt By the same procedure described in Example 27 but using the product of Example 4, the title compound was prepared. $^1$H-NMR (DMSO-$d_6$):.δ 1.07 (m, 3H), 2.11 (m, 2H), 3.3 (2H signal obscured by water peak), 3.49 (m, 2H), 6.62 (d, 2H), 7.01 (m, 4H), 7.18 (t, 1H), 7.51 (m, 1H), 7.66 (d, 1H), 7.71 (d, 1H), 8.01 (d, 2H), 8.76 (s, 1H), 9.96 (s, 1H).

EXAMPLE 29

5-(2-Ethoxy-ethyl)-5-{4-[4-(4-(2-pyridyl)-oxazol-2-yl)-phenoxy]-phenoxy}-pyrimidine-2,4,6-trione sodium salt By the same procedure described in Example 27 but using the product of Example 14, the title compound was prepared. $^1$H-NMR (DMSO-$d_6$):.δ 2.10 (br m, 2H), 3.19 (s, 3H), 3.44 (br m, 2H), 6.62 (d, 2H), 7.00 (m, 4H), 7.36 (t, 1H), 7.93 (m, 2H), 8.02 (d, 2H), 8.60 (d, 2H), 8.69 (s, 1H).

EXAMPLE 30

5-(2-Methoxy-ethyl)-5-{4-[4-(5-(phenyl)-oxazol-2-yl)-phenoxy]-phenoxy}-pyrimidine-2,4,6-trione Part A: 4-[4-(5-(phenyl)-oxazol-2-yl)-phenoxy]-methoxybenzene By the same procedure described in Example 12, Part A but using 5-phenyloxazole in Part A, the title compound was prepared. GC-MS (m/z, EI): 343 [M]+

Part B: 4-[4-(5-(phenyl)-oxazol-2-yl)-phenoxy]-phenol

By the same procedure described in Example 1, Part B, the title compound was prepared. LC-MS (m/z, APCI): 330 [M+H]$^+$ Part C: 5-(2-Methoxy-ethyl)-5-{4-[4-(5-(phenyl)-oxazol-2-yl)-phenoxy]-phenoxy}-pyrimidine-2,4,6-trione By the same procedure described in Example 1, Part C, the title compound was prepared. LC-MS (m/z, APCI): 515 [M+H]$^+$

EXAMPLE 31

5-(2-Ethoxy-ethyl)-5-{4-[4-(5-(phenyl)-oxazol-2-yl)-phenoxy]-phenoxy}-pyrimidine-2,4,6-trione By the same procedures described in Example 31 but using 5-bromo-5-(2-ethoxy-ethyl)-pyrimidine-2,4,6-trione (from Preparation 3A) in Part C, the title compound was prepared. LC-MS (m/z, APCI): 529 [M+H]$^+$.

EXAMPLE 32

5-(2-Methoxy-ethyl)-5-{4-[4-(2-(phenyl)-oxazol-5-yl)-phenoxy]-phenoxy}-pyrimidine-2,4,6-trione Part A: 4-[4-(2-(phenyl)-oxazol-5-yl)-phenoxy]-methoxybenzene By the same procedure described in Example 1, Part A but using 5-bromo-2-phenyloxazole (Kashima et al. *Synthesis* 1989, 873) and 4-(4-methoxyphenoxy)phenylboronic acid (from Preparation 5), the title compound was prepared. GC-MS (m/z, EI): 343 [M+H]$^+$.

Part B: 4-[4-(2-(phenyl)-oxazol-5-yl)-phenoxy]-phenol

By the same procedure described in Example 1, Part B, the title compound was prepared. LC-MS (m/z, APCI): 331 [M+H]$^+$ Part C: 5-(2-Methoxy-ethyl)-5-{4-[4-(5-(phenyl)-oxazol-2-yl)-phenoxy]-phenoxy}-pyrimidine-2,4,6-trione By the same procedure described in Example 1, Part C, the title compound was prepared. LC-MS (m/z, APCI): 515 [M+H]$^+$.

EXAMPLE 33

5-(2-Ethoxy-ethyl)-5-{4-[4-(2-(phenyl)-oxazol-5-yl)-phenoxy]-phenoxy}-pyrimidine-2,4,6-trione By the same procedures described in Example 32 but using 5-bromo-5-(2-ethoxy-ethyl)-pyrimidine-2,4,6-trione (from Preparation 3A) in Part C, the title compound was prepared. LC-MS (m/z, APCI): 529 [M+H]$^+$.

EXAMPLE 34

5-(2-Methoxy-ethyl)-5-{4-[4-(3-(phenyl)-isoxazol-5-yl)-phenoxy]-phenoxy}-pyrimidine-2,4,6-trione By the same procedures described in Example 32 but using 3-phenyl-5-trifluoromethylsulfonyloxyisoxazole (from Preparation 6) in Part A, the title compound was prepared. LC-MS (m/z, APCI): 515 [M+H]$^+$.

EXAMPLE 35

5-(2-Ethoxy-ethyl)-5-{4-[4-(3-(phenyl)-isoxazol-5-yl)-phenoxy]-phenoxy}-pyrimidine-2,4,6-trione By the same procedures described in Example 34 but using 5-bromo-5-(2-ethoxy-ethyl)-pyrimidine-2,4,6-trione (from Preparation 3A) in Part C, the title compound was prepared. LC-MS (m/z, APCI): 529 [M+H]$^+$.

EXAMPLE 36

5-(2-Methoxy-ethyl)-5-{4-[4-(3-(phenyl)-[1,2,4]oxadiazol-5-yl)-phenoxy]-phenoxy}-pyrimidine-2,4,6-trione Part A: N-hydroxybenzenecarboximidamide By the procedure of Gangloff et al. (*Tetrahedron Lett* 2001, 42, 1441) benzonitrile was converted to the title amidoxime.

Part B: 4-[4-(3-Phenyl-[1,2,4]oxadiazol-5-yl)-phenoxy]-phenol

To a stirred solution of 2-(1H-benxotriazol-1-yl)-1,1,3,3-tetramethyluronium tetrafluoroborate (706 mg, 2.2 mmol), 1-hydroxybenztriazole (54 mg, 0.4 mmol) and diisopropylethylamine (1.29 g, 10.0 mmol) in dimethylformamide (3.2 mL) was added a solution of N-hydroxybenzenecarboximidamide (300 mg, 2.2 mmol) and 4-(4-hydroxyphenoxy)benzoic acid (from Preparation 7) (460 mg, 2.0 mmol) in dimethylformamide (3.2 mL). After a few minutes, the mixture was warmed to 110 IC for 3 hours. The mixture stood overnight at 0° C. and was then diluted with ethyl acetate and washed with 1N hydrochloric acid, saturated sodium bicarbonate solution, and brine. The extract was dried over sodium sulfate, filtered and concentrated to a red oil that was chromatographed yielding 320 mg of the title compound as a white crystalline solid. LC-MS (m/z, APCI): 329 [M−H]$^-$.

Part C: 5-(2-Methoxy-ethyl)-5-{4-[4-(3-(phenyl)-[1,2,4]oxadiazol-5-yl)-phenoxy]-phenoxy}-pyrimidine-2,4,6-trione By the same procedure described in Example 1, Part C the title compound was prepared. LC-MS (m/z, APCI): 516 [M+H]$^+$.

EXAMPLE 37

5-(2-Ethoxy-ethyl)-5-{4-[4-(3-(phenyl)-[1,2,4]oxadiazol-5-yl)-phenoxy]-phenoxy}-pyrimidine-2,4,6-trione By the same procedures described in Example 36 but using 5-bromo-5-(2-ethoxy-ethyl)-pyrimidine-2,4,6-trione (from Preparation 3A) in Part C, the title compound was prepared. LC-MS (m/z, APCI): 530 [M+H]$^+$.

EXAMPLE 38

5-(2-Methoxy-ethyl)-5-{4-[4-(3-(2-fluorophenyl)-[1,2,4]oxadiazol-5-yl)-phenoxy]-phenoxy}-pyrimidine-2,4,6-trione By the same procedures described in Example 36 but using 2-fluorobenzonitrile in Part A, the title compound was prepared. LC-MS (m/z, APCI): 534 [M+H]$^+$.

EXAMPLE 39

5-(2-Ethoxy-ethyl)-5-{4-[4-(3-(2-fluorophenyl)-[1,2,4]oxadiazol-5-yl)-phenoxy]-phenoxy}-pyrimidine-2,4,6-trione By the same procedures described in Example 38 but using 5-bromo-5-(2-ethoxy-ethyl)-pyrimidine-2,4,6-trione (from Preparation 3A) in Part C, the title compound was prepared. LC-MS (m/z, APCI): 548 [M+H]$^+$.

EXAMPLE 40

5-(2-Methoxy-ethyl)-5-{4-[4-(3-(3-fluorophenyl)-[1,2,4]oxadiazol-5-yl)-phenoxy]-phenoxy}-pyrimidine-2,4,6-trione By the same procedures described in Example 36 but using 3-fluorobenzonitrile in Part A, the title compound was prepared. LC-MS (m/z, APCI): 532 [M+H]+.

EXAMPLE 41

5-(2-Ethoxy-ethyl)-5-{4-[4-(3-(3-fluorophenyl)-[1,2,4]oxadiazol-5-yl)-phenoxy]-phenoxy}-pyrimidine-2,4,6-trione By the same procedures described in Example 40 but using 5-bromo-5-(2-ethoxy-ethyl)-pyrimidine-2,4,6-trione (from Preparation 3A) in Part C, the title compound was prepared. LC-MS (m/z, APCI): 548 [M+H]+.

EXAMPLE 42

5-(2-Methoxy-ethyl)-5-{4-[4-(3-(4-fluorophenyl)-[1,2,4]oxadiazol-5-yl]-phenoxy-phenoxy}-pyrimidine-2,4,6-trione By the same procedures described in Example 36 but using 4-fluorobenzonitrile in Part A, the title compound was prepared. LC-MS (m/z, APCI): 533 [M+H]+.

EXAMPLE 43

5-(2-Ethoxy-ethyl)-5-{4-[4-(3-(4-fluorophenyl)-[1,2,4]oxadiazol-5-yl)-phenoxy]-phenoxy}-pyrimidine-2,4,6-trione By the same procedures described in Example 42 but using 5-bromo-5-(2-ethoxy-ethyl)-pyrimidine-2,4,6-trione (from Preparation 3A) in Part C, the title compound was prepared. LC-MS (m/z, APCI): 547 [M+H]+.

EXAMPLE 44

5-(2-Methoxy-ethyl)-5-{4-[4-(3-(2-chlorophenyl)-[1,2,4]oxadiazol-5-yl]-phenoxy-phenoxy}-pyrimidine-2,4,6-trione By the same procedures described in Example 36 but using 2-chlorobenzonitrile in Part A, the title compound was prepared. LC-MS (m/z, APCI): 548 [M+H]+.

EXAMPLE 45

5-(2-Ethoxy-ethyl)-5-{4-[4-(3-(2-chlorophenyl)-[1,2,4]oxadiazol-5-yl)-phenoxy]-phenoxy}-pyrimidine-2,4,6-trione By the same procedures described in Example 44 but using 5-bromo-5-(2-ethoxy-ethyl)-pyrimidine-2,4,6-trione (from Preparation 3A) in Part C, the title compound was prepared. LC-MS (m/z, APCI): 562 [M+H]+.

EXAMPLE 46

5-(2-Ethoxy-ethyl)-5-{4-[4-(3-(3-chlorophenyl)-[1,2,4]oxadiazol-5-yl)-phenoxy]-phenoxy}-pyrimidine-2,4,6-trione By the same procedures described in Example 37 but using 3-chlorobenzonitrile in Part A, the title compound was prepared. LC-MS (m/z, APCI): 564 [M+H]+.

EXAMPLE 47

5-(2-Methoxy-ethyl)-5-{4-[4-(3-(2-methylphenyl)-[1,2,4]oxadiazol-5-yl)-phenoxy]-phenoxy}-pyrimidine-2,4,6-trione By the same procedures described in Example 36 but using 2-methylbenzonitrile in Part A, the title compound was prepared. LC-MS (m/z, APCI): 528 [M+H]+.

EXAMPLE 48

5-(2-Ethoxy-ethyl)-5-{4-[4-(3-(2-methylphenyl)-[1,2,4]oxadiazol-5-yl)-phenoxy]-phenoxy}-pyrimidine-2,4,6-trione By the same procedures described in Example 47 but using 5-bromo-5-(2-ethoxy-ethyl)-pyrimidine-2,4,6-trione (from Preparation 3A) in Part C, the title compound was prepared. LC-MS (m/z, APCI): 542 [M+H]+.

EXAMPLE 49

5-(2-Methoxy-ethyl)-5-{4-[4-(3-(3-methyl]phenyl)-[1,2,4]oxadiazol-5-yl)-phenoxy]-phenoxy}-pyrimidine-2,4,6-trione By the same procedures described in Example 36 but using 3-methylbenzonitrile in Part A, the title compound was prepared. LC-MS (m/z, APCI): 528 [M+H]+.

EXAMPLE 50

5-(2-Ethoxy-ethyl)-5-{4-[4-(3-(3-methylphenyl)-[1,2,4]oxadiazol-5-yl)-phenoxy]-phenoxy}-pyrimidine-2,4,6-trione By the same procedures described in Example 49 but using 5-bromo-5-(2-ethoxy-ethyl)-pyrimidine-2,4,6-trione (from Preparation 3A) in Part C, the title compound was prepared. LC-MS (m/z, APCI): 542 [M+H]+.

EXAMPLE 51

5-(2-Ethoxy-ethyl)-5-{4-[4-(3-(2-pyridyl)-[1,2,4]oxadiazol-5-yl)-phenoxy]-phenoxy}-pyrimidine-2,4,6-trione By the same procedures described in Example 37 but using 2-cyanopyridine in Part A, the title compound was prepared. LC-MS (m/z, APCI): 531 [M+H]+.

EXAMPLE 52

5-(2-Ethoxy-ethyl)-5-{4-[4-(3-(3-pyridyl)-[1,2,4]oxadiazol-5-yl)-phenoxy]-phenoxy}-pyrimidine-2,4,6-trione By the same procedures described in Example 37 but using 3-cyanopyridine in Part A, the title compound was prepared. LC-MS (m/z, APCI): 531 [M+H]+.

EXAMPLE 53

5-(2-Ethoxy-ethyl)-5-{4-[4-(3-(4-pyridyl)-[1,2,4]oxadiazol-5-yl)-phenoxy]-phenoxy}-pyrimidine-2,4,6-trione By the same procedures described in Example 37 but using 4-cyanopyridine in Part A, the title compound was prepared. LC-MS (m/z, APCI): 531 [M+H]+.

EXAMPLE 54

5-(2-Methoxy-ethyl)-5-{4-[4-(3-(3-fluoropyrid-2-yl)-[1,2,4]oxadiazol-5-yl)-phenoxy]-phenoxy}-pyrimidine-2,4,6-trione By the same procedures described in Example 36 but using 2-cyano-3-fluoropyridine in Part A, the title compound was prepared. LC-MS (m/z, APCI): 535 [M+H]+.

EXAMPLE 55

5-(2-Ethoxy-ethyl)-5-{4-[4-(3-(3-fluoropyrid-2-yl)-[1,2,4]oxadiazol-5-yl)-phenoxy]-phenoxy}-pyrimidine-2,4,6-trione By the same procedures described in Example 54 but using 5-bromo-5-(2-ethoxy-ethyl)-pyrimidine-2,4,6-trione (from Preparation 3A) in Part C, the title compound was prepared. LC-MS (m/z, APCI): 548 [M+H]$^+$.

EXAMPLE 56

5-(2-Methoxy-ethyl)-5-{4-[4-(3-(2-pyrazinyl)-[1,2,4]oxadiazol-5-yl)-phenoxy]-phenoxy}-pyrimidine-2,4,6-trione By the same procedures described in Example 36 but using 2-cyanopyrazine in Part A, the title compound was prepared. LC-MS (m/z, APCI): 518 [M+H]$^+$.

EXAMPLE 57

5-(2-Ethoxy-ethyl)-5-{4-[4-(3-(2-pyrazinyl)-[1,2,4]oxadiazol-5-yl)-phenoxy]-phenoxy}-pyrimidine-2,4,6-trione By the same procedures described in Example 56 but using 5-bromo-5-(2-ethoxy-ethyl)-pyrimidine-2,4,6-trione (from Preparation 3A) in Part C, the title compound was prepared. LC-MS (m/z, APCI): 531 [M+H]$^+$.

EXAMPLE 58

5-(2-Ethoxy-ethyl)-5-{4-[4-(3-(2-Dyridazinyl)-[1,2,4]oxadiazol-5-yl)-phenoxy]-phenoxy}-pyrimidine-2,4,6-trione By the same procedures described in Example 37 but using 2-cyanopyridazine in Part A, the title compound was prepared. LC-MS (m/z, APCI): 531 [M+H]$^+$.

EXAMPLE 59

5-(2-Methoxy-ethyl)-5-{4-[4-(3-(2-furyl)-[1,2,4]oxadiazol-5-yl)-phenoxy]-phenoxy}-pyrimidine-2,4,6-trione By the same procedures described in Example 36 but using 2-cyanofuran in Part A, the title compound was prepared. LC-MS (m/z, APCI): 506 [M+H]$^+$.

EXAMPLE 60

5-(2-Ethoxy-ethyl)-5-{4-[4-(3-(2-furyl)-[1,2,4]oxadiazol-5-yl)-phenoxy]-phenoxy}-pyrimidine-2,4,6-trione By the same procedures described in Example 59 but using 5-bromo-5-(2-ethoxy-ethyl)-pyrimidine-2,4,6-trione (from Preparation 3A) in Part C, the title compound was prepared. LC-MS (m/z, APCI): 520 [M+H]$^+$.

EXAMPLE 61

5-(2—Benzyloxy-ethyl-5-{4-[4-(3-(2-fluorophenyl)-[1,2,4]oxadiazol-5-yl)-phenoxy]-phenoxy}-pyrimidine-2,4,6-trione By the same procedures described in Example 38 but using 5-bromo-5-(2—Benzyloxy-ethyl)-pyrimidine-2,4,6-trione (from Preparation 3C) in Part C, the title compound was prepared. LC-MS (m/z, APCI): 609 [M+H]$^+$.

EXAMPLE 62

5-(2-Hydroxy-ethyl)-5-{4-[4-(3-(2-fluorophenyl)-[1,2,4]oxadiazol-5-yl)-phenoxy]-phenoxy}-pyrimidine-2,4,6-trione By the same procedures described in Example 25 but using 5-(2—Benzyloxy-ethyl)-5-{4-[4-(3-(2-fluorophenyl)-[1,2,4]oxadiazol-5-yl)-phenoxy]-phenoxy}-pyrimidine-2,4,6-trione (from Example 61), the title compound was prepared. LC-MS (m/z, APCI): 519 [M+H]$^+$.

EXAMPLE 63

5-(2-Carboxy-ethyl)-5-{4-[4-(3-(2-fluorophenyl)-[1,2,4]oxadiazol-5-yl)-phenoxy]-phenoxy}-pyrimidine-2,4,6-trione A mixture of 5-(2-hydroxy-ethyl)-5-{4-[4-(3-(2-fluorophenyl)-[1,2,4]oxadiazol-5-yl)-phenoxy]-phenoxy}-pyrimidine-2,4,6-trione (518 mg, 1.0 mmol), sodium periodate (875 mg, 4.1 mmol), ruthenium trichloride hydrate (7 mg, 0.025 mmol), water (3 mL), acetonitrile (2 mL), and ethyl acetate (2 mL) was stirred vigorously for 4 hours. The mixture was filtered through diatomaceous earth which was then rinsed with ethyl acetate. The filtrate was washed with 10% sodium dithionite solution and brine and then dried over sodium sulfate. Filtration and concentration yielded 418 mg of the title compound as a white solid. LC-MS (m/z, APCI): 533 [M+H]$^+$.

EXAMPLE 64

5-(2-Methoxy-ethyl)-5-{4-[4-(5-(phenyl)-[1,2,4]oxadiazol-3-yl)-phenoxy]-phenoxy}-pyrimidine-2,4,6-trione By the same procedures described in Example 36 but using 4-(4-cyanophenoxy)phenol (from Preparation 8) in Part A, the title compound was prepared. LC-MS (m/z, APCI): 516 [M+H]$^+$.

EXAMPLE 65

5-(2-Ethoxy-ethyl)-5-{4-[4-(5-(phenyl)-[1,2,4]oxadiazol-3-yl)-phenoxy]-phenoxy}-pyrimidine-2,4,6-trione By the same procedures described in Example 64 but using 5-bromo-5-(2-ethoxy-ethyl)-pyrimidine-2,4,6-trione (from Preparation 3A) in Part C, the title compound was prepared. LC-MS (m/z, APCI): 530 [M+H]$^+$.

EXAMPLE 66

5-(2-Ethoxy-ethyl)-5-{4-[4-(5-(phenyl)-[1,3,4]oxadiazol-2-yl)-phenoxy]-phenoxy}-pyrimidine-2,4,6-trione Part A: Ethyl 4-(4-methoxyphenoxy)benzoate By the same procedure described in Preparation 7, Part B but using ethyl 4-fluorobenzoate and 4-methoxyphenol the title compound was prepared. LC-MS (m/z, APCI): 273 [M+H]$^+$.

Part B: N-(4-(4-methoxyphenoxy)benzoylhydrazine

Ethyl 4-(4-methoxyphenoxy)benzoate (7.71 g, 28.3 mmol) and hydrazine (9.07 g, 283 mmol) were refluxed together for 18 hours in ethanol (57 mL). The solvent was removed in vacuo and the residue chromatographed to give the title compound. LC-MS (m/z, APCI): 259 [M+H]$^+$.

Part C: N-(4-(4-methoxyphenoxy)benzoyl-N'-benzoylhydrazine

N-(4-(4-methoxyphenoxy)benzoylhydrazine (500 mg, 1.94 mmol) and triethylamine (306 mg, 3.00 mmol) were combined in dry tetrahydrofuran (8 mL). Benzoyl chloride (326 mg, 2.32 mmol) was then added dropwise and the mixture heated to reflux. After 5 minutes the reaction was allowed to cool to room temperature and the solvent removed in vacuo. Ethyl acetate was added and this was then washed with water and dried over sodium sulfate. Filtration and concentration gave a solid, which was chromatographed yielding the title compound. LC-MS (m/z, APCI): 363 [M+H]$^+$.

Part D: 2-(4-(4-methoxyphenoxy)phenyl-5-phenyl-[1,3,4]oxadiazole

By the procedure of Blackhall et al. (*J. Chem. Soc. Perkin 2* 1980, 773) N-(4-(4-methoxyphenoxy)benzoyl-N'-benzoylhydrazine (250 mg, 0.69 mmol) was converted to the title compound. LC-MS (m/z, APCI): 345 [M+H]$^+$.

Part E: 2-(4-(4-hydroxyphenoxy)phenyl-5-phenyl-[1,3,4]oxadiazole

By the same procedure described in Example 1, Part B, 2-(4-(4-methoxyphenoxy)phenyl-5-phenyl-[1,3,4]oxadiazole was converted to the title compound. LC-MS (m/z, APCI): 331 [M+H]$^+$.

Part F: 5-(2-Ethoxy-ethyl)-5-{4-[4-(5-(phenyl)-[1,3,4]oxadiazol-2-yl)-phenoxy]-phenoxy}-pyrimidine-2,4,6-trione By the same procedure described in Example 1, Part C, 2-(4-(4-hydroxyphenoxy)phenyl-5-phenyl-[1,3,4]oxadiazole was converted to the title compound. LC-MS (m/z, APCI): 530 [M+H]$^+$.

EXAMPLE 67

5-(2-Methoxy-ethyl)-5-{4-[4-(1-(4-fluorophenyl)-1H-pyrazol-3-yl)-phenoxy]-phenoxy}-pyrimidine-2,4,6-trione Part A: 1-[4-(4-Methoxy-phenoxy)-phenyl]-ethanone 4-methoxyphenol (12.4 g, 100 mmol) and 4-fluoroacetophenone (13.8 g, 100 mmol) were added to a flame dried 250 mL round bottom flask, and dissolved in dimethylacetamide (100 mL). K$_2$CO$_3$ (14.9 g, 120 mmol) was added, and the mixture was stirred for 16 hours at 135° C. The reaction was cooled to room temperature and water (160 mL) was added. The mixture was extracted with CH$_2$Cl$_2$, the combined organic layers were washed five times with water and once with brine. The organic layer was dried with MgSO$_4$, filtered and concentrated under vacuum to give 33.4 g crude product. The impurities were distilled off under vacuum (up to a bath temperature of 200° C.), to provide 16.9 g (70%) of the title compound as residual material. MS m/z: ESI+243 (M+H)$^+$.

Part B: 3-[4-(4-Methoxy-phenoxy)-phenyl]-1H-pyrazole

1-[4-(4-Methoxy-phenoxy)-phenyl]-ethanone (1.89 g, 7.8 mmol) and ethyl formate (1 mL, 11.7 mmol) were added to a flame dry flask and dissolved in toluene (13 mL), and stirred under N$_2$. Sodium methoxide (420 mg, 7.8 mmol) was added to a separate flame dry flask, and toluene (41 mL) was added to produce a slurry which was stirred under N$_2$. The solution of ketone and ethyl formate was added to the sodium methoxide slurry in one portion by syringe, and the resulting mixture was stirred for 1.5 hours at room temperature. The slurry which formed was filtered and rinsed with hexanes. The solid was dissolved in 20 ml methanol. Hydrazine hydrochloride (538 mg, 7.8 mmol) was dissolved in 15 ml H$_2$O and added dropwise to the methanol solution, a color change to bright yellow was observed, and the resulting mixture was stirred overnight at room temperature. Water was added and the solution was extracted with methylene chloride, washed with water and brine, dried over sodium sulfate, filtered, and concentrated under vacuum to provide 1.03 g of crude product. ISCO MPLC purification (30 minutes run, 0–50% EtOAC gradient, Biotage flash 40s column) gave 900 mg of the title compound (43%). MS m/z: APCI+267 (M+H)$^+$, APCI 266 (M)$^-$.

Part C: 1-(4-Fluoro-phenyl)-3-[4-(4-methoxy-phenoxy)-phenyl]-1H-pyrazole

3-[4-(4-Methoxy-phenoxy)-phenyl]-1H-pyrazole (300 mg, 1.12 mmol), 4-fluorophenylboronic acid (470 mg, 3.36 mmol), Cu(OAc)$_2$ (203 mg, 1.12 mmol), pyridine (450 µl, 5.6 mmol), and 4A molecular sieves were stirred in dimethyl sulfoxide (2 mL), and a stream of oxygen is bubbled through for 5 minutes. The reaction is then capped and stirred for 3.5 hours at room temperature, at which time LCMS indicated complete conversion to product. The reaction mixture was poured into 30 mL of water, and then filtered through Celite. The Celite was rinsed with ethyl acetate, and the filtrate was extracted with ethyl acetate (3×30 mL). The combined organic extracts were washed with 1N hydrochloric acid (1×30 mL) and with brine, dried over magnesium sulfate, filtered, and concentrated under vacuum to provide 650 mg of crude product. This material was used directly in the next step without further purification. MS m/z: APCI+361 (M+H)$^+$.

Part D: 4-{4-[1-(4-Fluoro-phenyl)-1H-pyrazol-3-yl]-phenoxy}-phenol 1-(4-Fluoro-phenyl)-3-[4-(4-methoxy-phenoxy)-phenyl]-1H-pyrazole (600 mg, crude material) was added to a round bottom flask. D,L-methionine (1.24 g, 8.3 mmol) and methanesulfonic acid (8.3 mL) were added and the solution stirred for a period of 12–72 hours, until LCMS indicated complete conversion to desired product. The mixture was then diluted with 2M sodium hydroxide, and the pH was adjusted to pH=7 using 1M hydrochloric acid. The aqueous layer was extracted 0.3 times with ethyl acetate, dried with sodium sulfate, and concentrated under vacuum to provide 400 mg crude product. ISCO MPLC purification (30 min. run, 0–50% sodium sulfate gradient, Biotage flash 40s column) gave 180 mg of the title compound (46% yield for 2 steps). MS m/z: ESI$^+$347 (M+H)$^+$.

Part E: 5-(2-Methoxy-ethyl)-5-{4-[4-(1-(4-fluorophenyl)-1H-pyrazol-3-yl)-phenoxy]phenoxy}-pyrimidine-2,4,6-trione By the same procedure as Example 1, Part C, 4-{4-[1-(4-Fluoro-phenyl)-1H-pyrazol-3-yl]-phenoxy}-phenol and 5-bromo-5-(2-methoxy-ethyl)-pyrimidine-2,4,6-trione (from Preparation 3B) were converted to the title compound. MS m/z: ESI+531.2 (M+H)$^+$.

EXAMPLE 68

5-(2-Ethoxy-ethyl)-5-{4-[4-(1-(4-fluorophenyl)-1H-pyrazol-3-yl)-phenoxy]-phenoxy}-pyrimidine-2,4,6-trione By the same procedure as Example 1, Part C, 4-{4-[1-(4-Fluoro-phenyl)-1H-pyrazol-3-yl]-phenoxy}-phenol (from Example 67, Part D) and 5-bromo-5-(2-ethoxy-ethyl)-pyrimidine-2,4,6-trione (from Preparation 3A) were converted to the title compound. MS m/z: ESI$^+$545.3 (M+H)$^+$.

EXAMPLE 69

5-(2-Methoxy-ethyl)-5-{4-[4-(1-(3-fluorophenyl)-1H-pyrazol-3-yl)-phenoxy]-phenoxy}-pyrimidine-2,4,6-trione Part A: 1-(3-Fluoro-phenyl)-3-[4-(4-methoxy-phenoxy)-phenyl]-1H-pyrazole By the same procedure as Example 67 Part C, 3-[4-(4-methoxy-phenoxy)-phenyl]-1H-pyrazole and 3-fluorophenylboronic acid were converted to the title compound. MS m/z: ESI$^+$361 (M+H)$^+$.

Part B: 4-{4-[1-(3-Fluoro-phenyl)-1H-pyrazol-3-yl]-phenoxy}-phenol

By the same procedure as Example 1, Part B, 1-(3-Fluorophenyl)-3-[4-(4-methoxy-phenoxy)-phenyl]-1H-pyrazole was converted to the title compound which was purified by chromatography. MS m/z: ESI$^+$347 (M+H)$^+$, ESI-345 (M–H)$^-$.

Part C: 5-(2-Methoxy-ethyl)-5-{4-[4-(1-(3-fluorophenyl)-pyrazol-3-yl)-phenoxy]-phenoxy}-pyrimidine-2,4,6-trione By the same procedure as Example 1, Part C, 4-{4-[1-(3-fluorophenyl)-1H-pyrazol-3-yl]-phenoxy}phenol and 5-bromo-5-(2-methoxyethyl)-pyrimidine-2,4,6-trione (from Preparation 3B) were converted to the title compound. MS m/z: ESI$^+$531.2 (M+H)$^+$, ESI 529.4 (M–H)$^-$.

EXAMPLE 70

5-(2-Ethoxy-ethyl)-5-{4-[4-(1-(3-fluorophenyl)-1H-pyrazol-3-yl)-phenoxy]-phenoxy}-pyrimidine-2,4,6-trione By the same procedure as Example 1, Part C, 4-{4-[1-(3-fluorophenyl)-1H-pyrazol-3-yl]-phenoxy}phenol and 5-bromo-5-(2-ethoxyethyl)-pyrimidine-2,4,6-trione (from Preparation 3B) were converted to the title compound. MS m/z: ESI+545.4 (M+H)$^+$, ESI-543.3 (M–H)$^-$.

EXAMPLE 71

5-(2-Methoxy-ethyl)-5-{4-[4-(3-(3-fluorophenyl)-1H-pyrazol-5-yl)-phenoxy]-phenoxy}-pyrimidine-2,4,6-trione Part A: 1-(3-Fluoro-phenyl)-3-[4-(4-methoxy-phenoxy)-phenyl]-propane-1,3-dione Diisopropylamine (517 μL, 3.7 mmol) was added to a flame dried flask, dissolved in 10 mL tetrahydrofuran, and the solution was stirred for 10 minutes at 0° C. n-Butyl Lithium, (1.35 mL, 2.5M, 3.4 mmol) was added and the solution was stirred for 30 minutes at 0° C., and for 10 minutes at −78° C. 1-[4-(4-Methoxy-phenoxy)-phenyl]-ethanone (745 mg, 3.1 mmol) was dissolved in 5 mL tetrahydrofuran and added to the reaction dropwise. The reaction was stirred at −78° C. for 40 minutes. 3-Fluorobenzoyl chloride (410 μL, 3.4,mmol) was added and the reaction was stirred for 90 minutes at −78° C., at which time LC/MS indicated the reaction was complete. The mixture was warmed to room temperature, 10 mL of saturated ammonium chloridel and 10 mL water were added. The solution was extracted with ethyl acetate (3×20 mL). The combined organic extracts were concentrated under vacuum to provide 1.4 g of crude product. This material was used directly in the next step without further purification. MS m/z: APCI$^-$ 363 (M–H)$^-$.

Part B: 3-(3-Fluoro-phenyl)-5-[4-(4-methoxy-phenoxy)-phenyl]-1H-pyrazole 1-(3-Fluoro-phenyl)-3-[4-(4-methoxy-phenoxy)-phenyl]-propane-1,3-dione (1.4 g, crude material) was dissolved in 40 mL methanol. Hydrazine hydrochloride (211 mg, 3.1 mmol) was dissolved in 6 mL water and added to the methanol solution dropwise. The reaction was stirred at room temperature for 5 hours, at which point TLC indicated no reaction was taking place. The mixture was heated to 70° C. for 14 hours, at which point the reaction was complete by TLC. The mixture was cooled to room temperature, 40 mL of water was added and the solution was extracted with methylene chloride (3×40 mL). The organic extracts were combined and washed with water (2×70 mL) and brine. The solution was dried with sodium sulfate and concentrated under vacuum to provide crude product (xx). ISCO MPLC purification (40 minutes. run, 0–50% EtOAC gradient, Biotage flash 40s column) gave 410 mg of the title compound (37% yield for 2 steps). MS m/z: APCI$^+$361 (M+H)$^+$, APCI–359 (M–H)$^-$.

Part C: 4-{4-[5-(3-Fluoro-phenyl)-2H-pyrazol-3-yl]-phenoxy}-phenol

By the same procedure as Example 1, Part B, 3-(3-Fluorophenyl)-5-[4-(4-methoxy-phenoxy)-phenyl]-1H-pyrazole was converted to the title compound. MS m/z: ESI$^+$347 (M+H)$^+$, ESI$^-$ 345 (M–H)$^-$.

Part D: 5-(2-Methoxy-ethyl)-5-{4-[4-(3-(3-fluorophenyl)-1H-pyrazol-5-yl)-phenoxy]-phenoxy}-pyrimidine-2,4,6-trione By the same procedure as Example 1, Part C, 4-{4-[1-(3-fluorophenyl)-1H-pyrazol-3-yl]-phenoxy}phenol and 5-bromo-5-(2-methoxyethyl)-pyrimidine-2,4,6-trione (from Preparation 3B) were converted to the title compound. MS m/z: ESI$^+$ 531.1 (M+H)$^+$, ESI-529.2 (M–H)$^-$

EXAMPLE 72

5-(2-Ethoxy-ethyl)-5-{4-[4-(3-(3-fluorophenyl)-1H-pyrazol-5-yl)-phenoxy]-phenoxy}-pyrimidine-2,4,6-trione By the same procedure as Example 1, Part C, 4-{4-[1-(3-fluorophenyl)-1H-pyrazol-3-yl]-phenoxy}phenol (from Example 71, Part C) and 5-bromo-5-(2-ethoxyethyl)-pyrimidine-2,4,6-trione (from Preparation 3B) were converted to the title compound. MS m/z: ESI$^+$ 545.1 (M+H)$^+$, ESI$^-$ 543.3 (M–H)$^-$.

EXAMPLE 73

(S) 5-(2-Ethoxy-ethyl)-5-{4-[4-(4-(phenyl)-4,5-dihydrooxazol-2-yl)-phenoxy]-phenoxy}-pyrimidine-2,4,6-trione Part A: (S)4-(4-hydroxyphenoxy)benzoic acid N-2-hydroxy-1-phenylethyl amide A solution of 2-(1H-benxotriazol-1-yl)-1,1,3,3-tetramethyluronium tetrafluoroborate (706 mg, 2.2 mmol), 1-hydroxybenztriazole (54 mg, 0.4 mmol), diisopropylethylamine (1.29 g, 10.0 mmol), 4-(4-hydroxyphenoxy)benzoic acid (460 mg, 2.0 mmol) and (S) 2-hydroxy-1-phenylethylamine (302 mg, 2.2 mmol) in dimethylformamide (3.2 mL) was stirred at room temperature for 18 hours. The mixture was diluted with ethyl acetate and washed with 1N hydrochloric acid, saturated sodium bicarbonate solution, and brine. The extract was dried with magnesium sulfate, filtered and concentrated to a white solid. Drying under high vacuum gave 756 mg of the title compound. LC-MS (m/z, APCI): 350 [M+H]$^+$.

Part B: (S) 4-[4-(4-(phenyl)-4,5-dihydrooxazol-2-yl)-phenoxy]-phenol

Thionyl chloride (3 mL) was added to (S)4-(4-hydroxyphenoxy)benzoic acid N-2-hydroxy-1-phenylethyl amide (700 mg, 2.0 mmol) at 0° C. After 30 minutes ethyl ether was added precipitating the product. After 2 hours the solid was collected, rinsed with ethyl ether. The solid was taken up in acetonitrile and reconcentrated to give a solid which was purified by chromatography yielding 127 mg of the title compound. LC-MS (m/z, APCI): 332 [M+H]$^+$.

Part C: (S) 5-(2-Ethoxy-ethyl)-5-{4-[4-(4-(phenyl)-4,5-dihydrooxazol-2-yl)-phenoxy]-phenoxy}-pyrimidine-2,4,6-trione By the same procedure as Example 1, Part C, (S) 4-[4-(4-(phenyl)-4,5-dihydrooxazol-2-yl)-phenoxy]-phenol (from Example 73, Part B) and 5-bromo-5-(2-ethoxyethyl)- pyrimidine-2,4,6-trione (from Preparation 3B) were converted to the title compound. LC-MS (m/z, APCI): 531 [M+H]⁺.

EXAMPLE 74

(R) 5-(2-Ethoxy-ethyl)-5-{4-[4-(4-(phenyl)-4,5-dihydrooxazol-2-yl)-phenoxy]-phenoxy}-pyrimidine-2,4,6-trione By the same procedures described in Example 73 but using (R) 2-hydroxy-1-phenylethylamine in Part A, the title compound was prepared. LC-MS (m/z, APCI): 531 [M+H]⁺.

EXAMPLE 75

5-(4-{4-[1-(4-Chloro-phenyl)-1H-pyrazol-3-yl]-phenoxy}-phenoxy)-5-(2-methoxy-ethyl)-pyrimidine-2,4,6-trione Part A: 1-(4-Chloro-phenyl)-3-[4-(4-methoxy-phenoxy)-phenyl]-1H-pyrazole By the same procedure as Example 67 Part C, 3-[4-(4-methoxy-phenoxy)-phenyl]-1H-pyrazole and 4-chlorophenylboronic acid were converted to the title compound. MS m/z: ESI⁺ 377.1 (M+H)⁺.

Part B: 4-{4-[1-(4-Chloro-phenyl)-1H-pyrazol-3-yl]-phenoxy}-phenol

By the same procedure as Example 1, Part B, 1-(4-Chloro-phenyl)-3-[4-(4-methoxy-phenoxy)-phenyl]-1H-pyrazole was converted to the title compound. MS m/z: ESI⁺363.0 (M+H)⁺, ESI⁻ 361.2 (M−H)⁻.

Part C: 5-(4-{4-[1-(4-Chloro-phenyl)-1H-pyrazol-3-yl]-phenoxy}-phenoxy)-5-(2-methoxy-ethyl)-pyrimidine-2,4,6-trione By the same procedure as Example 1, Part C, 4-{4-[1-(4-Chloro-phenyl)-1H-pyrazol-3-yl]-phenoxy}-phenol and 5-bromo-5-(2-methoxyethyl)-pyrimidine-2,4,6-trione (from Preparation 3B) were converted to the title compound. MS m/z: ESI⁺ 547.1 (M+H)⁺, ESI⁻ 545.3 (M−H)⁻.

EXAMPLE 76

5-(2-Methoxy-ethyl)-5-{4-[4-(1-p-tolyl-1H-pyrazol-3-yl)-phenoxy]-phenoxy}-pyrimidine-2,4,6-trione Part A: 3-[4-(4-Methoxy-phenoxy)-phenyl]-1-p-tolyl-1H-pyrazole By the same procedure as Example 67 Part C, 3-[4-(4-methoxy-phenoxy)-phenyl]-1H-pyrazole and p-tolylboronic acid were converted to the title compound. MS m/z: APCI⁺ 357.1 (M+H)⁺.

Part B: 4-[4-(1-p-Tolyl-1H-pyrazol-3-yl)-phenoxy]-phenol

By the same procedure as Example 1, Part B, 3-[4-(4-methoxy-phenoxy)-phenyl]-1-p-tolyl-1H-pyrazole was converted to the title compound. MS m/z: ESI⁺ 343.1 (M+H)⁺, ESI⁻ 341.3 (M−H)⁻.

Part C: 5-(2-Methoxy-ethyl)-5-{4-[4-(1-p-tolyl-1H-pyrazol-3-yl)-phenoxy]-phenoxy}-pyrimidine-2,4,6-trione By the same procedure as Example 1, Part C, 4-[4-(1-p-Tolyl-1H-pyrazol-3-yl)-phenoxy]-phenol and 5-bromo-5-(2-methoxyethyl)-pyrimidine-2,4,6-trione (from Preparation 3B) were converted to the title compound. MS m/z: ESI⁺ 527.2 (M+H)⁺, ESI⁻ 525.4 (M−H)⁻.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula

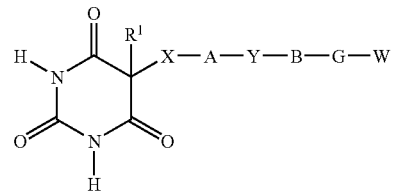

or a pharmaceutically acceptable salt thereof, wherein $R^1$ is selected from the group consisting of hydrogen, $(R^2)_{2n+1}$—(C)$_n$— and $(C_3$–$C_7)$cycloalkyl; wherein said $(C_3$–$C_7)$cycloalkyl may be optionally substituted on any ring carbon atom able to support an additional substituent by one to two substituents independently selected from the group consisting of halo, $(C_1$–$C_4)$alkyl, $(C_1$–$C_4)$alkenyl, $(C_1$–$C_4)$alkynyl, $R^3$—, $R^3$—O—, perfluoro$(C_1$–$C_4)$alkoxy, $R^3$—$(C_1$–$C_4)$alkyl-O—, $R^3$—(C=O)—O—, $(R^3)_2$N—(C=O)—O—, —NO$_2$, $(R^3)_2$N—, $R^3$—(C=O)—(NR$^4$)—, $R^3$—(SO$_2$)—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—(SO$_2$)—, $(R^3)_2$N—(SO$_2$)—, —CN, $R^3$—(C=O)—, $R^3$—O—(C=O)— and $(R^3)_2$N—(C=O)—;

n is an integer from one to five;

each $R^2$ is independently selected from the group consisting of halo, $(C_1$–$C_4)$alkenyl, $(C_1$–$C_4)$alkynyl, $R^3$—, $R^3$—O—, perfluoro$(C_1$–$C_4)$alkoxy, $R^3$—(C=O)—O—, $(R^3)_2$N—(C=O)—O—, —NO$_2$, $(R^3)_2$N—, $R^3$—(SO$_2$)—(NR$^4$)—, $(R^3)_2$—N—(C=O)—, $R^3$—(C=O)—(NR$^4$)—, $R^3$O—(C=O)—(NR$^4$)—, $(R^3)_2$—N—(C=O)—(NR$^4$)—, $R^3$—S—, $R^3$—(S=O)—, $R^3$—(SO$_2$)—, $(R^3)_2$N—(SO$_2$)—, —CN, $R^3$—O—(C=O)—, and $R^3$—(C=O)—;

wherein not more than three of said $R^3$ may be other than hydrogen and any one carbon atom of said —(C)$_n$— component of the $R^1$ can contain only one bond to a heteroatom;

wherein a carbon atom of any two $R^2$ may be taken together with the carbons to which they are attached to form a four to ten membered ring;

each $R^3$ is independently selected from the group consisting of hydrogen, $(C_1$–$C_4)$alkyl, $(C_6$–$C_{10})$aryl, $(C_3$–$C_7)$cycloalkyl, $(C_1$–$C_{10})$heteroaryl and $(C_1$–$C_{10})$heterocyclyl; wherein each $R^3$ may be optionally substituted on any carbon atom able to support an additional substituent by one to three substituents, wherein said substituents are independently selected from the group consisting of halo, hydroxy, amino, —CN, $(C_1-C_4)$alkyl, $(C_1-C_4)$alkoxy, $(C_1-C_4)$alkyl-NH—, $[(C_1-C_4)$alkyl$]_2$—N—, $(C_6-C_{10})$aryl, $(C_3-C_7)$cycloalkyl, $(C_1-C_{10})$heteroaryl and $(C_1-C_{10})$heterocyclyl;

wherein each of said $R^3$ $(C_3-C_7)$cycloalkyl and $(C_1-C_{10})$heterocyclyl may be optionally substituted on any ring carbon atoms capable of supporting two additional substituents with one to two oxo groups per ring;

wherein each of said $R^3$ $(C_1-C_{10})$heteroaryl and $(C_1-C_{10})$heterocyclyl may be optionally substituted on any ring nitrogen atom able to support an additional substituent independently selected from the group consisting of $(C_1-C_4)$alkyl, $(C_1-C_4)$alkyl-(C=O)—, $(C_6-C_{10})$aryl, $(C_3-C_7)$cycloalkyl, $(C_1-C_{10})$heteroaryl and $(C_1-C_{10})$heterocyclyl;

$R^4$ is selected from the group consisting of hydrogen and $(C_1-C_4)$alkyl;

wherein said $R^3$ may be optionally taken together with said $R^4$ to form a three to eight membered ring;

X is selected from the group consisting of —O—, >C=O, —S—, >SO$_2$, >S=O, >NR$^5$, —CH$_2$—, —CH$_2$O—, —OCH$_2$—, —CH$_2$S—, —CH$_2$(S=O)—, —CH$_2$SO$_2$—, —SCH$_2$—, —(S=O)CH$_2$—, —SO$_2$CH$_2$—, —[N(R$^5$)]CH$_2$—, —CH$_2$[N(R$^5$)]—, —[N(R$^5$)]SO$_2$— and —SO$_2$[N(R$^5$)]—;

$R^5$ is selected from the group consisting of hydrogen and $(C_1-C_4)$alkyl;

A is $(C_6-C_{10})$aryl or $(C_1-C_{10})$heteroaryl;

Y is selected from the group consisting of a bond, —O—, —S—, >C=O, >SO$_2$, >S=O, —CH$_2$O—, —OCH$_2$—, —CH$_2$S—, —SCH$_2$—, —CH$_2$SO—, —CH$_2$SO$_2$—, —SOCH$_2$—, —SO$_2$CH$_2$—, >NR$^6$, —[N(R$^6$)]CH$_2$—, —CH$_2$[N(R$^6$)]—, —CH$_2$—, —CH=CH—, —C≡C—, [N(R$^6$)]—SO$_2$— and —SO$_2$[N(R$^6$)]—;

$R^6$ is selected from the group consisting of hydrogen and $(C_1-C_4)$alkyl;

B is selected from the group consisting of $(C_6-C_{10})$aryl, $(C_3-C_7)$cycloalkyl, $(C_1-C_{10})$heterocyclyl and $(C_1-C_{10})$heteroaryl; wherein one or two carbon-carbon single bonds of said B $(C_3-C_7)$cycloalkyl or $(C_1-C_{10})$heterocyclyl may optionally be replaced by carbon-carbon double bonds;

wherein G is bonded to one ring carbon atom of B;

wherein each of said A or B may be independently optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy;

G is —[R$^7$—(CR$^8$R$^9$)$_p$]—; wherein the orientation of -B-G-W is -B-[R$^7$—(CR$^8$R$^9$)$_p$]-W or -B-[(CR$^8$R$^9$)$_p$—R$^7$]-W;

p is an integer from zero to four;

R7 is independently selected from the group consisting of $(C_3-C_7)$cycloalkyl, $(C_6-C_{10})$aryl, $(C_1-C_{10})$heteroaryl and $(C_1-C_{10})$heterocyclyl;

wherein each of said $(C_6-C_{10})$aryl, $(C_3-C_7)$cycloalkyl $(C_1-C_{10})$heteroaryl and $(C_1-C_{10})$heterocyclyl may be optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, $[(C_1-C_4)$alkyl$]_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N$[(C_1-C_4)$alkyl$]_2$;

wherein each of said $R^7$ $(C_3-C_7)$cycloalkyl and $(C_1-C_{10})$heterocyclyl may optionally be substituted on any ring carbon atoms capable of supporting two additional substituents with one to two oxo groups per ring;

wherein each of said $R^7$ $(C_1-C_{10})$heteroaryl and $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

each of $R^8$ and $R^9$ is independently selected from the group consisting of hydrogen and $(C_1-C_4)$alkyl;

or $R^8$ and $R^9$ may optionally be taken together with the carbon to which they are attached to form a 3 to 8-membered carbocyclic ring;

W is selected from the group consisting of $(C_1-C_4)$alkoxy $(C_1-C_4)$alkyl, $(C_3-C_7)$cycloalkyl, $(C_6-C_{10})$aryl, $(C_1-C_{10})$heteroaryl and $(C_1-C_{10})$heterocyclyl;

wherein each of said W $(C_3-C_7)$cycloalkyl, $(C_6-C_{10})$aryl, $(C_1-C_{10})$heteroaryl and $(C_1-C_{10})$heterocyclyl may be optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy;

wherein each of said W $(C_3-C_7)$cycloalkyl and $(C_1-C_{10})$heterocyclyl may optionally be substituted on any ring carbon atoms capable of supporting two additional substituents with one to two oxo groups per ring;

wherein each of said W $(C_1-C_{10})$heteroaryl and $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

wherein each $(C_1-C_{10})$heteroaryl in all occurrences is selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; and wherein each $(C_1-C_{10})$heterocyclyl in all occurrences is selected from the group consisting of 3-azabicycl[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxetanyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrehydropyranyl, 1,2,3,6-tetrahydrpyridinyl, tetrahydrothienyl, tertahydrothiopyranyl, thiomorpholinyl, thioxanyl, and trithianyl.

2. The compound according to claim 1 wherein W is $(C_1-C_4)$alkoxy$(C_1-C_4)$alkyl.

3. The compound according to claim 1 wherein W is $(C_3-C_7)$cycloalkyl optionally substituted on any of the ring carbon atoms capable of supporting an additional substituent by one to three substituents per ring independently selected from F, Cl, Br, CN, OH, $(C_1-C_4)$alkyl,$(C_1-C_4)$alkoxy $(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; and wherein said W $(C_3-C_7)$cycloalkyl may optionally be substituted on any ring carbon atoms capable of supporting two additional substituents with one to two oxo groups per ring.

4. A compound according to claim 3, wherein said W $(C_3-C_7)$cycloalkyl is selected from the group consisting of optionally substituted cyclopropyl, cyclobutyl, cyclopentyl, cyclohexyl, and cycloheptyl.

5. The compound according to claim 1 wherein W is $(C_3-C_{10})$aryl optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoralkoxy, $(C_1-C_4)$alkoxy, and $(C_3-C_7)$cycloalkyloxy.

6. A compound according to claim 1, wherein W is $(C_1-C_{10})$heteroaryl optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; and wherein said W $(C_1-C_{10})$heteroaryl may be also optionally substituted on any ring nitrogen atom able to support an additional substituent independently selected from the group consisting of $(C_1-C_4)$alkyl and $(C_1-C_4)$alkyl-(C=O)—.

7. A compound according to claim 6, wherein said W $(C_1-C_{10})$heteroaryl is selected from the group consisting of furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl.

8. A compound according to claim 6, wherein said W $(C_1-C_{10})$heteroaryl is selected from the group consisting of pyridinyl, pyrimidinyl, pyrazinyl.

9. A compound according to claim 1, wherein W is $(C_1-C_{10})$heterocyclyl optionally substituted on any of the ring carbon atoms capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; wherein said $(C_1-C_{10})$heterocyclyl may optionally be substituted on any ring carbon atoms capable of supporting two additional substituents with one to two oxo groups per ring; and wherein said $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—.

10. A compound according to claim 9, wherein said W $(C_1-C_{10})$heterocyclyl is selected from the group consisting of azetidinyl, hexahydroazepinyl, hexahydropyrimidine, morpholinyl, piperazinyl, piperidinyl, pyrrolidinyl, thiomorpholinyl, tetrahydrofuranyl, tetrahydropyranyl, and oxetanyl.

11. The compound according to claim 1, wherein said G is —[$R^7$—$(CR^8R^9)_p$]—; wherein p is zero.

12. The compound according to claim 11, wherein $R^7$ is $(C_3-C_7)$cycloalkyl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$; and wherein said $R^7$ $(C_3-C_7)$cycloalkyl may optionally be substituted on any ring carbon atoms capable of supporting two additional substituents with one to two oxo groups per ring.

13. The compound according to claim 11, wherein $R^7$ is $(C_6-C_{10})$aryl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$.

14. The compound according to claim 11, wherein $R^7$ is $(C_1-C_{10})$heteroaryl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$.

15. A compound according to claim 14, wherein G is oxazol-2-yl or oxazol-5-yl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$.

16. A compound according to claim 14, wherein G is isooxazol-5-yl or isooxazol-3-yl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$—N—, $(C_3-C_7)$cycloalkyloxy, —(C=O)—OH, —(C=O)—O—$(C_1C_4)$alkyl, —(C=O)—NH$_2$, —(C=O)—NH—$(C_1-C_4)$alkyl, and —(C=O)—N[$C_1-C_4$)alkyl]$_2$.

17. A compound according to claim 14, wherein G is oxadiazol-2-yl, oxadiazol-3-yl, or oxadiazol-5-yl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$.

18. A compound according to claim 14, wherein G is pyrazolyl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-$, $(C_1-C_4)$alkyl, and $-(C=O)-N[(C_1-C_4)$alkyl$]_2$.

19. The compound according to claim 11, wherein $R^7$ is $(C_1-C_{10})$heterocyclyl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$; and wherein said $(C_1-C_{10})$heterocyclyl may optionally be substituted on any ring carbon atoms capable of supporting two additional substituents with one to two oxo groups per ring.

20. The compound according to claim 1, wherein said G is $-[R^7-(CR^8R^9)_p]-$; wherein p is an integer from one to four.

21. The compound according to claim 20, wherein $R^7$ is $(C_3-C_7)$cycloalkyl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$; and wherein said $R^7$ $(C_3-C_7)$cycloalkyl may optionally be substituted on any ring carbon atoms capable of supporting two additional substituents with one to two oxo groups per ring.

22. The compound according to claim 20, wherein $R^7$ is $(C_6-C_{10})$aryl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$.

23. The compound according to claim 20, wherein $R^7$ is $(C_1-C_{10})$heteroaryl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$.

24. The compound according to claim 20, wherein $R^7$ is $(C_1-C_{10})$heterocyclyl optionally substituted on any of the ring carbon atoms capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, $-NH_2$, $-NO_2$, $(C_1-C_4)$alkyl-NH—, $[(C_1-C_4)$alkyl$]_2$—N—, $(C_3-C_7)$cycloalkyloxy, $-(C=O)-OH$, $-(C=O)-O-(C_1-C_4)$alkyl, $-(C=O)-NH_2$, $-(C=O)-NH-(C_1-C_4)$alkyl, and $-(C=O)-N[(C_1-C_4)$alkyl$]_2$; and wherein said $(C_1-C_{10})$heterocyclyl may optionally be substituted on any ring carbon atoms capable of supporting two additional substituents with one to two oxo groups per ring.

25. The compound according to claim 20, wherein each of $R^8$ and $R^9$ are hydrogen.

26. The compound according to claim 20, wherein $R^8$ and $R^9$ are taken together with the carbon to which they are attached to form a 3 to 8-membered carbocyclic ring.

27. The compound according to claim 1, wherein X is $-O-$, $-S-$, $>SO_2$, $>S=O$, $>NR^5$, or $-CH_2-$.

28. The compound according to claim 1, wherein X is $-O-$ or $>NR^5$.

29. The compound according to claim 1, wherein X is $-O-$.

30. A compound according to claim 1, wherein Y is a bond, $-O-$, $-S-$, $-CH_2-$, $>SO_2$, $-OCH_2-$ or $-CH_2O-$.

31. A compound according to claim 1, wherein Y is $-O-$, $-OCH_2-$ or $-CH_2O-$.

32. A compound according to claim 1, wherein Y is $-O-$.

33. The compound according to claim 1, wherein X and Y are each $-O-$.

34. A compound according to claim 1, wherein A is $(C_6-C_{10})$aryl optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

35. A compound according to claim 1, wherein A is $(C_1-C_{10})$heteroaryl optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

36. The compound according to claim 1 wherein said B is $(C_6-C_{10})$aryl optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

37. The compound according to claim 1 wherein said B is $(C_3-C_7)$cycloalkyl, $(C_1-C_{10})$heteroaryl or $(C_1-C_{10})$heterocyclyl optionally substituted on any of the ring carbon atoms capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy.

38. The compound according to claim 1, wherein the orientation of -B-G-W is -B-[R$^7$—(CR$^8$R$^9$)$_p$]-W.

39. The compound according to claim 1, wherein the orientation of -B-G-W is -B-[(CR$^8$R$^9$)$_p$—R$^7$]$_W$.

40. The compound according to claim 38, wherein the orientation of -B-G-W is —(C$_6$–C$_{10}$)aryl-[(C$_1$–C$_{10}$)heteroaryl-(CR$^8$R$^9$)$_p$]—(C$_6$–C$_{10}$)aryl; wherein p is zero; wherein each of said B (C$_6$–C$_{10}$)aryl and W (C$_6$–C$_{10}$)aryl are optionally substituted on any of the ring carbon atoms capable of supporting an additional substituent by one to three substituents per ring independently selected from F, Cl, Br, CN, OH, (C$_1$–C$_4$)alkyl, (C$_1$–C$_4$)perfluoroalkyl, (C$_1$–C$_4$)perfluoroalkoxy, (C$_1$–C$_4$)alkoxy, (C$_1$–C$_4$)alkoxy(C$_1$–C$_4$)alkyl, —NH$_2$, (C$_1$–C$_4$)alkyl-NH—, [(C$_1$–C$_4$)alkyl]$_2$—N— and (C$_3$–C$_7$)cycloalkyloxy; and wherein said G (C$_1$–C$_{10}$)heteroaryl is optionally substituted on any of the ring carbon atoms capable of supporting an additional substituent by one to three substituents per ring independently selected from F, Cl, Br, CN, OH, (C$_1$–C$_4$)alkyl, (C$_1$–C$_4$)perfluoroalkyl, (C$_1$–C$_4$)perfluoroalkoxy, (C$_1$–C$_4$)alkoxy, (C$_1$–C$_4$)alkoxy (C$_1$–C$_4$)alkyl, —NH$_2$, —NO$_2$, (C$_1$–C$_4$)alkyl-NH—, [(C$_1$–C$_4$)alkyl]$_2$—N—, (C$_3$–C$_7$)cycloalkyloxy, —(C=O)—OH, —(C=O)—O—(C$_1$–C$_4$)alkyl, —(C=O)—NH$_2$, —(C=O)—NH—(C$_1$–C$_4$)alkyl, and —(C=O)—N [(C$_1$–C$_4$)alkyl]$_2$.

41. The compound according to claim 1, wherein R$^1$ is (R$^2$)$_{2n+1}$—(C)$_n$—, n is an integer from one to four;
R$^2$ is independently selected from the group consisting of R$^3$—, R$^3$—O—, (R$^3$)$_2$N—, R$^3$—S—, R$^3$—(S=O)—, R$^3$—(SO$_2$)—, R$^3$—(SO$_2$)—(NR$^4$)—, R$^3$—NH—(SO$_2$)—, (R$^3$)$_2$N—(SO$_2$)—, R$^3$—(C=O)—(NR$^4$)—, R$^3$—(C=O)—O—, R$^3$—O—(C=O)— and R$^3$—(C=O)—; and
each R$^3$ is independently selected from the group consisting of hydrogen, (C$_1$–C$_4$)alkyl, (C$_6$–C$_{10}$)aryl, (C$_3$–C$_7$)cycloalkyl, (C$_1$–C$_{10}$)heteroaryl and (C$_1$–C$_{10}$)heterocyclyl;
wherein each R$^3$ (C$_1$–C$_4$)alkyl may be optionally substituted by one to three substituents independently selected from the group consisting of halo, hydroxy, amino, —CN, (C$_1$–C$_4$)alkyl, (C$_1$–C$_4$)alkoxy, (C$_1$–C$_4$)alkyl-NH—, [(C$_1$–C$_4$)alkyl]$_2$—N—(C$_6$–C$_{10}$)aryl, (C$_3$–C$_7$)cycloalkyl, (C$_1$–C$_{10}$)heteroaryl and (C$_1$–C$_{10}$)heterocyclyl;
wherein each R$^3$ (C$_6$–C$_{10}$)aryl, (C$_3$–C$_7$)cycloalkyl, (C$_1$–C$_{10}$)heteroaryl and (C$_1$–C$_{10}$)heterocyclyl may be optionally substituted on any ring carbon atom capable of supporting an additional substituent by one to three substituents per ring independently selected from the group consisting of halo, hydroxy, amino, —CN, (C$_1$–C$_4$)alkyl, (C$_1$–C$_4$)alkoxy, (C$_1$–C$_4$)alkyl-NH—, [(C$_1$–C$_4$)alkyl]$_2$—N—, (C$_6$–C$_{10}$)aryl, (C$_3$–C$_7$)cycloalkyl, (C$_1$–C$_{10}$)heteroaryl and (C$_1$–C$_{10}$)heterocyclyl.

42. The compound according to claim 41, wherein R$^1$ is (R$^2$)$_{2n+1}$—(C)$_n$—, n is two;
each R$^2$ is independently selected from the group consisting of R$^3$— and R$^3$—O—;
wherein not more than three of said R$^2$ may be other than hydrogen and any one carbon atom of said —(C)$_n$— component of said R$^1$ can contain only one bond to a heteroatom;
each R$^3$ is independently selected from the group consisting of hydrogen and (C$_1$–C$_4$)alkyl; wherein each R$^3$ (C$_1$–C$_4$)alkyl may be optionally substituted by one to three substituents independently selected from the group consisting of (C$_6$–C$_{10}$)aryl, (C$_3$–C$_7$)cycloalkyl, (C$_1$–C$_{10}$)heteroaryl and (C$_1$–C$_{10}$)heterocyclyl.

43. The compound according to claim 41, wherein R$^1$ is (R$^2$)$_{2n+1}$—(C)$_n$—, n is two;
each R$^2$ is independently selected from the group consisting of R$^3$— and R$^3$—O—;
wherein any four of said R$^3$ are hydrogen and any one of said R$^3$ is (C$_1$–C$_4$)alkyl;
wherein each R$^3$ (C$_1$–C$_4$)alkyl may be optionally substituted by one to three substituents independently selected from the group consisting of (C$_3$–C$_6$)aryl, (C$_3$–C$_7$)cycloalkyl, (C$_1$–C$_{10}$)heteroaryl and (C$_1$–C$_{10}$)heterocyclyl.

44. The compound according to claim 15, wherein said compound is selected from the group consisting of:

5-(4-{4-[4-(2-Fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(2-fluoro-phenyl)-oxazol-2-yl]-phenoxy}-phenoxy)-pyrimidine-2,4,6-trione;

5-(4-{4-[4-(4-Fluoro-phenyl)-oxazol-2-yl]-phenoxy}-phenoxy)-5-methoxymethyl-pyrimidine-2,4,6-trione;

5-(4-{4-[4-(4-fluoro-phenyl)-oxazol-2-yl]-phenoxy}-phenoxy)-5-(2-methoxy-ethyl)-pyrimidine-2,4,6-trione;

5-(2-Ethoxy-ethyl)-5-(4-{4-[4-(4-fluoro-phenyl)-oxazol-2-yl]-phenoxy}-phenoxy)-pyrimidine-2,4,6-trione;

2-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

2-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

4-[2-(4-{4-[5-(2-Methoxy-ethyl)-2,4,6-trioxo-hexahydro-pyrimidin-5-yloxy]-phenoxy}-phenyl)-oxazol-4-yl]-benzonitrile;

4-[2-(4-{4-[5-(2-Ethoxy-ethyl)-2,4,6-trioxo-hexahydro-pyrimidin-5-yloxy]-phenoxy}-phenyl)-oxazol-4-yl]-benzonitrile;

5-(2-Methoxy-ethyl)-5-{4-[4-(4-pyridin-2-yl-oxazol-2-yl)-phenoxy]-phenoxy}-pyrimidine-2,4,6-trione;

5-(2-Ethoxy-ethyl)-5-{4-[4-(4-pyridin-2-yl-oxazol-2-yl)-phenoxy]-phenoxy}-pyrimidine-2,4,6-trione;

5-(2-Methoxy-ethyl)-5-{4-[4-(4-pyridin-4-yl-oxazol-2-yl)-phenoxy]-phenoxy}-pyrimidine-2,4,6-trione;

5-(2-Methoxy-ethyl)-5-{4-[4-(5-phenyl-oxazol-2-yl)-phenoxy]-phenoxy}pyrimidine-2,4,6-trione;

5-(2-Methoxy-ethyl)-5-{4-[4-(2-phenyl-oxazol-5-yl)-phenoxy]-phenoxy}pyrimidine-2,4,6-trione;

5-(2-Ethoxy-ethyl)-5-{4-[4-(2-phenyl-oxazol-5-yl)-phenoxy]-phenoxy}pyrimidine-2,4,6-trione;

5-(4-{4-[3-(2-Chloro-phenyl)-[1,2,4]oxadiazol-5-yl]-phenoxy}-phenoxy)-5-(2-methoxy-ethyl)-pyrimidine-2,4,6-trione;

5-(4-{4-[3-(2-Fluoro-phenyl)-[1,2,4]oxadiazol-5-yl]-phenoxy}-phenoxy)-5-(2-methoxy-ethyl)-pyrimidine-2,4,6-trione;

5-(2-Ethoxy-ethyl)-5-(4-{4-[3-(2-fluoro-phenyl)-[1,2,4]oxadiazol-5-yl]-phenoxy}-phenoxy)-pyrimidine-2,4,6-trione;

5-(4-{4-[3-(3–Chloro-phenyl)-[1,2,4]oxadiazol-5-yl]-phenoxy}-phenoxy)-5-(2-ethoxy-ethyl)-pyrimidine-2,4,6-trione;

5-(2-Ethoxy-ethyl)-5-{4-[4-(3-pyridin-3-yl-[1,2,4]oxadiazol-5-yl)-phenoxy]-phenoxy}-pyrimidine-2,4,6-trione;

5-(2-Ethoxy-ethyl)-5-{4-[4-(3-pyridin-4-yl-[1,2,4]oxadiazol-5-yl)-phenoxy]-phenoxy}-pyrimidine-2,4,6-trione;

5-(2-Methoxy-ethyl)-5-{4-[4-(1-(4-fluorophenyl)-1H-pyrazol-3-yl)-phenoxy]-phenoxy}-pyrimidine-2,4,6-trione;

5-(2-Ethoxy-ethyl)-5-{4-[4-(1-(4-fluorophenyl)-1H-pyrazol-3-yl)-phenoxy]-phenoxy}-pyrimidine-2,4,6-trione;

5-(2-Methoxy-ethyl)-5-{4-[4-(1-(3-fluorophenyl)-1H-pyrazol-3-yl)-phenoxy]-phenoxy}-pyrimidine-2,4,6-trione; or 5-(2-Ethoxy-ethyl)-5-{4-[4-(1-(3-fluorophenyl)-1H-pyrazol-3-yl)-phenoxy]-phenoxy}-pyrimidine-2,4,6-trione; or a pharmaceutically acceptable salt thereof.

45. A pharmaceutical composition for the treatment of a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers in a mammal, including a human, comprising an amount of a compound of claim 1 effective in such treatment and a pharmaceutically acceptable carrier.

46. A method for treating a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers in a mammal, including a human, comprising administering to said mammal an amount of a compound of claim 1, effective in treating such a condition.

47. A pharmaceutical composition for the treatment of a condition which can be treated by the inhibition of matrix metalloproteinases in a mammal, including a human, comprising an amount of a compound of claim 1 effective in such treatment and a pharmaceutically acceptable carrier.

48. A method for the inhibition of matrix metalloproteinases in a mammal, including a human, comprising administering to said mammal an effective amount of a compound of claim 1.

49. A method for treating a medical condition of the type that is characterized by the destruction of articular cartilage in a mammalian subject, which method comprises administering to the subject having said condition a therapeutically effective amount of a compound of claim 1, wherein said compound of claim 1 exhibits: i) a ratio of MMP-1 $IC_{50}$/MMP-13 $IC_{50}$ of about 50, and ii) a ratio of MMP-14 $IC_{50}$/MMP-13 $IC_{50}$ of about 50; wherein said MMP-1 $IC_{50}$ is measured by a recombinant MMP-1 assay; wherein each of said MMP-13 $IC_{50}$ is measured by a recombinant MMP-13 assay; and wherein said MMP-14 $IC_{50}$ is measured by a recombinant MMP-14 assay.

50. A method according to claim 49 wherein said compound of claim 1 exhibits iii) a ratio of MMP-12 $IC_{50}$/MMP-13 $IC_{50}$ of about 50; wherein said MMP-12 $IC_{50}$ is measured by a recombinant MMP-12 assay; and wherein said MMP-13 $IC_{50}$ is measured by a recombinant MMP-13 assay.

51. A method according to claim 49 wherein said compound of claim 1 exhibits iv) a ratio of MMP-2 $IC_{50}$/MMP-13 $IC_{50}$ of about 50, and v) a ratio of MMP-3 $IC_{50}$/MMP-13 $IC_{50}$ of about 50; vi) a ratio of MMP-7 $IC_{50}$/MMP-13 $IC_{50}$ of about 50, and vii) a ratio of MMP-9 $IC_{50}$/MMP-13 $IC_{50}$ of about 50; wherein said MMP-2 $IC_{50}$ is measured by a recombinant MMP-2 assay; wherein said MMP-3 $IC_{50}$ is measured by a recombinant MMP-3 assay; wherein said MMP-7 $C_{50}$ is measured by a recombinant MMP-7 assay; wherein said MMP-9 $IC_{50}$ is measured by a recombinant MMP-9 assay; and each of said MMP-13 $IC_{50}$ is measured by $IC_{50}$ is measured by a recombinant MMP-7 assay; wherein said MMP-9 $IC_{50}$ is measured

52. A method according to claim 51 wherein said compound of claim 1 exhibits a MMP-13 $IC_{50}$ of less than about 50 nM.

53. A method according to claim 51 wherein said compound of claim 1 exhibits an MMP-13 $IC_{50}$ of less than about 20 nM.

* * * * *